US011918252B2

United States Patent
Ross et al.

(10) Patent No.: US 11,918,252 B2
(45) Date of Patent: Mar. 5, 2024

(54) DEFORMABLE DYNAMIZATION DEVICE

(71) Applicant: Texas Scottish Rite Hospital for Children, Dallas, TX (US)

(72) Inventors: John D. Ross, Ovilla, TX (US); Mikhail L. Samchukov, Coppell, TX (US); Alexander M. Cherkashin, Flower Mound, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 409 days.

(21) Appl. No.: 17/081,082

(22) Filed: Oct. 27, 2020

(65) Prior Publication Data

US 2021/0038263 A1 Feb. 11, 2021

Related U.S. Application Data

(63) Continuation of application No. 15/787,327, filed on Oct. 18, 2017, now Pat. No. 10,874,434.

(51) Int. Cl.
| | |
|---|---|
| *A61B 17/66* | (2006.01) |
| *A61B 17/62* | (2006.01) |
| *A61B 17/64* | (2006.01) |
| *A61B 17/68* | (2006.01) |
| *A61B 17/00* | (2006.01) |
| *A61B 17/60* | (2006.01) |

(52) U.S. Cl.
CPC .............. *A61B 17/66* (2013.01); *A61B 17/62* (2013.01); *A61B 17/6475* (2013.01); *A61B 17/68* (2013.01); *A61B 2017/00526* (2013.01); *A61B 2017/606* (2013.01); *A61B 17/6491* (2013.01); *A61B 2017/681* (2013.01)

(58) Field of Classification Search
CPC .......... A61B 17/60–666; A61B 17/7019–7031
See application file for complete search history.

(56) References Cited

U.S. PATENT DOCUMENTS

| | | | |
|---|---|---|---|
| 3,977,397 A | 8/1976 | Kalnberg et al. | |
| 5,788,695 A | 8/1998 | Richardson | |
| 8,162,994 B2 * | 4/2012 | Gimbel | A61B 17/7019 606/279 |
| 8,187,330 B2 * | 5/2012 | Gimbel | A61F 2/4425 623/17.15 |

(Continued)

OTHER PUBLICATIONS

International Searching Authority, Notification of Transmittal of the International Search Report and the Written Opinion of the International Searching Authority, or the Declaration, dated Dec. 20, 2018, 17 pages, International Application No. PCT/US2018/056321.

*Primary Examiner* — Eduardo C Robert
*Assistant Examiner* — Steven J Cotroneo
(74) *Attorney, Agent, or Firm* — Haynes and Boone, LLP

(57) ABSTRACT

A dynamization device includes a first module and a second module. The first and second modules are each rigidly affixed to and mated together by one or more deformable rings. Each of the first and second modules includes an inner column positioned within the one or more deformable rings. The mated first and second modules form a first displacement gap between the inner column of the first module and the inner column of the second module. The first displacement gap extends along the longitudinal axis between adjacent deformable rings of the one or more deformable rings.

14 Claims, 37 Drawing Sheets

(56) References Cited

U.S. PATENT DOCUMENTS

| | | | |
|---|---|---|---|
| 8,292,963 B2* | 10/2012 | Miller | A61F 2/44 606/252 |
| 8,574,232 B1* | 11/2013 | Ross | A61B 17/66 606/57 |
| 8,685,022 B2* | 4/2014 | Lorenz | A61B 17/6416 606/259 |
| 8,740,980 B2 | 6/2014 | Merves | |
| 9,289,238 B2 | 3/2016 | Ross | |
| 9,717,530 B1* | 8/2017 | Ross | A61B 17/6491 |
| 2005/0171543 A1* | 8/2005 | Timm | A61B 17/7034 606/279 |
| 2005/0203509 A1 | 9/2005 | Chinnaian | |
| 2007/0270814 A1* | 11/2007 | Lim | F16F 1/028 606/279 |
| 2007/0288009 A1* | 12/2007 | Brown | A61B 17/7025 606/279 |
| 2008/0045951 A1 | 2/2008 | Fanger | |
| 2009/0299411 A1* | 12/2009 | Laskowitz | A61B 17/7043 606/264 |
| 2010/0125273 A1 | 5/2010 | Schweiger et al. | |
| 2015/0157371 A1 | 6/2015 | Ehmke et al. | |
| 2015/0216564 A1 | 6/2015 | Salomone | |
| 2015/0257800 A1* | 9/2015 | Harshman | A61B 17/7283 606/62 |
| 2015/0305776 A1 | 10/2015 | Ross et al. | |
| 2016/0106471 A1* | 4/2016 | Lynch | A61B 17/7025 606/258 |
| 2016/0135845 A1* | 5/2016 | Mehdian | A61B 17/7032 606/250 |

* cited by examiner

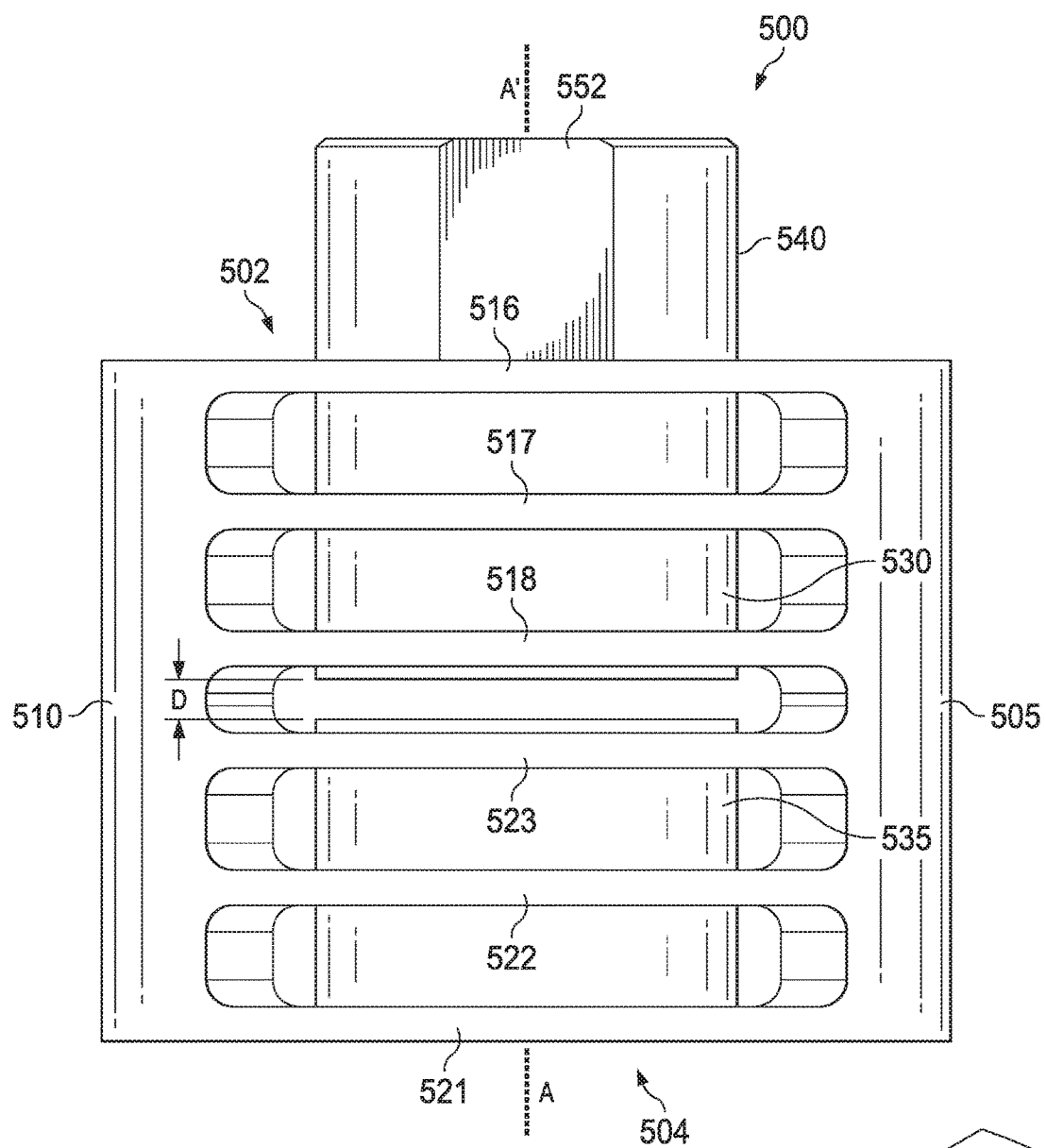
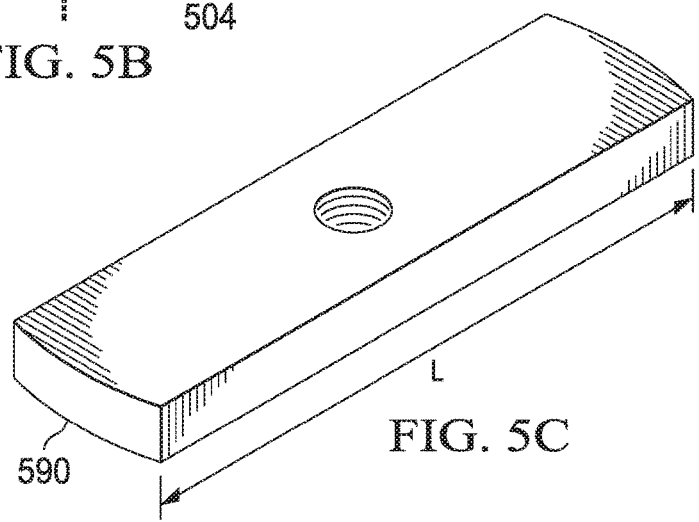
FIG. 5B
FIG. 5C

DEFORMABLE DYNAMIZATION DEVICE

PRIORITY

The present disclosure is a continuation of U.S. patent application Ser. No. 15/787,327, filed Oct. 18, 2017, which is incorporated herein by reference in its entirety.

FIELD OF THE DISCLOSURE

The present disclosure relates in general to the field of fixation devices used in the therapeutic treatment of bone fractures. More specifically, devices of the present disclosure may provide for controlled axial destabilization (dynamization) of corresponding fixation devices.

BACKGROUND OF THE DISCLOSURE

Without limiting the scope of the disclosure, this background is described in connection with external fixation devices and specifically connection struts and rods. Generally, external fixation devices are commonly used in a variety of surgical procedures including limb lengthening, deformity correction, fracture reduction, and treatment of non-unions, mal-unions, and bone defects. The process involves a rigid framework comprising one or more rings that are placed externally around the limb and attached to bone segments using wires and half pins, which are inserted into the bone segments and connected to the related section of the external rigid framework. The opposite rings of the rigid framework are interconnected by either threaded or telescopic rods directly or in conjunction with uni-planar or multi-planar hinges, which allow the surgeon to connect opposite rings that are not parallel to each other after manipulation with bone segments either rapidly (acutely) or gradually over a period of time.

For example, in bone fracture reduction or non-union treatment, the wires and half pins are inserted into each bone segment and attached to rings of a rigid framework. The rigid framework can be used to acutely reduce a displacement and restore alignment between the bone segments. During the realignment of the bone segments, the orientation of opposite rings is often not parallel. Those opposite rings of the rigid framework are connected together by threaded or telescopic rods either directly or with attached uni-planar or multi-planar hinges. This allows the opposite bone segment to be rigidly fixed until completion of fracture healing or bone consolidation.

For various bone treatments, introducing controlled axial destabilization of the frame can accelerate bone healing and significantly improve the strength of the fracture callus or distraction bone regenerate. Gradually increasing a load is an important part of the bone healing process. To achieve such controlled destabilization, the external fixation devices can be dynamized. There are many ways of achieving dynamization, examples including, for a unilateral fixator, removing its bars, sliding the bars further away from the bone, removing its pins, and/or releasing tension or compression from the system, and for a circular frame, removing its wires, releasing tension from the wires, removing its connection rods between rings, removing the rings from a ring block, and/or releasing tension or compression from the system. These techniques can be problematic since they often result in wide variations in the level of instability and may not effectively limit the dynamization to a desired direction or axis of movement.

SUMMARY

A dynamization device is described herein. According to one embodiment, the dynamization device has a longitudinal axis and may comprise a first module having a first longitudinal axis. The first module many comprise an outer wall having a substantially cylindrical shape, a semicircular cap located at a first end of the outer wall, the cap comprising a central aperture, an inner column located at a second end of the outer wall, the inner column comprising a threaded recess at the second end, a stopping member radially protruding from the second end of the inner column, wherein the outer wall, the central aperture, the threaded recess, and the inner column are substantially coaxial with the first longitudinal axis. The device may also comprise a second module may have a second longitudinal axis and comprise an outer wall having a substantially cylindrical shape, a semicircular cap located at a first end of the outer wall, the cap comprising a central aperture, an inner column located at a first end of the outer wall, the inner column comprising a threaded recess at the first end that is aligned with the central aperture of the semicircular cap, wherein the outer wall, the central aperture, the threaded recess, and the inner column are substantially coaxial with the second longitudinal axis. The first and second modules can be mated together such that inner column of the first module is positioned within the outer wall of the second module and the inner column of the second module is positioned within the outer wall of the first module so that the first and second longitudinal axes are coaxial. The mated first and second modules may form a first displacement gap between the inner column of the first module and the inner column of the second module and a second displacement gap between the second end of the second module and the stopping member of the first module, wherein the first and second displacement gaps have a substantially similar longitudinal distance.

The device may also comprise a plurality of first deformable rings positioned at the first end of the mated first and second modules. The plurality of first deformable rings may comprise a first deformable ring positioned at a first end of the first and second modules and connected to a portion the outer wall of the first module and connected to a portion of the outer wall of the second module by first ring connectors that are radially positioned opposite each other, thereby permitting the first and second modules to be longitudinally displaced with respect to each other by deforming the first deformable ring. The plurality of first deformable rings may further comprise a second deformable ring longitudinally displaced from the first deformable ring and connected to a portion of the outer wall of the first module and connected to a portion of the outer wall of the second module by second ring connectors that are radially positioned opposite each other, thereby permitting the first and second modules to be longitudinally displaced with respect to each other by deforming the second deformable ring. The plurality of first deformable rings may further comprise a third deformable ring longitudinally displaced from the second deformable ring and connected to a portion of the outer wall of the first module and connected to a portion of the outer wall of the second module by third ring connectors that are radially positioned opposite each other, thereby permitting the first and second modules to be longitudinally displaced with respect to each other by deforming the third deformable ring. The first, second, and third ring connectors may be positioned at first, second, and third radial positions, respectively, with respect to the longitudinal axis. The second radial position can be substantially 45 degrees with respect to the first radial position and the third radial position can be substantially 90 degrees with respect to the first radial position.

The device may also comprise a plurality of second deformable rings positioned at the second end of the mated first and second modules. The plurality of second deformable rings may comprise a fourth deformable ring positioned at the second end of the first and second modules and connected to a portion the outer wall of the first module and connected to a portion of the outer wall of the second module by fourth ring connectors that are radially positioned opposite each other thereby permitting the first and second modules to be longitudinally displaced with respect to each other by deforming the fourth deformable ring. The plurality of second deformable rings may further comprise a fifth deformable ring longitudinally displaced from the fourth deformable ring and connected to a portion of the outer wall of the first module and connected to a portion of the outer wall of the second module by fifth ring connectors that are radially positioned opposite each other, thereby permitting the first and second modules to be longitudinally displaced with respect to each other by deforming the fifth deformable ring. The plurality of second deformable rings may further comprise a sixth deformable ring longitudinally displaced from the fifth deformable ring and connected to a portion of the outer wall of the first module and connected to a portion of the outer wall of the second module by sixth ring connectors that are radially positioned opposite each other, thereby permitting the first and second modules to be longitudinally displaced with respect to each other by deforming the sixth deformable ring. The fourth, fifth, and sixth ring connectors can be positioned at fourth, fifth and sixth radial positions, respectively, with respect to the longitudinal axis. The fifth radial position can be substantially 45 degrees with respect to the fourth radial position, and the sixth radial position can be substantially 90 degrees with respect to the fourth radial position. Each of the ring connectors described above can connect to one of the first and second modules through about 90 degrees of angular space.

According to one embodiment, the outer walls of the first and second modules can be substantially cylindrical, but other shapes can be utilized. The inner columns of the first and second modules may also substantially cylindrical, but other shapes can be utilized.

According to another embodiment, a first threaded rod can be received within the first threaded aperture in the first module and a second threaded rod can be received within the second threaded aperture to attach the device to a fixator device. One or more threaded fastener can be threaded on to one of the threaded rods so as the prevent the first and second modules from moving longitudinally with respect to each other. By backing the threaded fastener away from the device, the threaded fastener can be used to control the amount of therapeutic dynamization that is applied by the device to a bone fracture.

The deformable rings, or even the entire device, may be comprised of a material having appropriate elasticity and shape memory, such material can be selected from plastic, polymer, thermoplastic, metal, metal alloy, composite, resin, ultra-high-molecular-weight polyethylene (UHMW), a polytetrafluroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. In certain non-limiting examples the polymer can be a thermoplastic polymer, a polyolefin, a polyester, a polysilicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a polysulfone, a polycarbonate, a polyacetal, poly(hydroxynapthoic acid), a conductive polymer, a poly(3-hexyl-thiophene), a polyphenylene-vinylene, a poly(phenylene vinylene), a polyaniline, or combinations thereof. Other appropriate and biocompatible materials can be utilized. According to another embodiment, the dynamization device can be fabricated by an additive printing process (e.g., a 3D printing process).

According to another embodiment, a dynamization device with a longitudinal axis may comprise a first module having an outer wall with a substantially cylindrical shape, a semicircular cap located at a first end of the outer wall with the cap comprising a central aperture, an inner column located at a second end of the outer wall, the inner column comprising a threaded recess at the second end, wherein the outer wall, the central aperture, the threaded recess, and the inner column are substantially coaxial with the longitudinal axis. The device may also comprise a second module having an outer wall with a substantially cylindrical shape, a semicircular cap located at a first end of the outer wall with the cap comprising a central aperture, and an inner column located at a first end of the outer wall, the inner column having a threaded recess at the first end that is aligned with the central aperture of the semicircular cap, wherein the outer wall, the central aperture, the threaded recess, and the inner column are substantially coaxial with the longitudinal axis. The first and second modules can be mated together such that inner column of the first module is positioned within the outer wall of the second module and the inner column of the second module is positioned within the outer wall of the first module. The mated first and second modules can form a displacement gap between the inner column of the first module and the inner column of the second module. The device may also comprise a plurality of proximal deformable rings positioned at the first end of the mated first and second modules and a plurality of distal deformable rings positioned at the second end of the mated first and second modules.

The plurality of proximal deformable rings may comprise a first deformable ring positioned at a first end of the first and second modules and connected to a portion the semicircular cap of the first module and connected to a portion of the semicircular cap of the second module by first ring connectors that are radially positioned opposite each other thereby permitting the second module to be longitudinally displaced with respect to the first module by deforming the first ring. The plurality of proximal deformable rings may further comprise a second deformable ring longitudinally positioned away from the first deformable ring and connected to a portion of the outer wall of the first module and connected to a portion of the outer wall of the second module by second ring connectors that are radially positioned opposite each other, thereby permitting the second module to be longitudinally displaced with respect to the first module by deforming the second ring. The plurality of proximal deformable rings may further comprise a third deformable ring longitudinally positioned away from the second deformable ring and connected to a portion of the outer wall of the first module and connected to a portion of the outer wall of the second module by third ring connectors that are radially positioned opposite each other, thereby permitting the second module to be longitudinally displaced with respect to the first module by deforming the third ring. The plurality of proximal deformable rings may further comprise a fourth deformable ring longitudinally positioned away from the third deformable ring and connected to a portion of the outer wall of the first module and connected to a portion of the outer wall of the second module by fourth ring connectors that are radially positioned opposite each other, thereby permitting the second module to be longitudinally displaced with respect to the first module by deforming the fourth ring. The first, second, third, and fourth ring connectors can be positioned at first, second, third, and fourth radial positions, respectively, with respect to the longitudinal axis.

The plurality of proximal deformable rings may further comprise at least two first outer columns connecting the first outer ring to the second outer ring, wherein one of the first outer columns can be connected to the outer wall of the first module and another of the first outer columns can be connected to the outer wall of the second module, wherein the first outer columns are positioned on radially opposite sides of the device.

The plurality of proximal deformable rings may further comprise at least two second outer columns connecting the second outer ring to the third outer ring, wherein one of the second outer columns can be connected to the outer wall of the first module and another of the second outer columns can be connected to the outer wall of the second module, and wherein the second outer columns can be positioned on radially opposite sides of the device.

The plurality of proximal deformable rings may further comprise at least two third outer columns connecting the third outer ring to the fourth outer ring, wherein one of the third outer columns can be connected to the outer wall of the first module and another of the third outer columns can be connected to the outer wall of the second module, and wherein the third outer columns can be positioned on radially opposite sides of the device.

The plurality of distal deformable rings can be positioned at the second end of the mated first and second modules. The plurality of distal deformable rings can comprise a fifth deformable ring positioned at a second end of the first and second modules and connected to a portion the outer wall of the second module and connected to a portion of the outer wall of the first module by fifth ring connectors that can radially positioned opposite each other thereby permitting the first and second modules to be longitudinally displaced with respect to each other by deforming the fifth ring. The plurality of distal deformable rings may further comprise a sixth deformable ring longitudinally positioned away from the fifth deformable ring and connected to a portion of the outer wall of the first module and connected to a portion of the outer wall of the second module by fifth ring connectors that can be radially positioned opposite each other, thereby permitting the first and second modules to be longitudinally displaced with respect to each other by deforming the sixth ring. The plurality of distal deformable rings may further comprise a seventh deformable ring longitudinally positioned away from the sixth deformable ring and connected to a portion of the outer wall of the first module and connected to a portion of the outer wall of the second module by seventh ring connectors that can be radially positioned opposite each other, thereby permitting the first and second modules to be longitudinally displaced with respect to each other by deforming the seventh ring. The plurality of distal deformable rings may further comprise an eighth deformable ring longitudinally positioned away from the seventh deformable ring and connected to a portion of the outer wall of the first module and connected to a portion of the outer wall of the second module by eighth ring connectors that can be radially positioned opposite each other, thereby permitting the first and second modules to be longitudinally displaced with respect to each other. The fifth, sixth, seventh, and eighth ring connectors can be positioned at fifth, sixth, seventh, and eighth radial positions, respectively, with respect to the longitudinal axis.

The plurality of distal deformable rings may further comprise at least two fourth outer columns connecting the fifth outer ring to the sixth outer ring, wherein one of the fourth outer columns can be connected to the outer wall of the first module and another of the fourth outer columns can be connected to the outer wall of the second module, and wherein the fourth outer columns can be positioned on radially opposite sides of the device.

The plurality of distal deformable rings may further comprise at least two fifth outer columns connecting the sixth outer ring to the seventh outer ring, wherein one of the fifth outer columns can be connected to the outer wall of the first module and another of the fifth outer columns can be connected to the outer wall of the second module, and wherein the fifth outer columns can be positioned on radially opposite sides of the device.

The plurality of distal deformable rings may further comprise at least two sixth outer columns connecting the seventh outer ring to the eighth outer ring, wherein one of the sixth outer columns can be connected to the outer wall of the first module and another of the sixth outer columns can be connected to the outer wall of the second module, and wherein the sixth outer columns can be positioned on radially opposite sides of the device.

The device may further comprise a proximal minor column connected to a portion of the outer wall of the first module, and a portion of the fourth deformable ring, wherein the distance between the proximal minor column and the eighth deformable ring can be substantially equal to the displacement gap. The device may further comprise a proximal major column connected to a portion of the outer wall of the second module and a portion of the fourth deformable ring, wherein the proximal major column can be adjacent to the eighth deformable ring, and wherein the proximal major column can be positioned on a radially opposite side of the device from the proximal minor column. The device may further comprise a distal minor column connected to a portion of the outer wall of the second module, and a portion of the eighth deformable ring, wherein the distance between the distal minor column and the fourth deformable ring can be substantially equal to the displacement gap. The device may further comprise a distal major column connected to a portion of the outer wall of the first module and a portion of the eighth deformable ring, wherein the distal major column can be adjacent to the fourth deformable ring, wherein the distal major column can be positioned on a radially opposite side of the device from the distal minor column.

BRIEF DESCRIPTION OF THE DRAWINGS

Some embodiments of the disclosure may be understood by referring, in part, to the present disclosure and the accompanying drawings, wherein:

FIG. 5B illustrates a side view of one embodiment of a dynamization device;

FIG. 5C illustrates a perspective view of one embodiment of a locking device suitable for use with one embodiment of a dynamization device;

FIG. 5E illustrates a top view of an alternative embodiment of a dynamization device;

DETAILED DESCRIPTION

The present disclosure relates in general to the field of external fixation rods and struts. More specifically, dynamization devices of the present disclosure may provide for controlled axial destabilization (dynamization) of corresponding external fixation devices. Embodiments of the present disclosure may advantageously provide for varying degrees of compressive movement of a biasing member of a dynamization device. Such features may advantageously provide for different degrees or amounts of dynamization in a corresponding external fixation device thereby increasing axial micromotion of bone segments. By controlling the amount of dynamization applied to the device, a therapeutically appropriate amount of dynamization can be applied at regular intervals during the fracture healing process or bone remodeling. Mechanical stimulation of newly formed bony tissues with parallel to the longitudinal anatomical axis of the bone segment speeds up their ossification thereby resulting in orientation of mineralized bone trabeculae also parallel to the bone axis. Thus, the healing process for fractures and remodeling of the reconstructed bone can be expedited and improved.

Figure 1A:
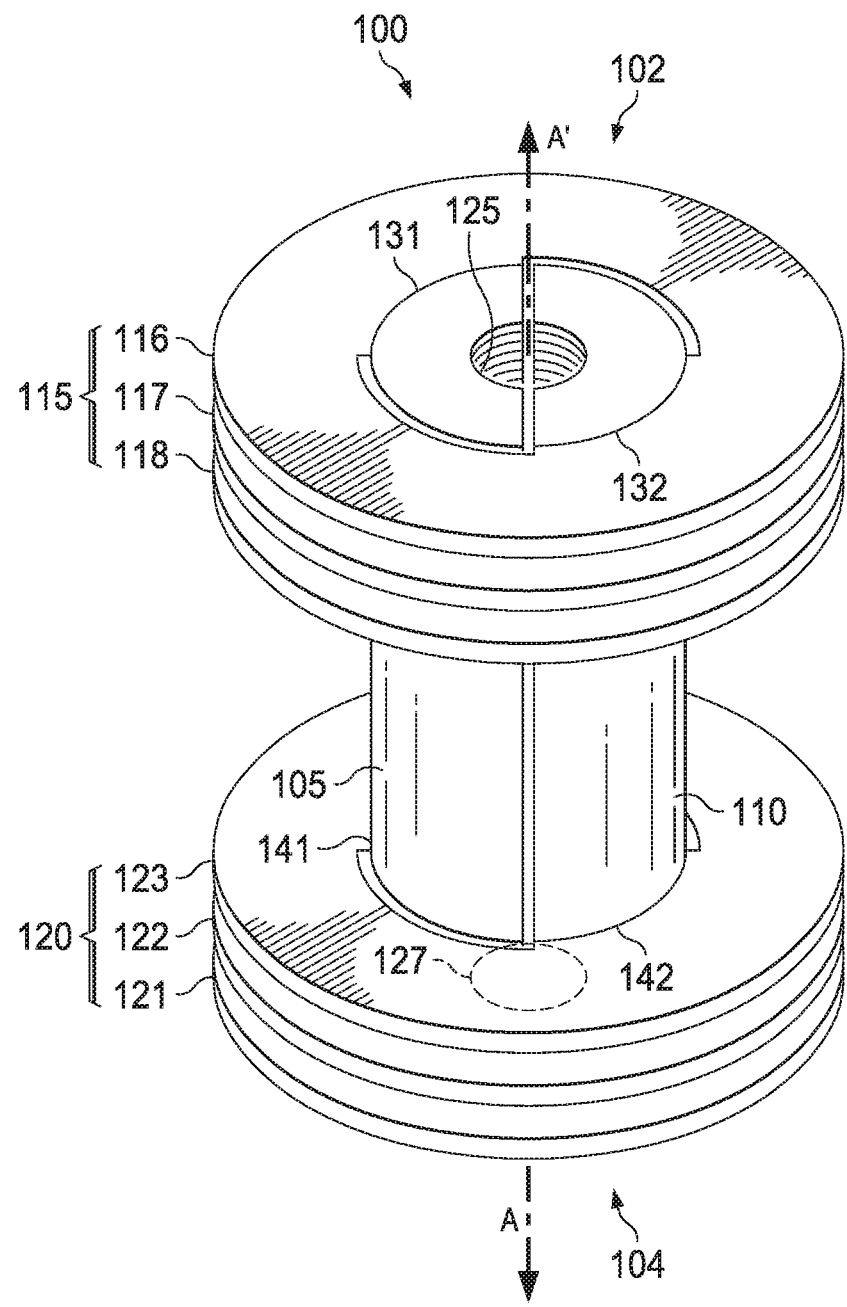
FIG. 1A illustrates a perspective view of one embodiment of a dynamization device.

One representative embodiment of a dynamization device is depicted in FIG. 1A. In FIG. 1A, a dynamization device 100 has a generally cylindrical shape along a longitudinal axis A-A'. The dynamization device 100 is comprised of a first module 105 and a second module 110 that are mated together so that the longitudinal axis of the first module 105 is coaxial to the longitudinal axis of the second module 110 and the longitudinal axis A-A' of the dynamization device 100. Positioned at a first end 102 of the dynamization device 100 is a set of first deformable rings 115. Positioned at a second end 104 of the dynamization device 100 is a set of second deformable rings 120. In the embodiment depicted in FIG. 1A, the set of first deformable rings 115 may comprise a first deformable ring 116, a second deformable ring, 117, and a third deformable ring 118. As few as one deformable ring may be used for each set of deformable rings, and many more than three deformable rings may be used for each set of deformable rings without departing from the spirit of the invention. The set of second deformable rings 120 may similarly comprise a fourth deformable ring 121, a fifth deformable ring 122, and a sixth deformable ring 123. Each ring is connected to a portion of the first and second modules 105, 110 by one or more ring connectors. The connection of the first deformable ring 116 to the first and second modules 105, 110 is depicted in FIG. 1A with first ring connectors 131 and 132. These ring connectors (131, 132) may occupy a radial position and are opposite each other with respect to the longitudinal axis A-A'. Also shown in FIG. 1A is the connection of sixth deformable ring 123 to the first and second modules 105, 110 by sixth ring connectors 141 and 142. These ring connectors (141, 142) may occupy a radial position and are opposite each other with respect to the longitudinal axis A-A'. Although two ring connectors are depicted in FIG. 1A to connect the deformable rings to the first and second modules 105, 110, a plurality of connectors can be used without departing from the spirit of the invention. Also shown in FIG. 1A is threaded aperture 125 that is located at the first end 102 of the second module 110. The threaded aperture may be used to connect a threaded bolt, rod, or other connector to a first end 102 of the dynamization device 100. Not shown in FIG. 1A, is another threaded aperture 127 that is located at the second end 104 of the first module 105. This other threaded aperture 127 may be used to connect a threaded bolt, rod, or other connector to the second end 104 of the dynamization device 100.

Figure 1B:
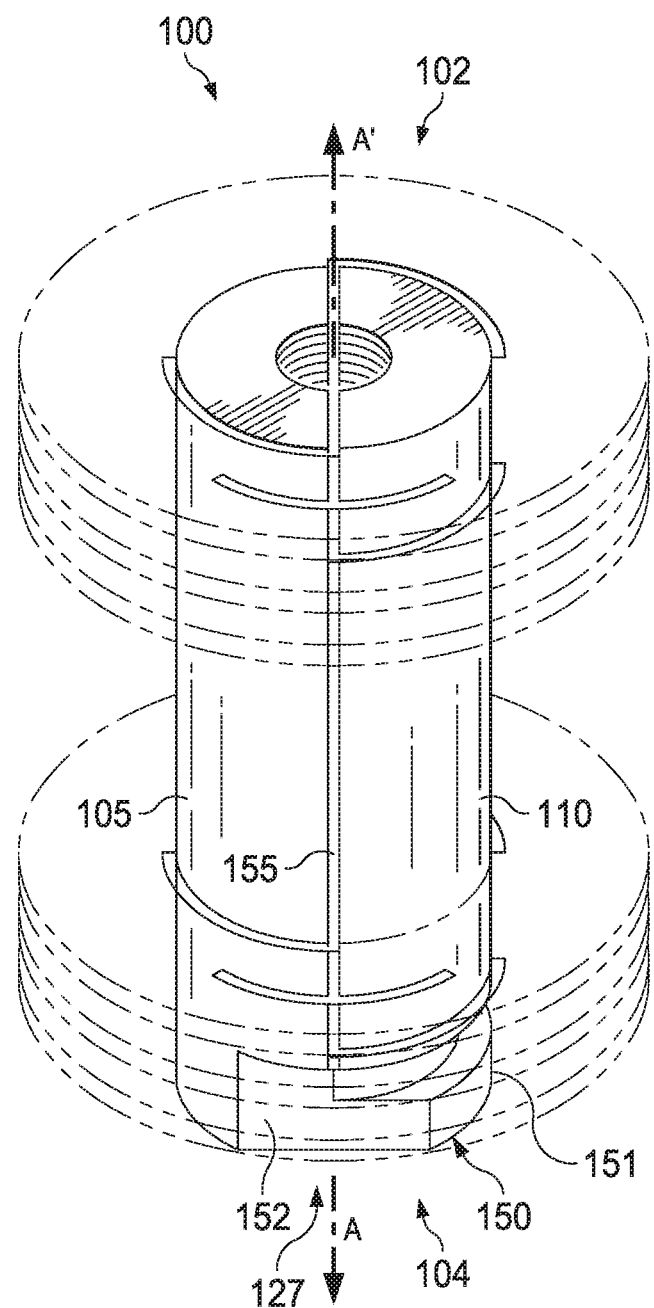
FIG. 1B illustrates another perspective view of one embodiment of a dynamization device.

An alternative view of the dynamization device 100 is depicted in FIG. 1B, where the deformable rings are shown with hatched lines to see more of the structure of the first and second modules 105, 110. As shown in FIG. 1B, the first and second modules 105, 110 have generally cylindrical shapes that are coaxial with the longitudinal axis A-A' of the dynamization device 100. Other shapes may be utilized so long as the outer longitudinal surfaces of the modules 105, 110 are smooth, so as to permit the longitudinal displacement of the first module 105 with respect to the second module 110, and vice versa. A stopping member 150 is depicted in FIG. 1B as radially protruding from the second end 104 of the first module 105. As shown in FIG. 1B, the stopping member 150 may protrude radially from the second end of the first module 105 so that its outer edge 151 is generally aligned with the outer wall of the second module 110. The stopping member 150 may further comprise one or more chordal surfaces 152, which form a flattened surface at the second end 104 of the first module 105. According to one embodiment, the chordal surfaces 152 may be found in a pair that are radially positioned opposite each other and can be used to hold the device 100 in place as a threaded bolt, rod, or other connector is attached to the threaded aperture 127 at the second end 104 of the device. According to another embodiment, the stopping member 150 can be eliminated from the second end 104 of the first module 105. Also shown in FIG. 1B is a longitudinal gap 155 running the length of the dynamization device 100 where the first module 105 and second module 110 are mated together.

Figure 1C:
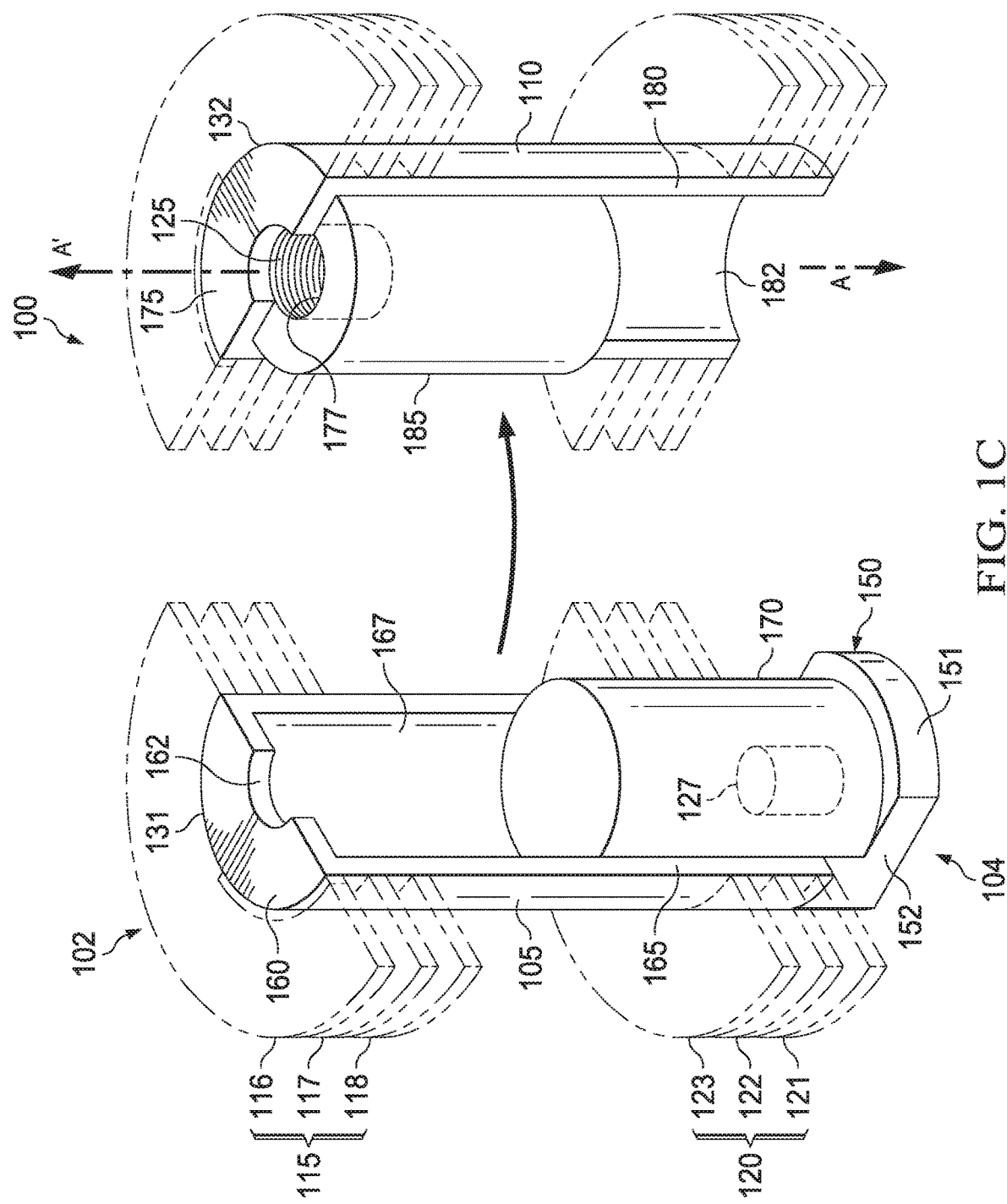
FIG. 1C illustrates an exploded view of one embodiment of a dynamization device.

An exploded view of the representative embodiment of FIG. 1A is depicted in FIG. 1C. In FIG. 1C, the first module 105 has been unmated from the second module 110 to illustrated the inner components of these modules. The first module 105 includes a semicircular cap 160 located at a first end 102. The semicircular cap 160 may comprise a central aperture 162 that is coaxial with the longitudinal axis A-A'. According to one embodiment, the central aperture 162 allows a threaded bolt, rod, or other connector to pass through the semicircular cap 160 to connect to the threaded aperture 125 in the second module 110. The first module 105 further comprises an outer wall 165 that preferably has a substantially cylindrical shape. The outer wall 165 also includes a smooth inner surface 167 at the first end 102. Also depicted in FIG. 1C is an inner column 170 located at a second end 104 of the first module 105. The inner column 170 preferable has a substantially cylindrical shape, but other surfaces may be used, so long as they have a smooth longitudinal surface. The outside surface of the inner column 170 is preferably of substantially the same radial distance as the inner surface 167. The inner column 170 may further comprise a threaded recess 127 at the second end 104. The threaded recess 127 allows a threaded bolt, rod, or other connector to be connected to a second end 104 of the dynamization device 100. Also shown in FIG. 1C is the stopping member 150 that radially protrudes from the second end 104 of the first module 105. The stopping member 150 may further comprise one or more chordal surfaces 152, which form a flattened surface at the second end 104 of the first module 105. According to one embodiment, the chordal surfaces 152 may be found in a pair that are radially positioned opposite each other and can be used to hold the dynamization device 100 in place as a threaded bolt, rod, or other connector is attached to the threaded aperture 127 at the second end 104 of the device. According to one embodiment, the outer wall 165, the central aperture 162, the threaded recess 127, and the inner column 170 are substantially coaxial with the longitudinal axis A-A' of the dynamization device 100.

As shown in FIG. 1C, the second module 110 includes a semicircular cap 175 located at a first end 102 of the dynamization device 100. The semicircular cap 175 may comprise a central aperture 177 that is coaxial with the longitudinal axis A-A'. Also depicted in FIG. 1C is the threaded recess 125, which allows a threaded bolt, rod, or other connector to be connected to a first end 102 of the device 100. The second module 110 further comprises an outer wall 180 that preferably has a substantially cylindrical shape. The outer wall 180 also includes a smooth inner surface 182 at the second end 104. The inner surface 182 of the outer wall 180 in the second module 110 is preferably arranged to mate with the outer surface of the inner column 170 of the first module 105. Also depicted in FIG. 1C is an inner column 185 located at the first end 102 of the second module 110. The inner column 185 preferable has a substantially cylindrical shape, but other surfaces may be used, so long as they have a smooth longitudinal surface. The outer surface of the inner column 185 in the second module 110 is preferably arranged to mate with the inner surface 167 of the outer wall 165 of the first module 105. The outside surface of the inner column 185 is preferably of substantially the same radial distance as the inner surface 182 of the outer wall 180. The inner column 185 may further comprise the threaded recess 125 located at the first end 102 of second module 110. The second end 104 of the second module 110 preferably includes no stopping member or semicircular cap. Rather, it is preferred that the second end 104 of the second module 110 remain open. The first and second sets of deformable rings 115, 120 are depicted in hatched lines in FIG. 1C, but are intended to be connected to the first and second modules 105, 110 as described below.

Figure 1D:
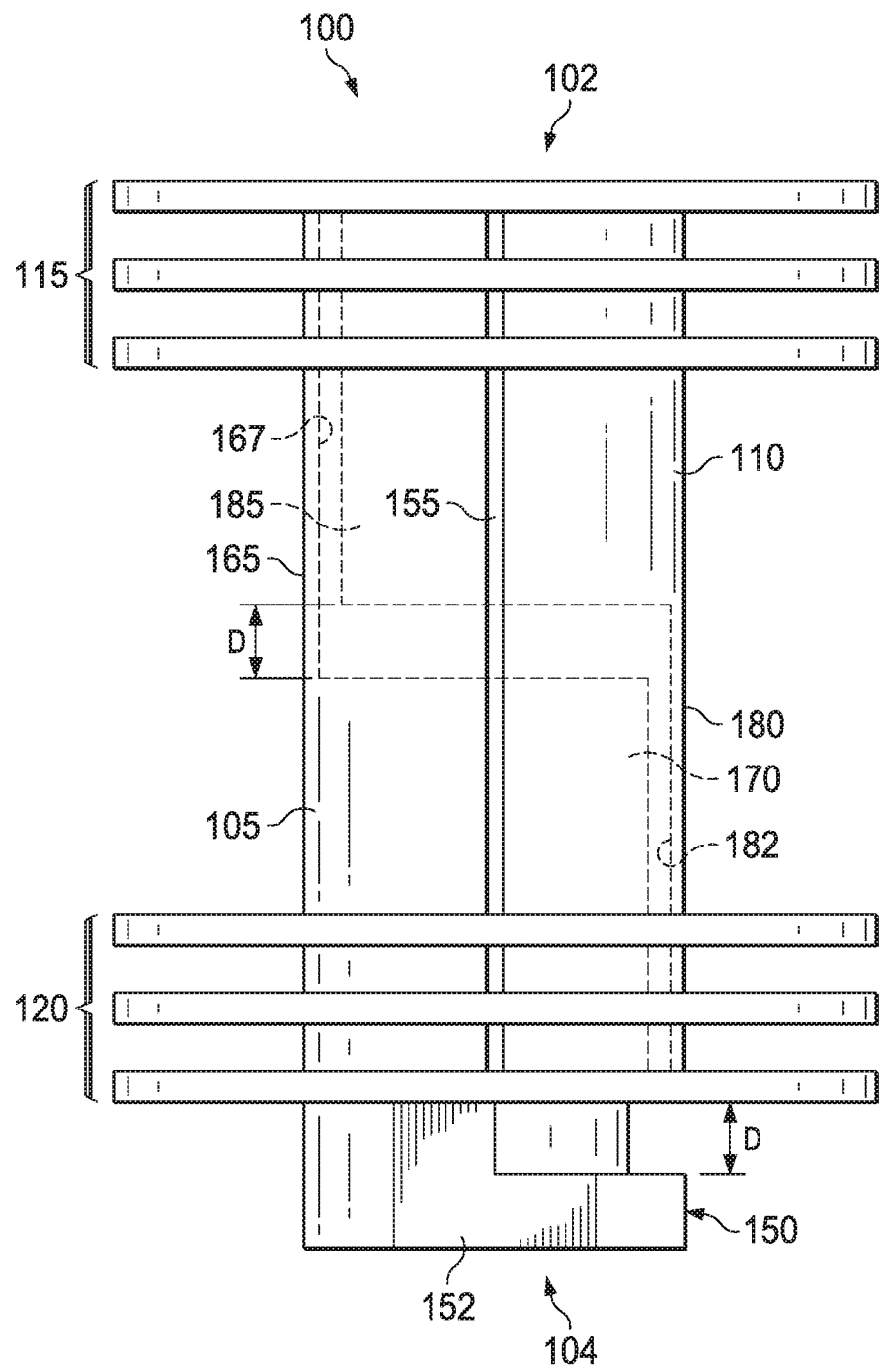
FIG. 1D illustrates a side view of one embodiment of a dynamization device.

A side view of the representative device 100 of FIG. 1A is depicted in FIG. 1D. In FIG. 1D, the device 100 is shown as viewed from the side. The first module 105 and the second module 110 are mated together so that the inner column 170 of the first module 105 mates with the inner surface 182 of the outer wall 180 of the second module 110. Similarly, the inner column 185 of the second module 110 mates with the inner surface 167 of the outer wall 165 of the first module 105. FIG. 1D also illustrates that a displacement distance D is located between the inner column 170 of the first module and the inner column 185 of the second module. Displacement distance D is also found between the second end 104 of the second module 110 and the upper surface of the stopping member 150. These displacement distances are preferably substantially the same and are preferably in the range of about 1-3 mm, with a preferred maximum of about 3 mm. As a result, when the first module 105 is longitudinally compressed towards the second module 110, the inner columns 170, 185 and the stopping member 150 will stop the displacement at the same position. During this longitudinal compression, the rings (116-123) are deformed, thus creating a mechanical bias that causes the device 100 to return to its original position when the longitudinal force is removed. The device 100 is designed such that longitudinal distraction is preferably not allowed. Specifically, the semicircular cap 160 at the first end 102 of the first module 105 prevents the inner column 185 of the second module 110 from being longitudinally displaced away from the inner column 170 of the first module 105. This limits device 100 to providing longitudinal compression, but not longitudinal distraction.

Either of the inner columns 170, 185 and/or the stopping member 150 can be eliminated from the device consistent with the spirit of this invention. The deformable rings 115, 120 and the longitudinal gap 155 are also depicted in FIG. 1D. Also shown in FIG. 1D is the stopping member 150 that radially protrudes from the second end 104 of the first module 105. The stopping member 150 may further comprise one or more chordal surfaces 152, which form a flattened surface at the second end 104 of the first module 105. According to one embodiment, the chordal surfaces 152 may be found in a pair that are radially positioned opposite each other and can be used to hold the device 100 in place as a threaded bolt, rod, or other connector is attached to the threaded aperture 127 at the second end 104 of the device. According to one embodiment, the outer wall 165, the central aperture 162, the threaded recess 127, and the inner column 170 are substantially coaxial with the longitudinal axis A-A' of the device 100.

In an embodiment in which the stopping member 150 is eliminated from the second end 104 of the first module 105, the longitudinal displacement of the first module 105 with respect to the second module 110 is halted when the inner column 170 of the first module 105 is pressed against the inner column 185 of the second member 110.

Figure 1E:
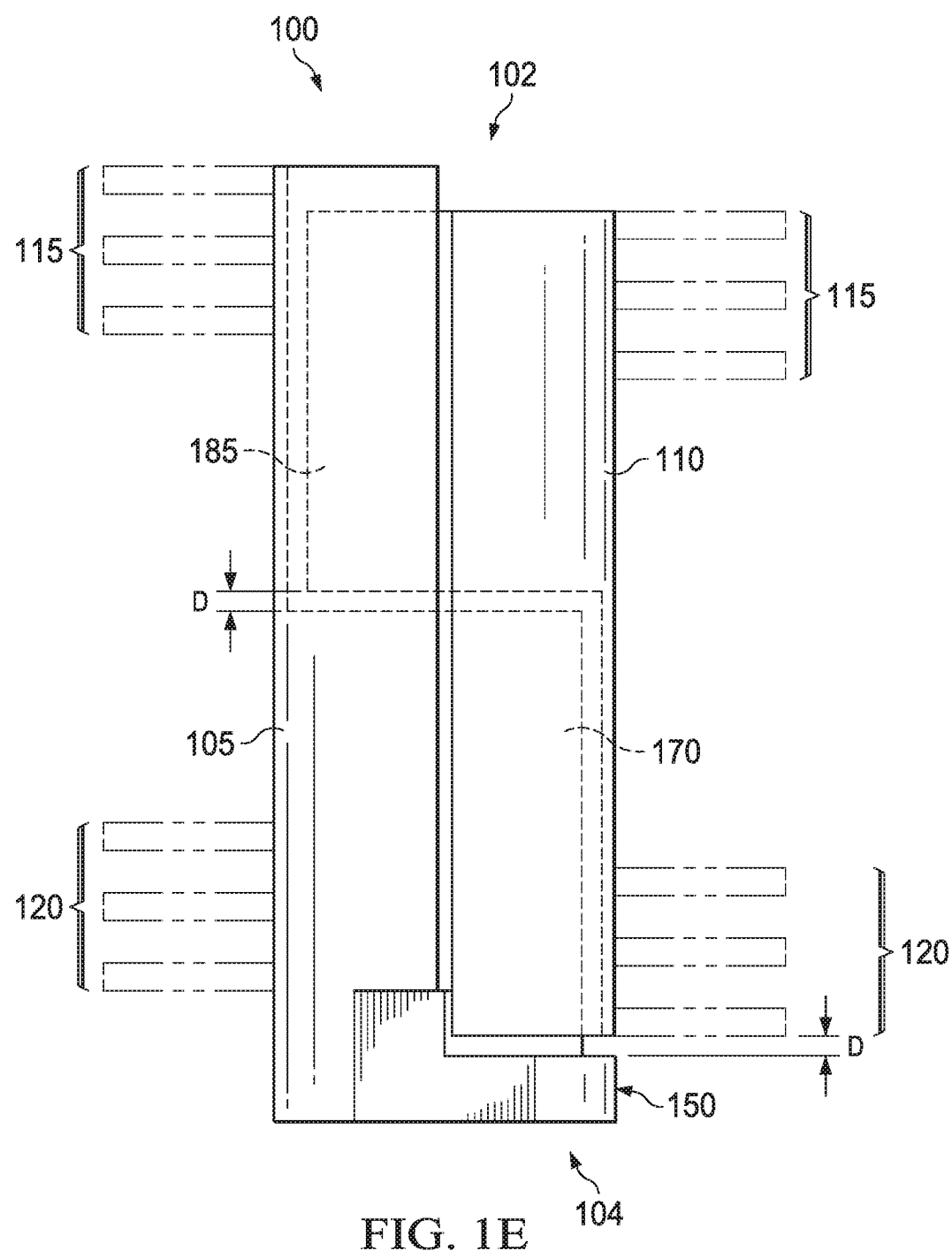
FIG. 1E illustrates a side view of one embodiment of a dynamization device.

Another representative side view of the device 100 is depicted in FIG. 1E. In FIG. 1E, the device 100 is again shown as viewed from the side, but the second module 110 has been longitudinally displaced towards the second end 104 with respect to the first module 105. As a result, the displacement distance D is much smaller. As mentioned above, the displacement distance D can be varied depending on the need for longitudinal displacement, e.g., when used in distraction of a leg bone the distance may be larger that distraction of an arm bone. As a result, when the first module 105 is longitudinally displaced with respect to the second module 110, the inner columns 170, 185 will prevent any lateral displacement, and the stopping member 150 will stop the longitudinal displacement at the same position. As the first module 105 is longitudinally displaced with respect to the second module 110, the set of first deformable rings 115 are displaced with respect to each other. As depicted in FIG. 1E (with hatched lines), the first deformable rings 115 are held in contact with the first module 105 and the second module 110 by their respective ring connectors as those modules are longitudinally displaced with respect to each other. This deforms the shape of the first deformable rings 115 so that a longitudinal mechanical bias is applied between the first and second modules 105, 110 to return the first deformable rings to their original position. Similarly, at the second end 104 of the device 100, as the first module 105 is longitudinally displaced with respect to the second module 110, the set of second deformable rings 120 are displaced with respect to each other. As depicted in FIG. 1E (with hatched lines), the second deformable rings 120 are held in contact with the first module 105 and the second module 110 by their respective ring connectors as those modules are longitudinally displaced with respect to each other. This deforms the shape of the second deformable rings 120 so that a longitudinal mechanical bias is applied between the first and second modules 105, 110 to return the first deformable rings to their original position. These longitudinal mechanical biases return the device to its original position when the longitudinal force is removed from the device 100.

Figure 1F:
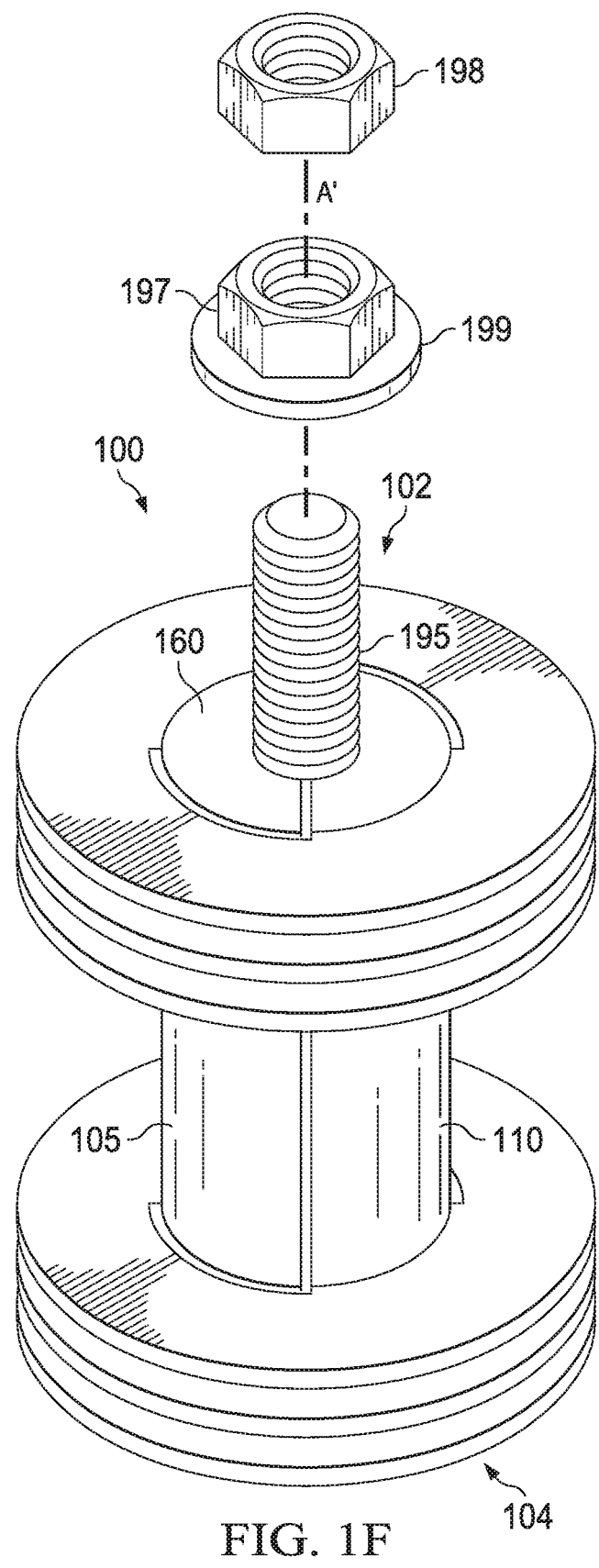
FIG. 1F illustrates a perspective view of one embodiment of a dynamization device with a locking device.

A threaded fastener 197 suitable for use with the device 100 is depicted in FIG. 1F. In FIG. 1F, the threaded fastener 197 can be threaded onto a threaded rod 195 disposed at a first end 102 of the device 100. Preferably, the threaded fastener 197 includes a flange 199 with a wider radius than the fastener 197 to increase the surface area for contacting the semicircular cap 160 of the first module 105. As described with reference to FIG. 1C, the threaded rod 195 attaches to the threaded recess 125 within the second inner column 185 of the second module 110, but does not attach to the semicircular cap 160 of the first module 105. In this manner, applying a compressive longitudinal force to the threaded rod 195 causes the second module 110 to longitudinally displace with respect to first module 105, as shown in FIG. 1E. When the threaded fastener 197 is placed adjacent to the first end 102 of the device 100, the flange 199 prevents the first module 105 from longitudinally displacing with respect to the second module 110 because it remains in contact with the semicircular cap 160. This substantially prevents compressive longitudinal movement of the device 100. According to one embodiment, an additional locking nut 198 can be threaded onto the threaded rod 195 to further secure the placement of the threaded fastener 197 against the first end 102 of the device 100. Controlled amounts of dynamization can be imparted to the device 100 by backing the threaded fastener 197 (and the locking nut 198, if present) away from the first end 102. For example, if only a limited amount of dynamization is desired, such as at the beginning of a therapeutic regimen, then the threaded fastener 197 can be backed away from the first end 102 of the dynamization device 100 by a controlled amount (e.g., one quarter turn, one half turn, one full turn, etc.). In this manner, the surgeon or medical technician can gradually apply increasing amounts of dynamization to the device and to the patient, consistent with the therapeutic regimen. The additional locking nut 198 can be tightened against the threaded fastener 197 to ensure that the amount of dynamization is fixed and does not change during the therapeutic process. It is contemplated that a variety of different threaded fasteners and locking nuts (e.g., nuts, flanged nuts, plates, washers, etc.) can be used to control the amount of dynamization provided by the device 100, consistent with this description.

Figure 2A:
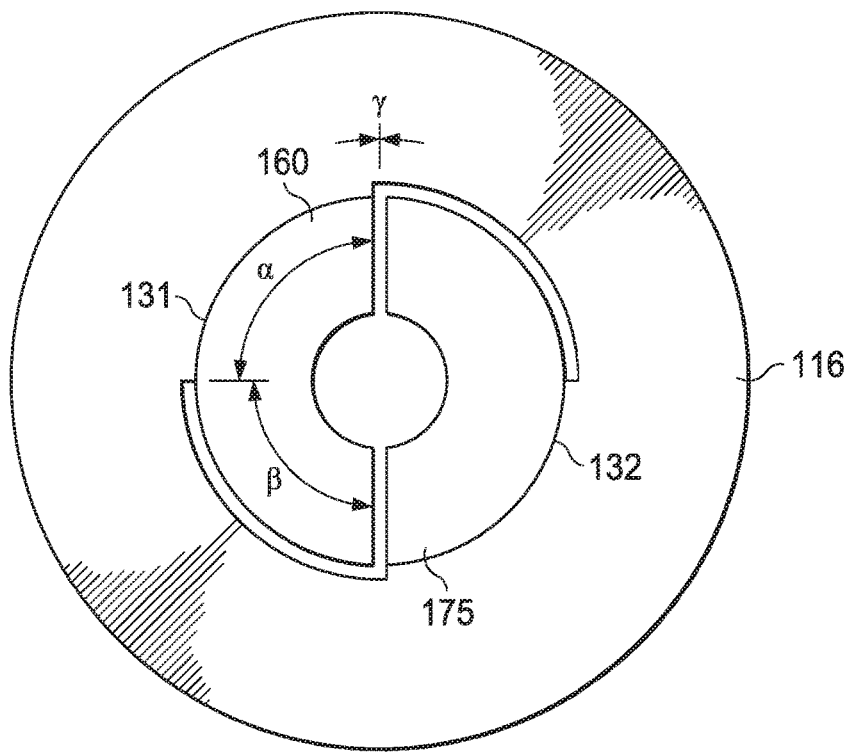
FIG. 2A illustrates a top view of one embodiment of a deformable ring for use with a dynamization device.
Figure 2B:
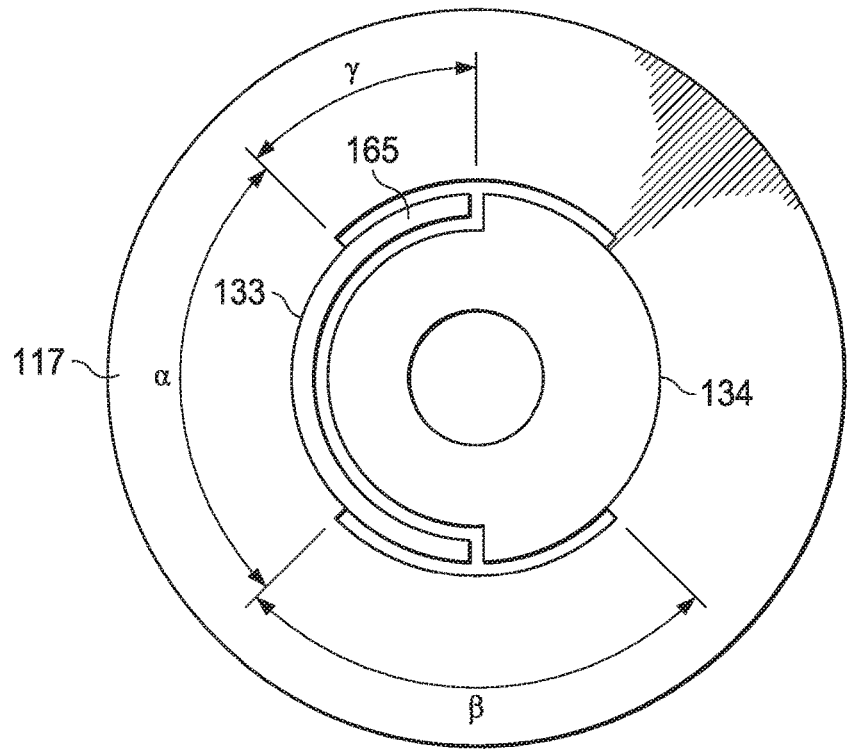
FIG. 2B illustrates a top view of one embodiment of a deformable ring for use with a dynamization device.
Figure 2C:
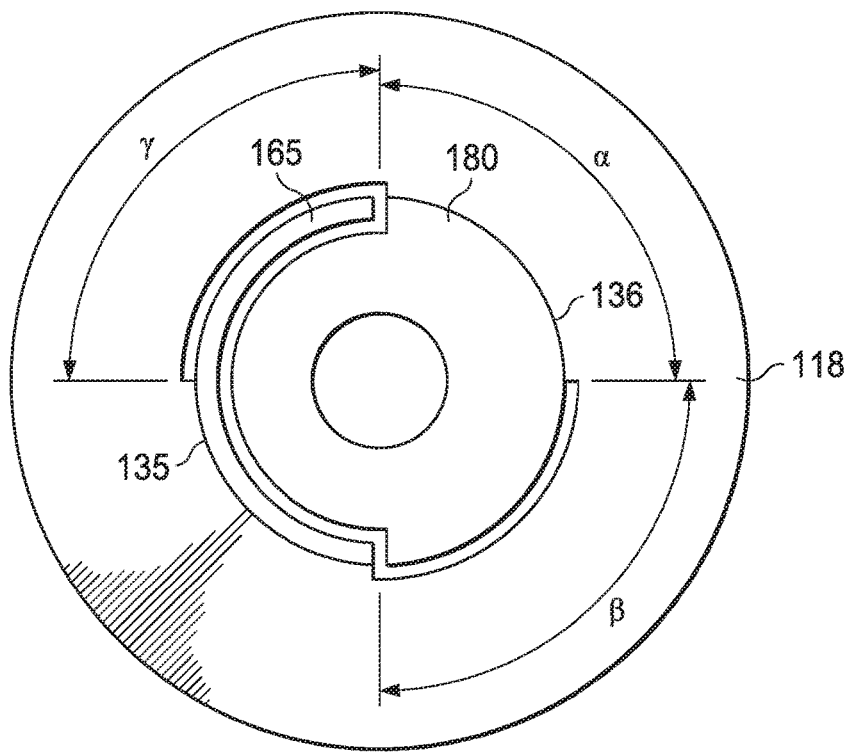
FIG. 2C illustrates a top view of one embodiment of a deformable ring for use with a dynamization device.

A representative embodiment of the first deformable rings 115 is found in FIGS. 2A-2C. In FIG. 2A, a top view of a representative a first deformable ring 116 is shown. As mentioned previously, the first deformable ring 116 can be positioned at a first end 102 of the first and second modules 105, 110 and connected to a portion the outer wall of the first module 160 and connected to a portion of the outer wall of the second module 175 by first ring connectors 131, 132 that are radially positioned opposite each other. According to some embodiments, the first ring connectors 131, 132 connect to the first and second modules 105, 110 through about 90° of angular space (α), while leaving unconnected about 90° of angular space (β). The unconnected sections of the first deformable ring 116 allow the ring to deform and flex when the first and second modules 105, 110 are longitudinally displaced, with respect to each other.

In FIG. 2B, a top view of a representative second deformable ring 117 is shown. As mentioned previously, the second deformable ring 117 can be longitudinally displaced from the first deformable ring and connected to a portion the outer wall 165 of the first module 105 and connected to a portion of the outer wall 180 of the second module 110 by second ring connectors 133, 134 that are radially positioned opposite each other. According to some embodiments, the second ring connectors 133, 134 connect to the first and second modules 105, 110 through about 90° of angular space (α), while leaving unconnected about 90° of angular space (β). The unconnected sections of the second deformable ring 117 can deform and flex when the first and second modules 105, 110 are longitudinally displaced with respect to each other. Moreover, the greater the degree to which the deformable rings are connected to the first and second modules (e.g., 120°, 130°, 60°, 45°) can affect the strength of the device, as well as the desired spring coefficient to be provided by the device when the first and second modules are displaced. In addition, the materials from which the various components are formed can also affect the longitudinal and lateral displacement o the device 100. The preferred embodiment of the ring connectors uses connections through about 90° of angular space, while leaving about 90° unconnected. The radial position of the second ring connectors 133, 134 can be angularly shifted (γ) by 45°, when compared to the radial position of the first ring connectors 131, 132. The degree of the shift of the radial position (γ) of adjacent ring connectors can be varied, depending upon the number of rings in the device, the amount of dynamization to be provided by the device, and the desired spring coefficient to be provided by the device when the first and second modules are longitudinally displaced.

Non-limiting examples of materials from which the device can be made include, but are not limited to, e.g., a material having appropriate elasticity and shape memory, such material can be selected from plastic, polymer, thermoplastic, metal, metal alloy, composite, resin, ultra-high-molecular-weight polyethylene (UHMW), a polytetrafluoroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. In certain non-limiting examples the polymer can be a thermoplastic polymer, a polyolefin, a polyester, a polysilicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a polysulfone, a polycarbonate, a polyacetal, poly(hydroxynapthoic acid), a conductive polymer, a poly(3-hexylthiophene), a polyphenylene-vinylene, a poly(phenylene vinylene), a polyaniline, or combinations thereof. Other appropriate and biocompatible materials can be utilized. According to another embodiment, the dynamization device can be fabricated by an additive printing process (e.g., a 3D printing process).

In FIG. 2C, a top view of a representative third deformable ring 118 is shown. As mentioned previously, the third deformable ring 118 can be longitudinally displaced from the second deformable ring and connected to a portion the outer wall 165 of the first module 105 and connected to a portion of the outer wall 180 of the second module 110 by third ring connectors 135, 136 that are radially positioned opposite each other. According to some embodiments, the third ring connectors 135, 136 connect to the first and second modules 105, 110 through about 90° of angular space (α), while leaving unconnected about 90° of angular space (β). The unconnected sections of the proximal deformable ring 118 can deform and flex when the first and second modules 105, 110 are longitudinally displaced with respect to each other. Moreover, the greater the degree to which the deformable rings are connected to the first and second modules (e.g., 120°, 130°, 60°, 45°) can affect the strength of the device, as well as the desired spring coefficient to be provided by the device when the first and second modules are displaced. The preferred embodiment of the ring connectors uses connections through about 90° of angular space (α), while leaving about 90° of angular space (β) unconnected. The radial position of the third ring connectors 135, 136 can be angularly shifted (γ) by 45°, when compared to the radial position of the second ring connectors 133, 134. The degree of the shift of the radial position (γ) of adjacent ring connectors can be varied, depending upon the number of rings in the device, the amount of dynamization to be provided by the device, and the desired spring coefficient to be provided by the device when the first and second modules are displaced. By evenly spacing the degree of the shift of the radial position (γ) of the first set of deformable rings (115), the lateral and torsional loads applied to the device 100 by the deformation of the rings will largely cancel each other, thus resulting in nearly all of the mechanical bias being applied in a longitudinal direction.

Figure 2D:
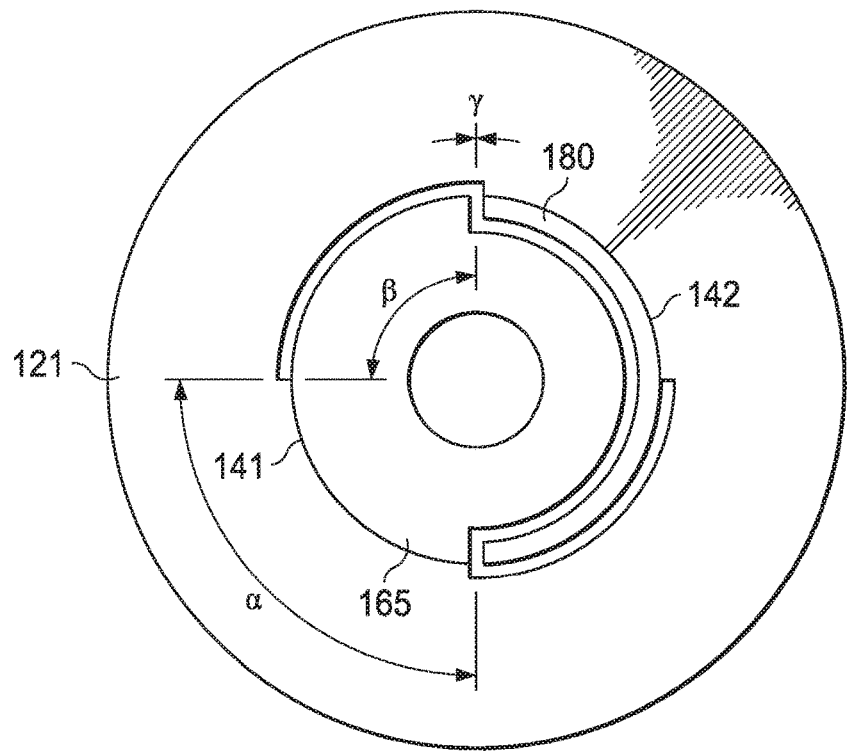
FIG. 2D illustrates a top view of one embodiment of a deformable ring for use with a dynamization device.
Figure 2E:
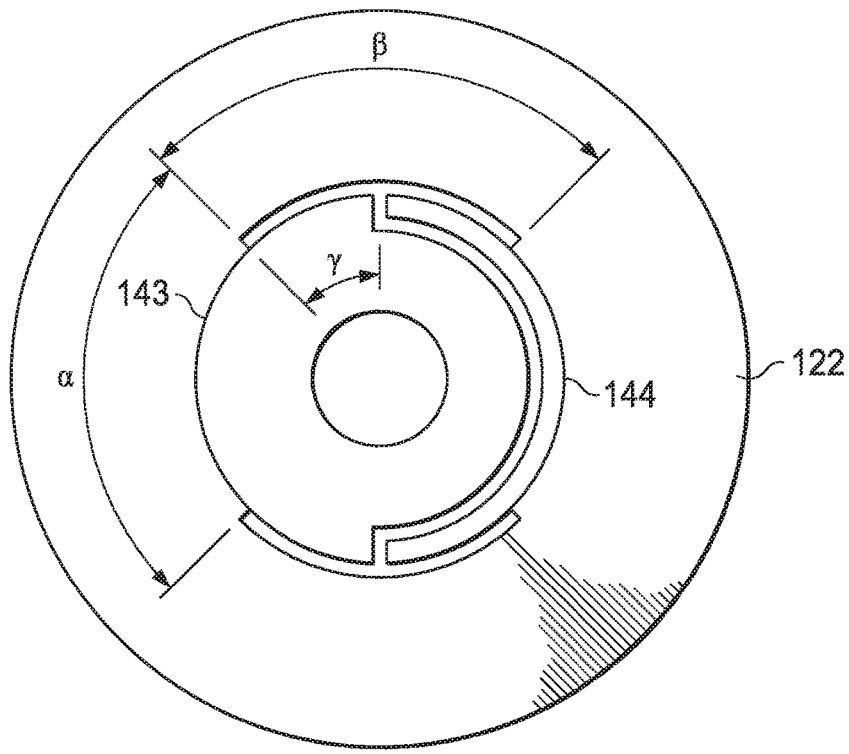
FIG. 2E illustrates a top view of one embodiment of a deformable ring for use with a dynamization device.
Figure 2F:
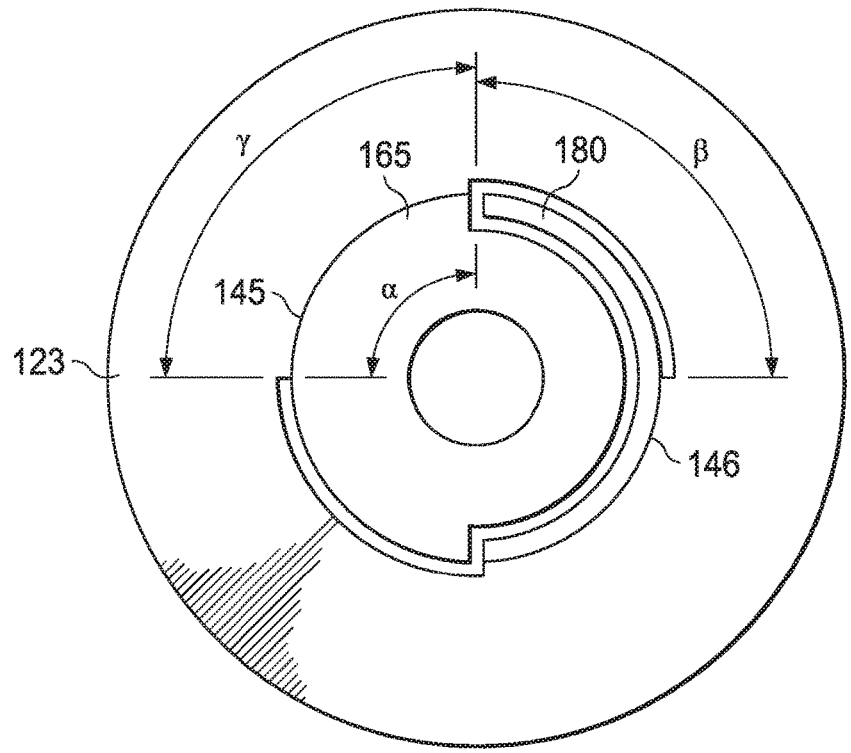
FIG. 2F illustrates a top view of one embodiment of a deformable ring for use with a dynamization device.

A representative embodiment of the second deformable rings 120 is found in FIGS. 2D-2F. In FIG. 2D, a top view of a representative a fourth deformable ring 121 is shown. The fourth deformable ring 121 can be positioned at a second end 104 of the first and second modules 105, 110 and connected to a portion the outer wall 165 of the first module 105 by fourth ring connector 141. The fourth deformable ring 121 can also be connected to a portion of the outer wall 180 of the second module 110 by fourth ring connector 142. It is preferable that the fourth ring connectors 141, 142 are radially positioned opposite each other. According to some embodiments, the fourth ring connectors 141, 142 connect to the first and second modules 105, 110 through about 90° of angular space (α), while leaving unconnected about 90° of angular space (β). The unconnected sections of the fourth deformable ring 121 allow the ring to deform and flex when the first and second modules 105, 110 are longitudinally displaced, with respect to each other.

In FIG. 2E, a top view of a representative fifth deformable ring 122 is shown. As mentioned previously, the fifth deformable ring 122 can be longitudinally displaced from the fourth deformable ring 121 and connected to a portion the outer wall 165 of the first module 105 and connected to a portion of the outer wall 180 of the second module 110 by fifth ring connectors 143, 144 that are radially positioned opposite each other. According to some embodiments, the fifth ring connectors 143, 144 connect to the outer walls of the first and second modules 105, 110 through about 90° of angular space (α), while leaving unconnected about 90° of angular space (β). The unconnected sections of the fifth deformable ring 122 can deform and flex when the first and second modules 105, 110 are longitudinally displaced with respect to each other. Moreover, the greater the degree to which the deformable rings are connected to the first and second modules (e.g., 120°, 130°, 60°, 45°) can affect the strength of the device, as well as the desired spring coefficient to be provided by the device when the first and second modules are longitudinally displaced. The preferred embodiment of the ring connectors uses connections through about 90° of angular space, while leaving about 90° unconnected. The radial position of the fifth ring connectors 143, 144 can be angularly shifted (γ) by 45°, when compared to the radial position of the fourth ring connectors 141, 142. The degree of the shift of the radial position (γ) of adjacent ring connectors can be varied, depending upon the number of rings in the device, the amount of dynamization to be provided by the device, and the desired spring coefficient to be provided by the device when the first and second modules are longitudinally displaced.

In FIG. 2F, a top view of a representative sixth deformable ring 123 is shown. As mentioned previously, the sixth deformable ring 123 can be longitudinally displaced from the fifth deformable ring 122 and connected to a portion the outer wall 165 of the first module 105 and connected to a portion of the outer wall 180 of the second module 110 by sixth ring connectors 145, 146 that are radially positioned opposite each other. According to some embodiments, the sixth ring connectors 145, 146 connect to the first and second modules 105, 110 through about 90° of angular space (α), while leaving unconnected about 90° of angular space (β). The unconnected sections of the sixth deformable ring 123 can deform and flex when the first and second modules 105, 110 are longitudinally displaced with respect to each other. Moreover, the greater the degree to which the deformable rings are connected to the first and second modules (e.g., 120°, 130°, 60°, 45°) can affect the strength of the device, as well as the desired spring coefficient to be provided by the device when the first and second modules are displaced. The preferred embodiment of the ring connectors uses connections through about 90° of angular space (α), while leaving about 90° of angular space (β) unconnected. The radial position of the sixth ring connectors 145, 146 can be angularly shifted (γ) by 45°, when compared to the radial position of the fifth ring connectors 143, 144. The degree of the shift of the radial position (γ) of adjacent ring connectors can be varied, depending upon the number of rings in the device, the amount of dynamization to be provided by the device, and the desired spring coefficient to be provided by the device when the first and second modules are displaced. By evenly spacing the degree of the shift of the radial position (γ) of the second set of deformable rings (120), the lateral and torsional loads applied to the device 100 by the deformation of the rings will largely cancel each other, thus resulting in nearly all of the mechanical bias being applied in a longitudinal direction.

Figure 3:
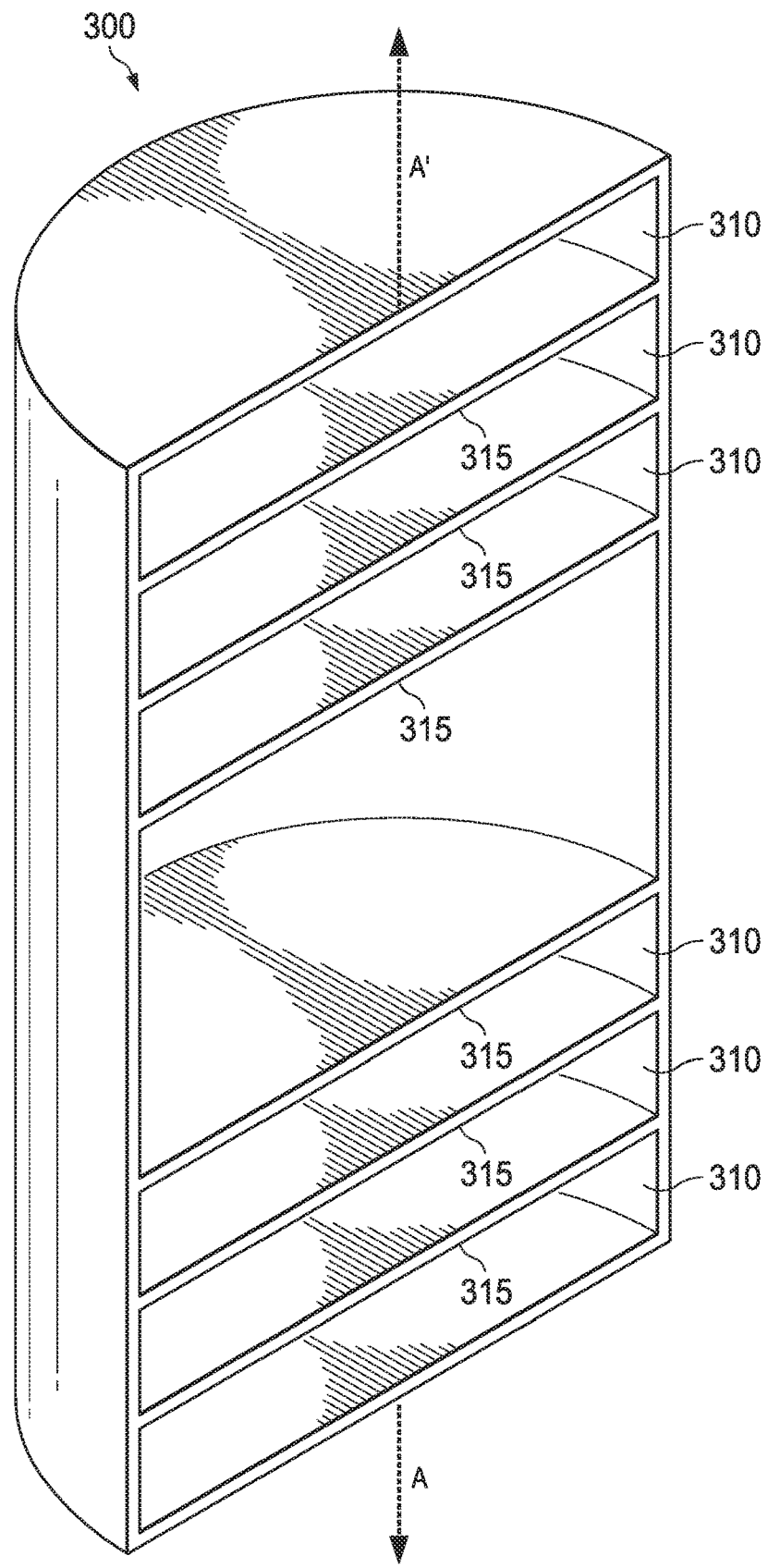
FIG. 3 illustrates a perspective view of one embodiment of a locking device suitable for use with a dynamization device.

A representative locking device 300 is depicted in FIG. 3. In FIG. 3, the locking device 300 has a substantially cylindrical shape along a longitudinal axis A-A'. The locking device should preferably be sized larger than the outer edges of the deformable rings of the dynamization device 100 so that each of the deformable rings may be received in corresponding receptacles 310. Each of the receptacles 310 is separated by an adjoining wall 315. By placing the locking device 300 onto the dynamization device, the first and second modules are prevented from longitudinally displacing with respect to each other, thereby eliminating the dynamization feature of the dynamization device 100 of FIGS. 1A to 1F and 2A to 2F, in which the first and second deformable rings 115, 120. According to one embodiment, only one locking device 300 may be needed to lock the dynamization device 100 by placing the locking device 300 onto the dynamization device 100. The locking device 300 can be secured to the dynamization device 100 through any method known in the art, such as, e.g., screws, latches, fasteners, or other mechanical lock. According to another embodiment, two or more locking devices 300 are connected to a dynamization device 100 to fully encapsulate the device 100 and thereby prevent the first and second modules 105, 110 from longitudinally displacing with respect to each other.

An alternative embodiment of the locking device 300 depicted in FIG. 3, can be a nut or other similar threaded fastener that may be placed on a threaded bolt, rod, or connector near the end the dynamization device 100. The threaded fastener should be of sufficient width to cover the outer walls of the first and second modules 105, 110, so that when the threaded fastener is placed adjacent to an end of the dynamization device 100, the first and second modules 105, 110 are unable to longitudinally displace with respect to each other. An additional benefit of using a threaded faster as the locking device 300 is that it can permit controlled amounts of dynamization to be imparted to the device 100. For example, if only a limited amount of dynamization is desired, such as at the beginning of a therapeutic regime, then the threaded fastener can be backed away from the end of the dynamization device 100 by a controlled amount (e.g., one quarter turn, one half turn, or one full turn). The skilled artisan will recognize that the lead and pitch of the threads of a screw can be varied to adjust the length of elongation along the longitudinal axis can be varied in relation to the amount of turns on the thread. In this manner, the surgeon or medical technician can gradually apply increasing amounts of dynamization to the device, and thus to the patient, consistent with the therapeutic regimen. It is contemplated that a variety of different devices can be used to control the amount of dynamization provided by the device 100, consistent with this description.

Figure 4A:
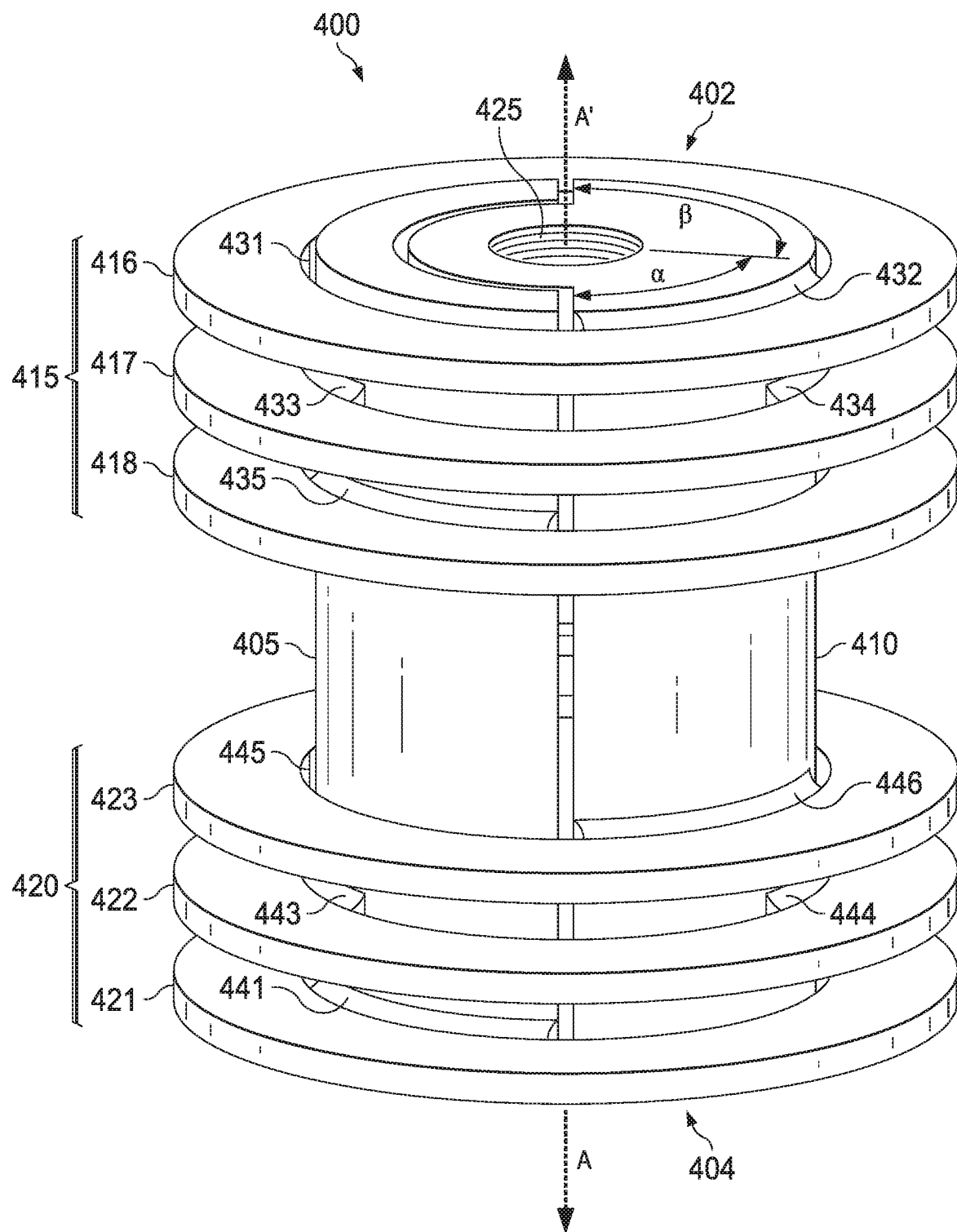
FIG. 4A illustrates a perspective view of one embodiment of a dynamization device.

Another representative embodiment of a dynamization device 400 is depicted in FIG. 4A. In FIG. 4A, a dynamization device 400 has a generally cylindrical shape along a longitudinal axis A-A'. The dynamization device 400 is comprised of a first module 405 and a second module 410 that are mated together so that the longitudinal axis of the first module 405 is coaxial to the longitudinal axis of the second module 410 and the longitudinal axis A-A' of the dynamization device 400. Positioned at a first end 402 of the dynamization device 400 is a set of first deformable rings 415. Positioned at a second end 404 of the dynamization device 400 is a set of second deformable rings 420. In the embodiment depicted in FIG. 4A, the set of first deformable rings 115 may comprise a first deformable ring 416, a second deformable ring, 417, and a third deformable ring 418. As few as one deformable ring may be used for each set of deformable rings, and many more than three deformable rings may be used for each set of deformable rings without departing from the spirit of the invention. The set of second deformable rings 420 may similarly comprise a fourth deformable ring 421, a fifth deformable ring, 422, and a sixth deformable ring 423. Each ring is connected to a portion of the first and second modules 405, 410 by one or more ring connectors. The connection of the first deformable ring 416 to the first and second modules 405, 410 is depicted in FIG. 4A with first ring connectors 431 and 432. These ring connectors (431, 432) may occupy radial positions that are opposite each other with respect to the longitudinal axis A-A'. The connection of the second deformable ring 417 to the first and second modules 405, 410 is depicted in FIG. 4A with second ring connectors 433 and 434. These ring connectors (433, 434) may occupy radial positions that are opposite each other with respect to the longitudinal axis A-A'. In addition, connection of the third deformable ring 418 to the first and second modules 405, 410 is depicted in FIG. 4A with third ring connectors 435 and 436 (not illustrated). These ring connectors (435, 436) may occupy radial positions that are opposite each other with respect to the longitudinal axis A-A'. Although two ring connectors are depicted in FIG. 4A to connect the deformable rings to the first and second modules, a plurality of connectors can be used without departing from the spirit of the invention. Also shown in FIG. 4A is threaded aperture 425 that is located at the first end 402 of the second module 510. The threaded aperture 425 may be used to connect a threaded bolt, rod, or other connector to a first end 402 of the dynamization device 400. Not shown in FIG. 4A is another threaded aperture (427) that is located at the second end 404 of the first module 405. This other threaded aperture (427) may be used to connect a threaded bolt, rod, or other connector to the second end 404 of the dynamization device 400.

According to some embodiments, the first ring connectors 431, 432 connect to the first and second modules 405, 410 through about 60° of angular space (α), while leaving unconnected about 120° of angular space (β). The unconnected sections of the distal deformable ring 416 allow the first deformable ring 416 to deform and flex when the first and second modules 405, 410 are longitudinally displaced with respect to each other. Similarly, the second ring connectors 433, 434 connect to the first and second modules 405, 410 through about 60° of angular space (α), while leaving unconnected about 120° of angular space (β). The unconnected sections of the second deformable ring 417 allow the ring to deform and flex when the first and second modules 405, 410 are longitudinally displaced with respect to each other. In addition, the third ring connectors 435, 436 connect to the first and second modules 405, 410 through about 60° of angular space (α), while leaving unconnected about 120° of angular space (β). The unconnected sections of the third deformable ring 418 allow the ring to deform and flex when the first and second modules 405, 410 are longitudinally displaced with respect to each other.

As mentioned above, the set of second deformable rings 420 may comprise a fourth deformable ring 421, a fifth deformable ring, 422, and a sixth deformable ring 423. The connection of the fourth deformable ring 421 to the first and second modules 405, 410 is depicted in FIG. 4A with fourth ring connectors 441 and 442. These ring connectors (441, 442) may occupy radial positions that are opposite each other with respect to the longitudinal axis A-A'. The connection of the fifth deformable ring 422 to the first and second modules 405, 410 is depicted in FIG. 4A with fifth ring connectors 443 and 444. These ring connectors (443, 444) may occupy radial positions that are opposite each other with respect to the longitudinal axis A-A'. In addition, connection of the sixth deformable ring 423 to the first and second modules 405, 410 is depicted in FIG. 4A with sixth ring connectors 445 and 446. These ring connectors (445, 446) may occupy radial positions that are opposite each other with respect to the longitudinal axis A-A'.

Like the first set of deformable rings 415, the second set of deformable rings 420 may include ring connectors that connect to the first and second modules over a variety of angles. The fourth ring connectors 441, 442 of the second deformable rings 420 connect to the first and second modules 405, 410 through about 60° of angular space (α), while leaving unconnected about 120° of angular space (β). The unconnected sections of the fourth deformable ring 421 allow the ring to deform and flex when the first and second modules 405, 410 are longitudinally displaced with respect to each other. Similarly, the fifth ring connectors 443, 444 connect to the first and second modules 405, 410 through about 60° of angular space (α), while leaving unconnected about 120° of angular space (β). The unconnected sections of the fifth deformable ring 422 allow the ring to deform and flex when the first and second modules 405, 410 are longitudinally displaced, with respect to each other. In addition, the sixth ring connectors 445, 446 connect to the first and second modules 405, 410 through about 60° of angular space (α), while leaving unconnected about 120° of angular space (β). The unconnected sections of the sixth deformable ring 423 allow the ring to deform and flex when the first and second modules 405, 410 are longitudinally displaced with respect to each other.

Figure 4B:
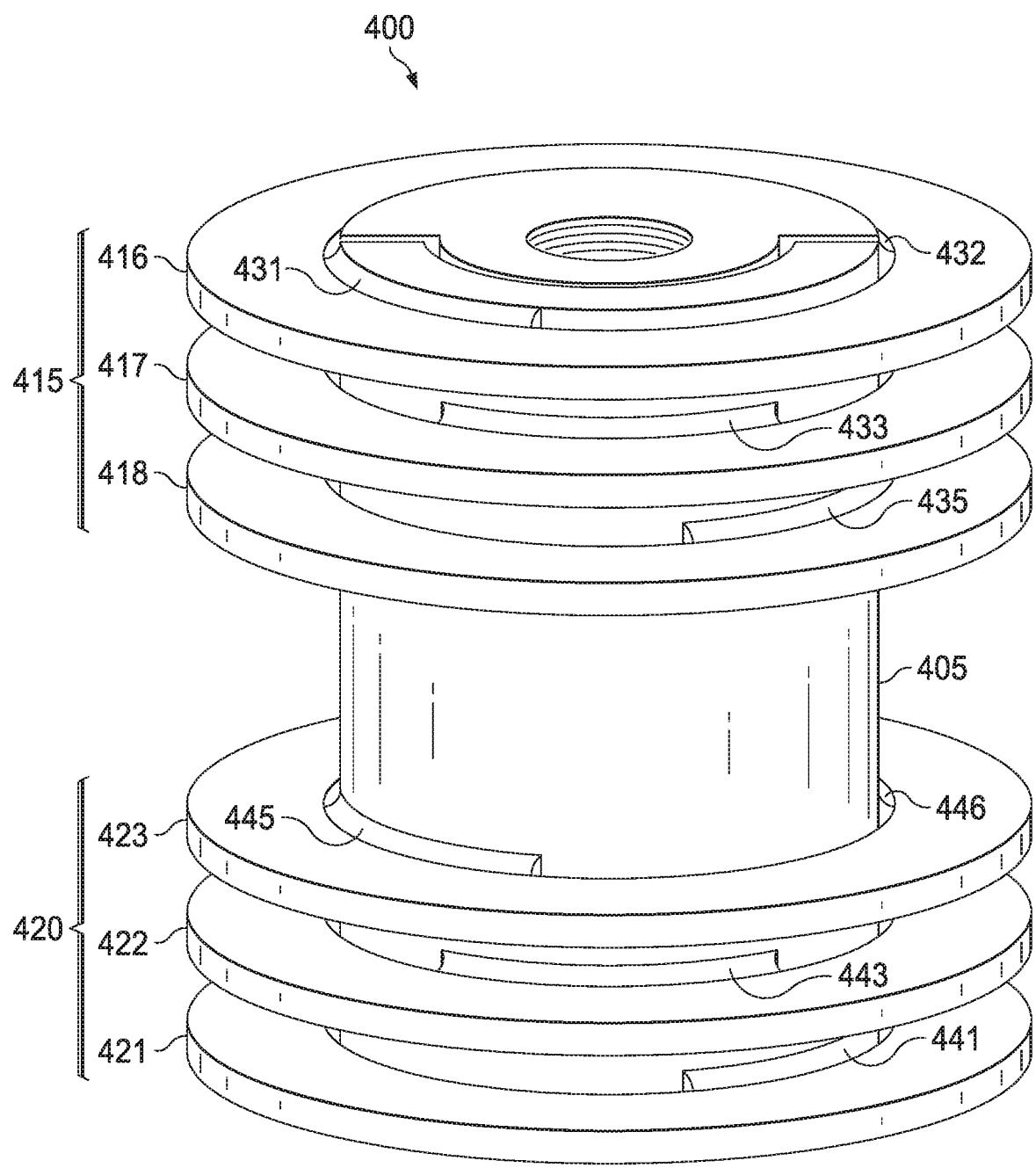
FIG. 4B illustrates a perspective view of another angle of one embodiment of a dynamization device.

Another view of the dynamization device 400 of FIG. 4A is depicted in FIG. 4B. In FIG. 4B, the dynamization device 400 has been rotated by 90° to show the same perspective, but of another side of the device 400. The first and second deformable rings (415, 420) are all visible in FIG. 4B, but the first module 405 has been rotated into view and the outer wall of the second module 410 is not visible in this figure. The ring connectors (431, 432, 433, 435 and 441, 443, 445, 446) for each of the deformable rings 415, 420, respectively, are further depicted in this view. With reference to the first deformable rings 415, the first deformable ring 416 is connected to the first and second modules 405, 410 through first ring connectors 431 and 432, respectively. The second deformable ring 417 is connected to the first and second modules 405, 410 through second ring connectors 433 and 434 (not shown), respectively. The third deformable ring 418 is connected to the first and second modules 405, 410 through third ring connectors 435 and 436 (not shown), respectively. With reference to the second set of deformable rings 420, the fourth deformable ring 421 is connected to the first and second modules 405, 410 through fourth ring connectors 441 and 442 (not shown), respectively. The fifth deformable ring 422 is connected to the first and second modules 405, 410 through fifth ring connectors 443 and 444 (not shown), respectively. The sixth deformable ring 423 is connected to the first and second modules 405, 410 through sixth ring connectors 445 and 446, respectively.

Figure 4C:
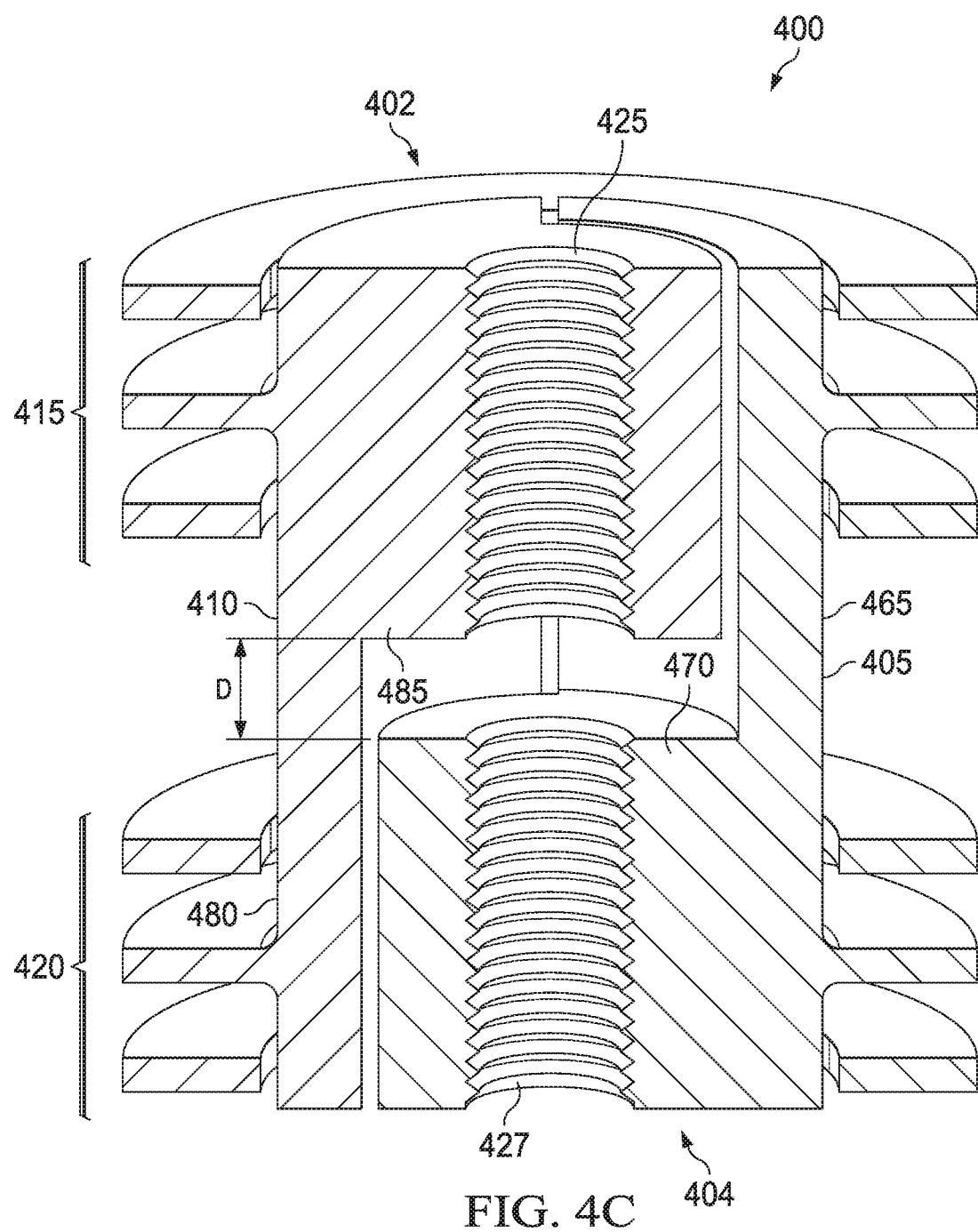
FIG. 4C illustrates a cross-sectional perspective view of one embodiment of a dynamization device.

A cross-sectional view of the representative embodiment of FIG. 4A is depicted in FIG. 4C. In FIG. 4C, the dynamization device 400 is shown with the first module 405 on the right-hand side and the second module 410 on the left-hand side. The first module 405 is depicted as having an outer wall 465 and an inner column 470. The second module 410 is depicted as having an outer wall 480 and an inner column 485. The first and second modules 405, 410 can be mated together in the same way as the embodiment of FIG. 1A-1E. Similarly, by longitudinally displacing the first module 405 with respect to the second module 410, the unconnected sections of the deformable rings (415, 420) will be deformed so as to apply a longitudinal mechanical bias to the device 400 to return it to its original position. Also depicted in FIG. 4C are threaded apertures 425 and 427, which can receive a threaded bolt, rod, or other connector at respective ends of the dynamization device 400.

Figure 4D:
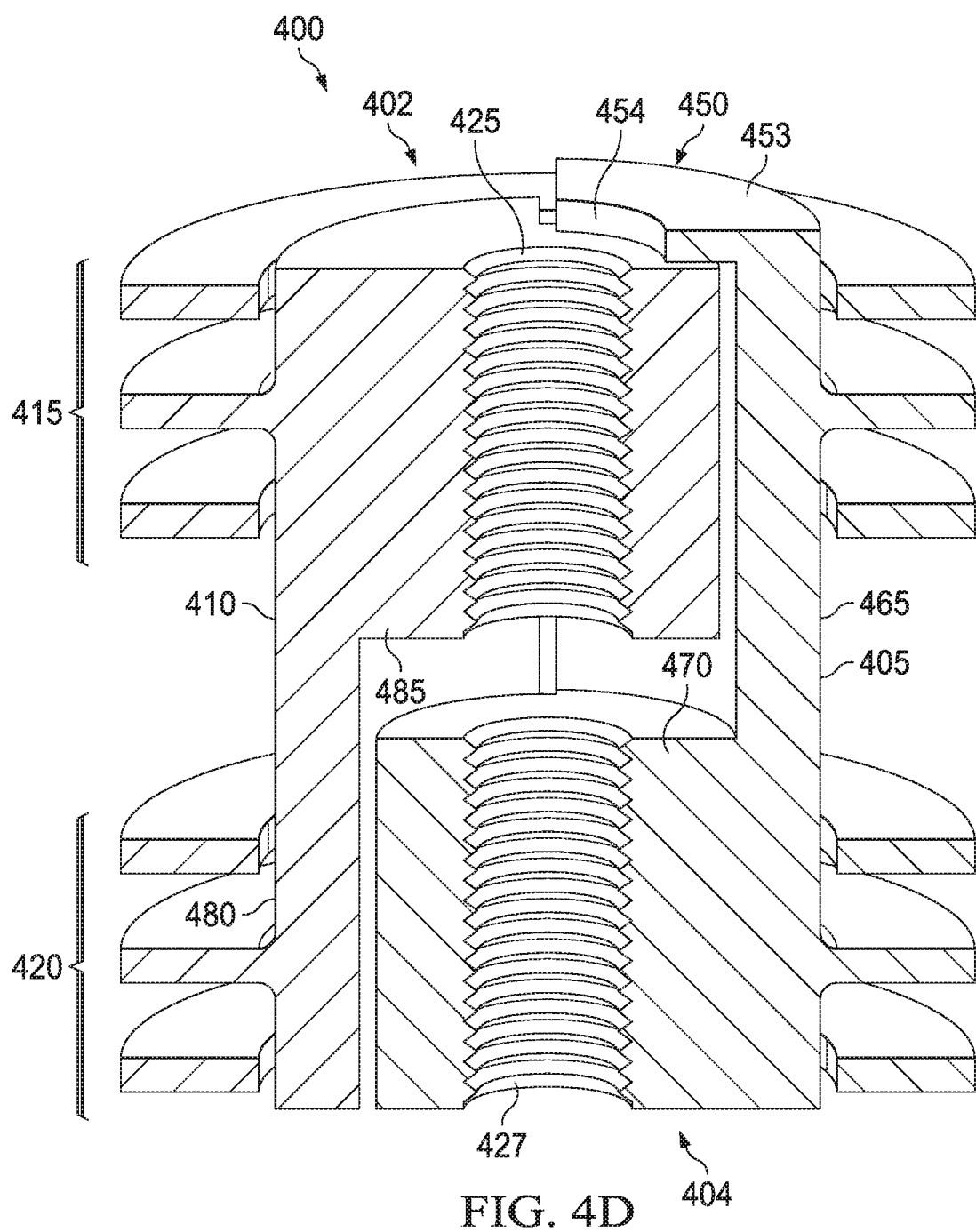
FIG. 4D illustrates a cross-sectional perspective view of an alternative embodiment of a dynamization device.

A cross sectional view of an alternative embodiment of FIG. 4A is depicted in FIG. 4D. In FIG. 4D, the dynamization device 400 is shown with the first module 405 on the right-hand side and the second module 410 on the left-hand side. Much like FIG. 4C, the first module 405 is depicted as having an outer wall 465 and an inner column 470. The second module 410 is depicted as having an outer wall 480 and an inner column 485. The first and second modules can be mated together in the same way as the embodiment of FIG. 1A-1E. Similarly, by longitudinally displacing the first module 405 with respect to the second module 410, the unconnected sections of the deformable rings (415, 420) will be deformed so as to apply a longitudinal mechanical bias to the device 400 to return it to its original position. Threaded apertures 425 and 427 can receive a threaded bolt, rod, or other connector at respective ends of the dynamization device 400. Also depicted in FIG. 4D is a stopping member 450 that protrudes from an end of the outer wall 465 of the first module 405. The stopping member 450 is depicted as an inwardly protruding lip 453 that includes an inner surface 454. The inner surface 454 must be of sufficient size to permit a threaded bolt, rod, or other connector to attach to the threaded aperture 425 at the first end 402 of the dynamization device 400. The inwardly protruding lip 453 prevents the second module 410 from longitudinally displacing away from the first module 405, thereby imparting undesirable distractive movement, instead of desirable compressive movement. Although not shown in FIG. 4D, a second stopping member can be placed at the other end of the device 400 to provide further protection against undesirable distractive movement.

Figure 4E:
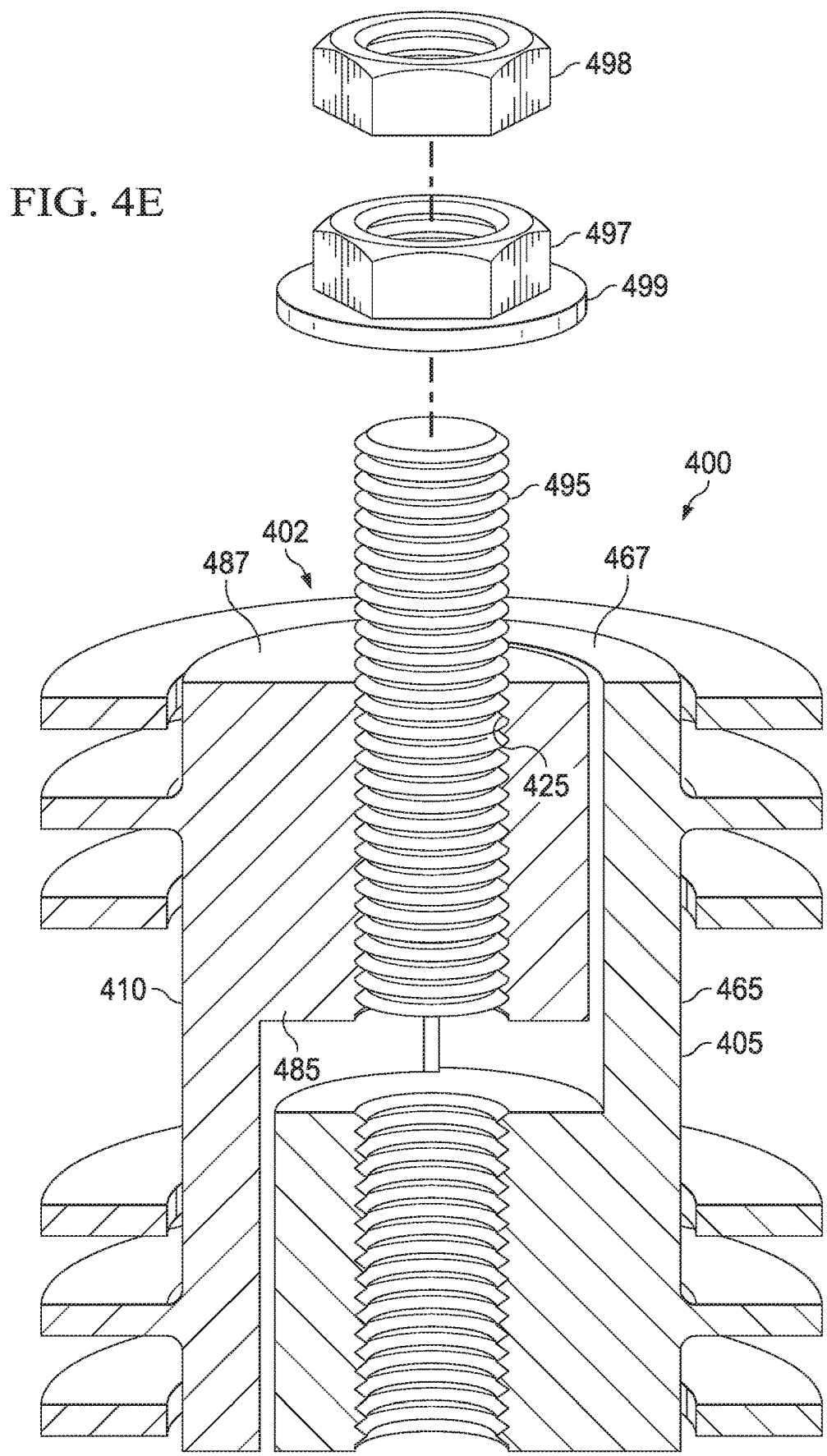
FIG. 4E illustrates a cross-sectional perspective view of an alternative embodiment of a dynamization device with a locking device.

A threaded fastener 497 suitable for use with the device 400 is depicted in FIG. 4E. In FIG. 4E, the threaded fastener 497 can be threaded on to a threaded rod 495 disposed at a first end 402 of the device 400. As described with reference to FIG. 4C, the threaded rod 495 attaches to the threaded recess 425 within the second inner column 485 of the second module 410. In this manner, applying a compressive longitudinal force to the threaded rod 495 causes the second module 410 to longitudinally displace with respect to first module 105. Preferably, the threaded fastener 497 includes a flange 499 with a radius large enough to cover both the upper surface 487 of the second inner column 485 and the upper surface 467 of the first outer wall 465, as shown in FIG. 4E. When the threaded fastener 497 is placed adjacent to the first end 402 of the device 400, the flange 499 prevents the first module 405 from longitudinally displacing with respect to the second module 410 because it remains in contact with the upper surface 467 of the first outer wall 465. This substantially prevents compressive longitudinal movement of the device 400. According to one embodiment, an additional locking nut 498 can be threaded onto the threaded rod 495 to further secure the placement of the threaded fastener 497 against the first end 402 of the device 400. Controlled amounts of dynamization can be imparted to the device 400 by backing the threaded fastener 497 (and the locking nut 498, if present) away from the first end 402. For example, if only a limited amount of dynamization is desired, such as at the beginning of a therapeutic regimen, then the threaded fastener 497 can be backed away from the first end 402 of the dynamization device 400 by a controlled amount (e.g., one quarter turn, one half turn, one full turn, etc.). In this manner, the surgeon or medical technician can gradually apply increasing amounts of dynamization to the device and to the patient, consistent with the therapeutic regimen. The additional locking nut 498 can be tightened against the threaded fastener 497 to ensure that the amount of dynamization is fixed and does not change during the therapeutic process. It is contemplated that a variety of different threaded fasteners and locking nuts (e.g., nuts, flanged nuts, plates, washers, etc.) can be used to control the amount of dynamization provided by the device 400, consistent with this description.

Figure 5A:
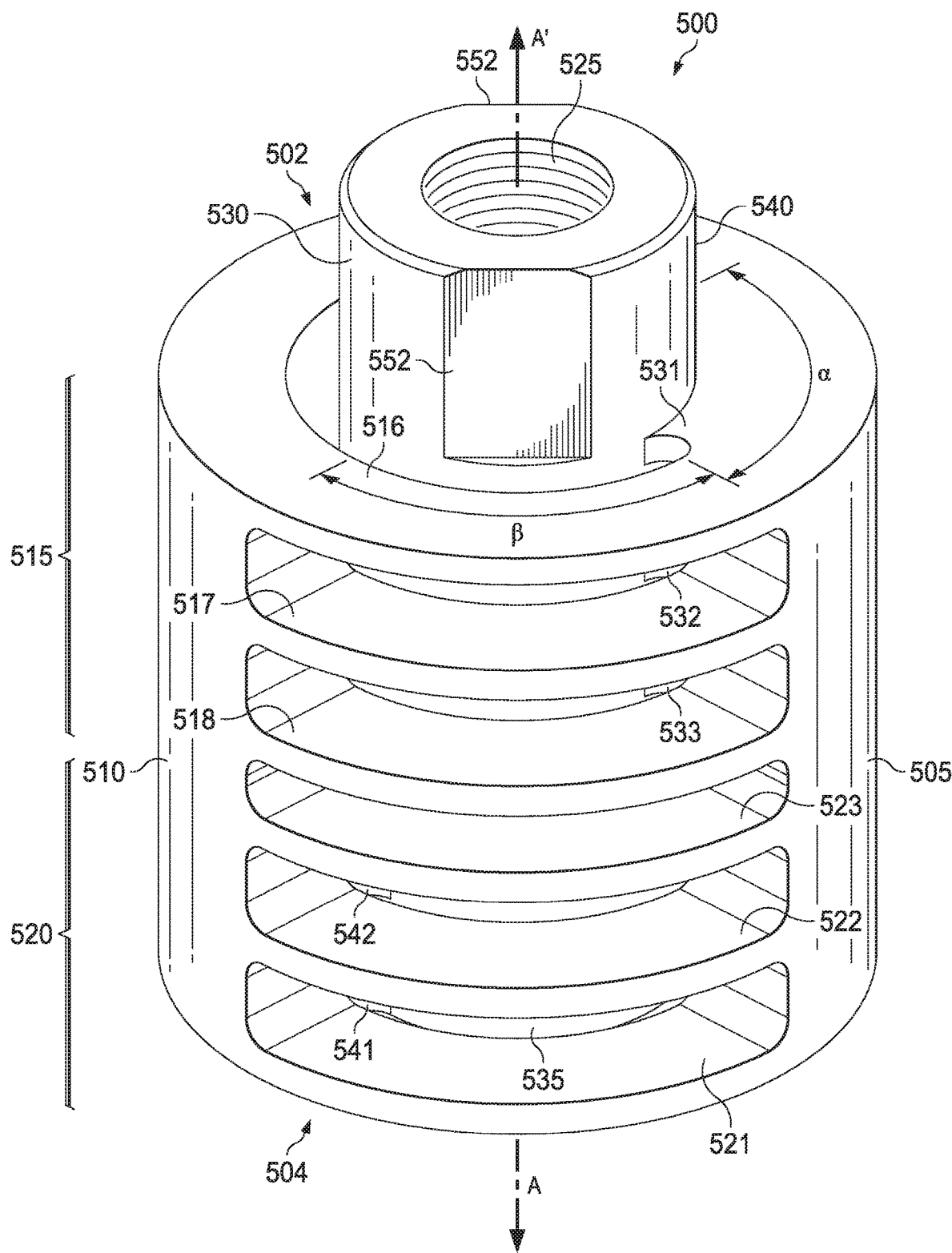
FIG. 5A illustrates a perspective view of one embodiment of a dynamization device.

An alternative embodiment of a dynamization device is depicted in FIG. 5A. In FIG. 5A, a dynamization device 500 has a generally cylindrical shape along a longitudinal axis A-A'. The dynamization device 500 is comprised of a series of deformable rings that are coaxial to the longitudinal axis A-A' of the dynamization device 500. The number of deformable rings that can be utilized in this embodiment can be as few as two, six (as shown in FIG. 5A), or many more, depending upon the desired strength, size, and degree of mechanical bias to apply during the dynamization process. As shown in FIG. 5A, six deformable rings are shown in two sets: a first set of deformable rings 515, shown more specifically as rings 516, 517, and 518, and a second set of deformable rings 520, shown more specifically as rings 521, 522, and 523. All of the rings are depicted in FIG. 5A as being connected by a first outer column 505 and a second outer column 510. This embodiment further includes a first inner column 530 that is positioned at the first end 502 of the dynamization device 500 and a second inner column 535 that is positioned at the second end 504 of the dynamization device 500. Also shown in FIG. 5A is first protrusion 540 that extends longitudinally from the first end 502 of the device 500. The first protrusion 540 includes a threaded aperture 525 to which a threaded bolt, rod, or other connector can attach to the first inner column 530 at the first end 502 of the dynamization device 500. Also shown in FIG. 5A is a pair of chordal surfaces 552, which form a flattened surface at the first end 502 of the dynamization device 500. According to one embodiment, the chordal surfaces 552 may be found in a pair that are radially positioned opposite each other and can be used to hold the dynamization device 500 in place as a threaded bolt, rod, or other connector is attached to the threaded aperture 525 at the first end 502 of the device. Also shown in FIG. 5A are two sets of ring connectors that connect the first set of deformable rings 515 and the second set of deformable rings 520 to the first inner column 530 and the second inner column 535, respectively. In FIG. 5A, the first set of deformable rings (516, 517, 518) are connected to the first inner column 530 by first, second and third ring connectors (531, 532, 533), respectively. The first, second and third ring connectors (531, 532, 533) are adjacent to the first outer column 505 to reinforce the mechanical strength of the connection between the first inner column 530 and the first outer column 505. According to some embodiments, the first, second, and third ring connectors (531, 532, 533) connect the first inner column 530 and the first outer column 505 through about 60° of angular space ($\alpha$). The first, second, and third ring connectors (531, 532, 533) are also connected to the second outer column 510 through a similar amount of angular space ($\alpha$) (about 60°). These amounts are preferably similar to each other to balance the mechanical loads that are applied to the dynamization device 500. The first, second, and third ring connectors (531, 532, 533) are unconnected through about 120° of angular space ($\beta$) on opposing sides of the device. The unconnected sections of the deformable rings can deform and flex when the first inner column 530 and the second inner column 535 are longitudinally displaced with respect to each other. Moreover, the greater the degree to which the deformable rings are connected to each other and to the inner columns (e.g., 120°, 130°, 60°, or 45°) can affect the strength of the dynamization device 500, as well as the desired spring coefficient to be provided by the device when the first and second inner columns are longitudinally displaced. In the embodiment disclosed in FIG. 5A, the preferred embodiment of the ring connectors uses connections through about 60° of angular space (α), while leaving about 120° of angular space (β) unconnected.

A side view of the embodiment of FIG. 5A is depicted in FIG. 5B. In FIG. 5B, a dynamization device 500 includes a series of deformable rings (516, 517, 518, 521, 522, 523) that are coaxial to the longitudinal axis A-A' of the dynamization device 500. All of the deformable rings are connected to a first outer column 505 and a second outer column 510. Also shown is the first inner column 530 that is positioned at the first end 502 of the device 500 and the second inner column 535 that is positioned at the second end 504 of the device 500. Also shown in FIG. 5B is the first protrusion 540 that extends longitudinally from the first end 502 of the device 500. The first protrusion may include chordal surfaces 552. Further shown in FIG. 5B is a displacement gap D that is located between the first inner column 530 and the second inner column 535. As the first end 502 of the device 500 is longitudinally displaced with respect to the second end 504, the displacement gap D may increase or decrease, as the deformable rings (516, 517, 518, 521, 522, 523) are bent and flexed during the displacement. The size, shape, connections, and range of angular space for the connection (α, β) can affect the spring coefficient of the device 500, thereby allowing a range of movement and mechanical bias to be provided by the device.

An appropriate locking device, similar to the locking device 300 depicted in FIG. 3 can be used with the embodiment of FIGS. 5A and 5B to eliminate or provide dynamization movement. In addition, as an alternative to the locking device 300 depicted in FIG. 3, a nut or other similar threaded fastener that may be placed on a threaded bolt, rod, or connector near the end the dynamization device 500. In the embodiment shown in FIGS. 5A and 5B, the threaded fastener should be of sufficient width to cover both part of the second inner column 535 and the deformable ring 521 at the second end 504 of the device 500. Suitable embodiments include a disc with the same outer diameter as the dynamization device, or a locking device 590, depicted in FIG. 5C, which is of sufficient length L to cover part of both of the second inner column 535 and the deformable ring 521. An additional benefit of using a threaded faster as the locking device is that it can permit controlled amounts of dynamization to be imparted to the dynamization device 500. For example, if only a limited amount of dynamization is desired, such as at the beginning of a therapeutic regimen, then the threaded fastener can be backed away from the end of the dynamization device 500 by a controlled amount (e.g., one quarter turn, one half turn, one full turn, etc.), again, depending on the lead and pitch of the thread. In this manner, the surgeon or medical technician can gradually apply increasing amounts of dynamization to the dynamization device 500 and to the patient, consistent with the therapeutic regimen. It is contemplated that a variety of different devices can be used to control the amount of dynamization provided by the dynamization device 500, consistent with this description.

Figure 5D:
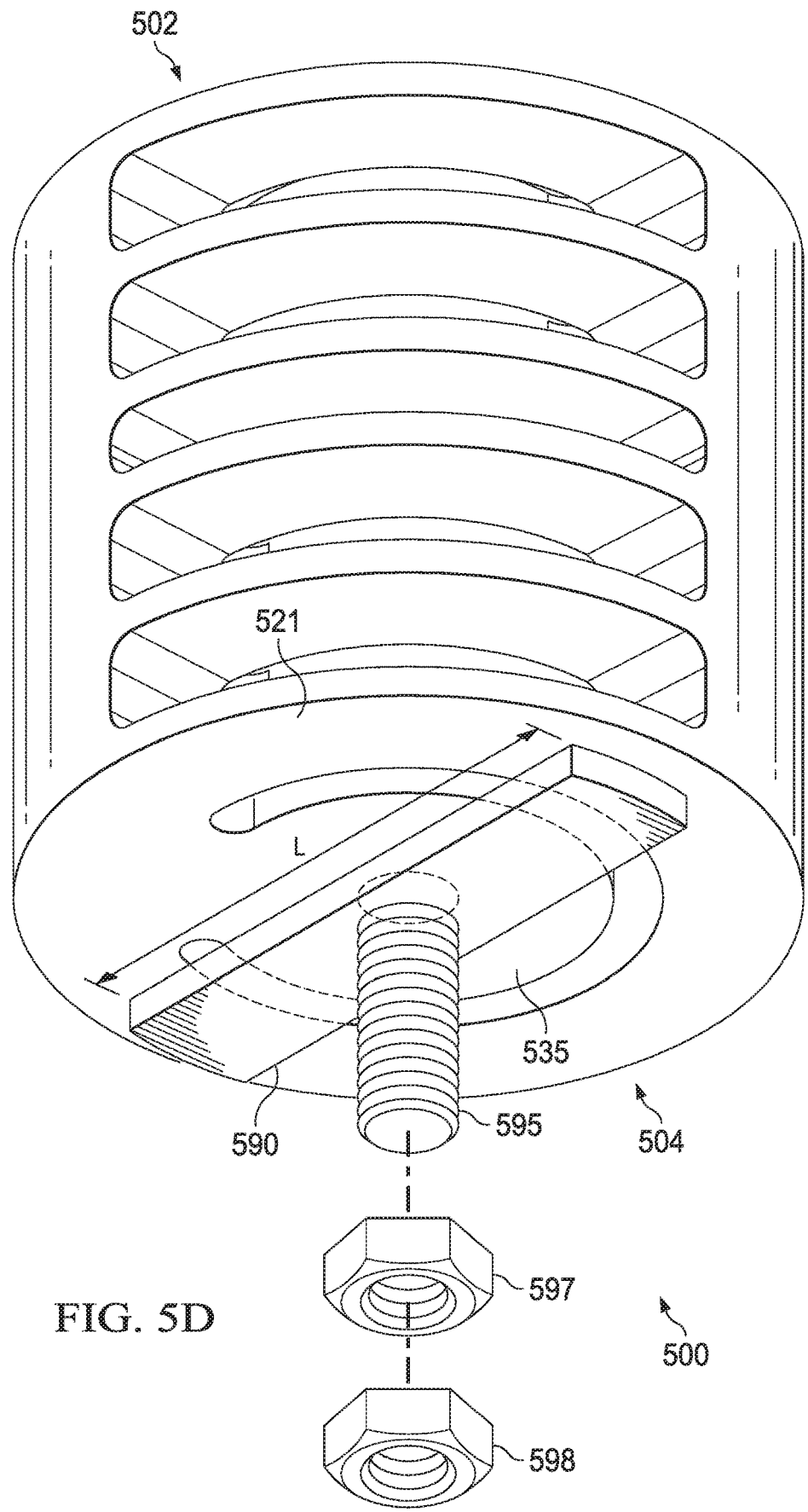
FIG. 5D illustrates a perspective view of an alternative embodiment of a dynamization device with a locking device.
Figure 5E:
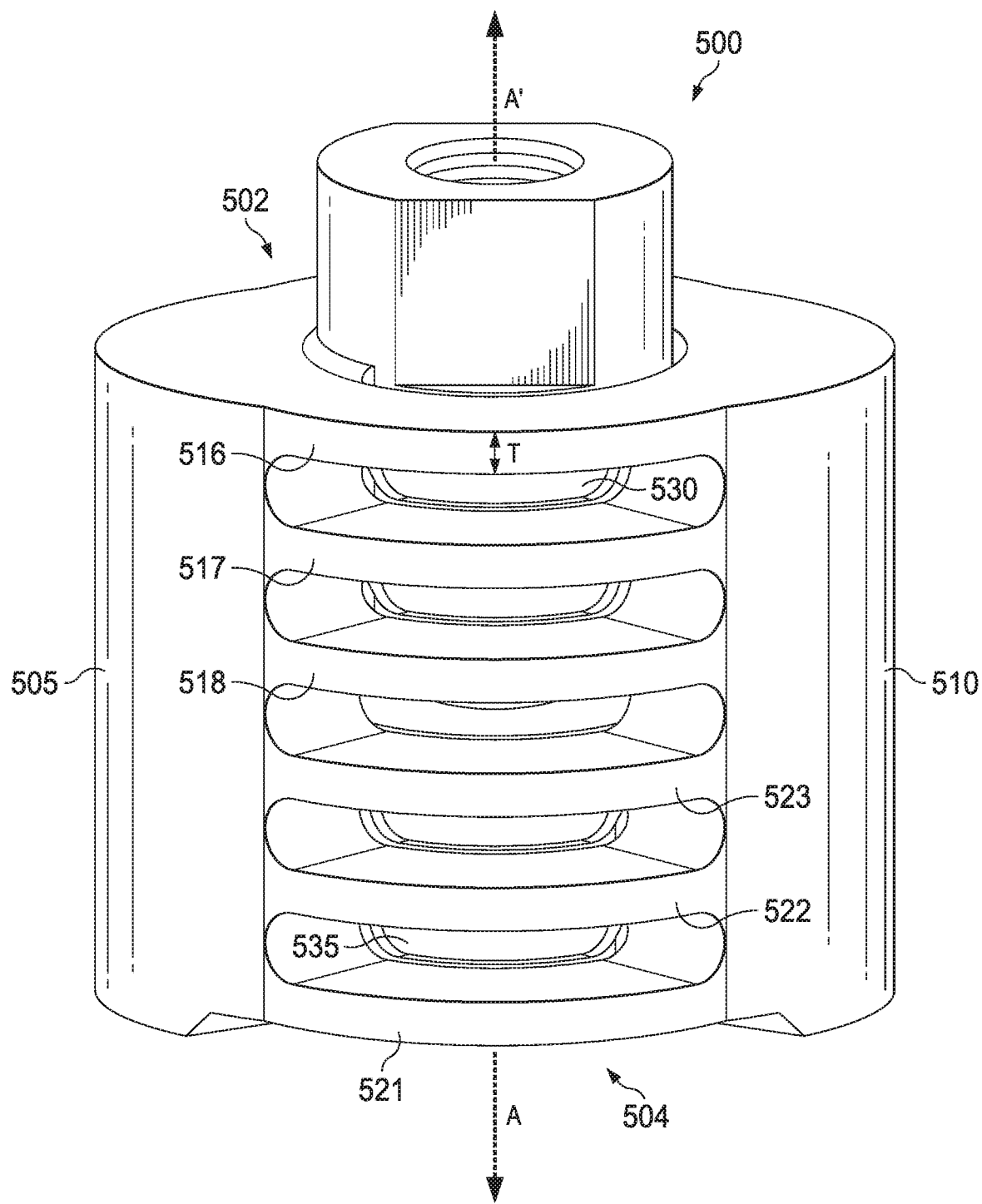
FIG. 5E illustrates a perspective view of an alternative embodiment of a dynamization device.

A perspective view of a locking device 590 adjacent to the dynamization device 500 is depicted in FIG. 5D. In FIG. 5D, the locking device 590 has been threaded onto a threaded rod 595 located at the second end 504 of the dynamization device 500. If the locking device 590 is threaded until it is adjacent to the second end 504 of the dynamization device 500, this prevents the compressive longitudinal movement of the second inner column 535 with respect to the deformable ring 521. This prevents the compressive movement of the dynamization device 500. As mentioned above, the locking device 590 must be of sufficient length L to cover part of both of the second inner column 535 and the deformable ring 521. According to one embodiment, additional locking nuts (597, 598) can be threaded onto the end of the threaded rod 595 to further secure the placement of the locking device against the second end 504 of the device 500. Preferably, these additional locking nuts are provided in a pair, so that when they are threaded against each other, they can control the distance D at which the locking device 590 is placed away from the second end 504 of the dynamization device 500. In this manner, the amount of dynamization provided by the dynamization device 500 can be controlled, as described above. An alternative embodiment of the dynamization device 500 of FIG. 5A is depicted in FIG. 5E. In FIG. 5E, the dynamization device 500 uses two sets of deformable rings (516, 517, 518, 521, 522, 523) that form connections between the first outer column 505, second outer column 510, first inner column 530, and second inner column 535. In contrast to the embodiment of FIG. 5A, the size of the first and second outer columns 505, 510 are much larger, providing an oval shape to the overall device 500, rather than the substantially cylindrical shape depicted in FIG. 5A. In addition, the thickness of the deformable rings T in FIG. 5E is much larger than the thickness of the rings depicted in FIG. 5A. These features provide additional strength to the dynamization device 500, making it less susceptible to lateral and torsional loads that are applied to the dynamization device 500. In addition, since the thickness of the deformable rings T is larger, the device will have a larger spring coefficient, and this impart a larger mechanical bias during the dynamization process. Thus, the device of FIG. 5E may be more appropriate for therapeutic use with larger bones that are more susceptible to larger loading stresses and require greater mechanical bias during the dynamization process.

Figure 5F:
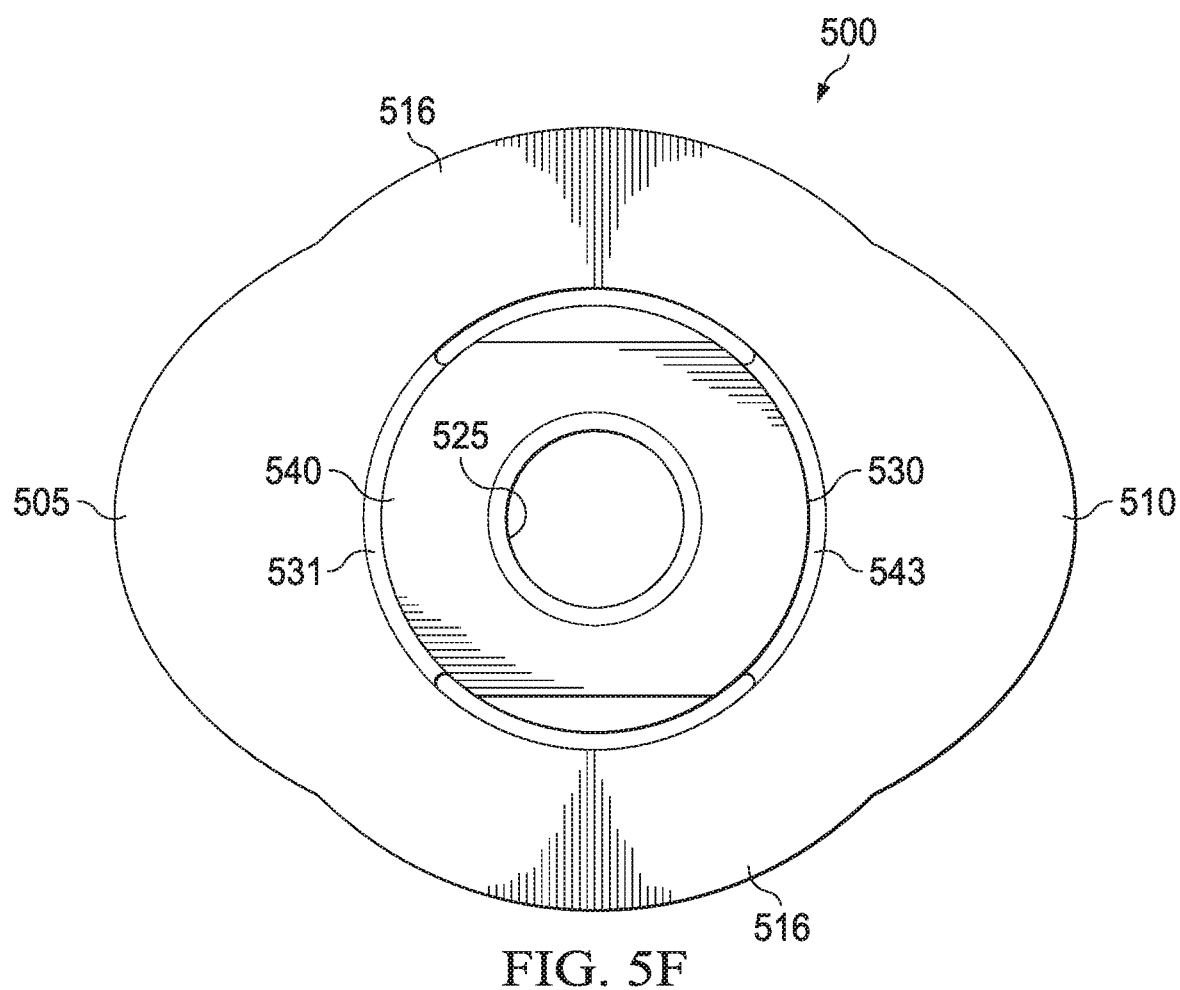
FIG. 5F illustrates a perspective view of one embodiment of a dynamization device.

A top view of the embodiment of FIG. 5E is depicted in FIG. 5F. In FIG. 5F, the dynamization device 500 is shown with the first and second outer columns (505, 510) and the first inner column 530. Also shown in FIG. 5F are top views of the first deformable ring 516, the first protrusion 540, and the threaded aperture 525. The first outer column 505 is connected to the first inner column 505 by a ring connector 531. Another ring connector 543 is shown, but it connects the second inner column 535 (not shown) to the second outer column 510. The generally oval shape of the dynamization device 500 is apparent in the top view of this structure. It is contemplated that other shapes can be provided for the outer columns, depending upon the particular mechanical loads, degree of dynamization, anatomical concerns, or other needs for the dynamization device 500. Any of the locking devices described above with reference to FIGS. 1F, 3, 4E, 5C, and 5D can be used with the dynamization device 500 depicted in FIGS. 5E and 5F.

Figure 5G:
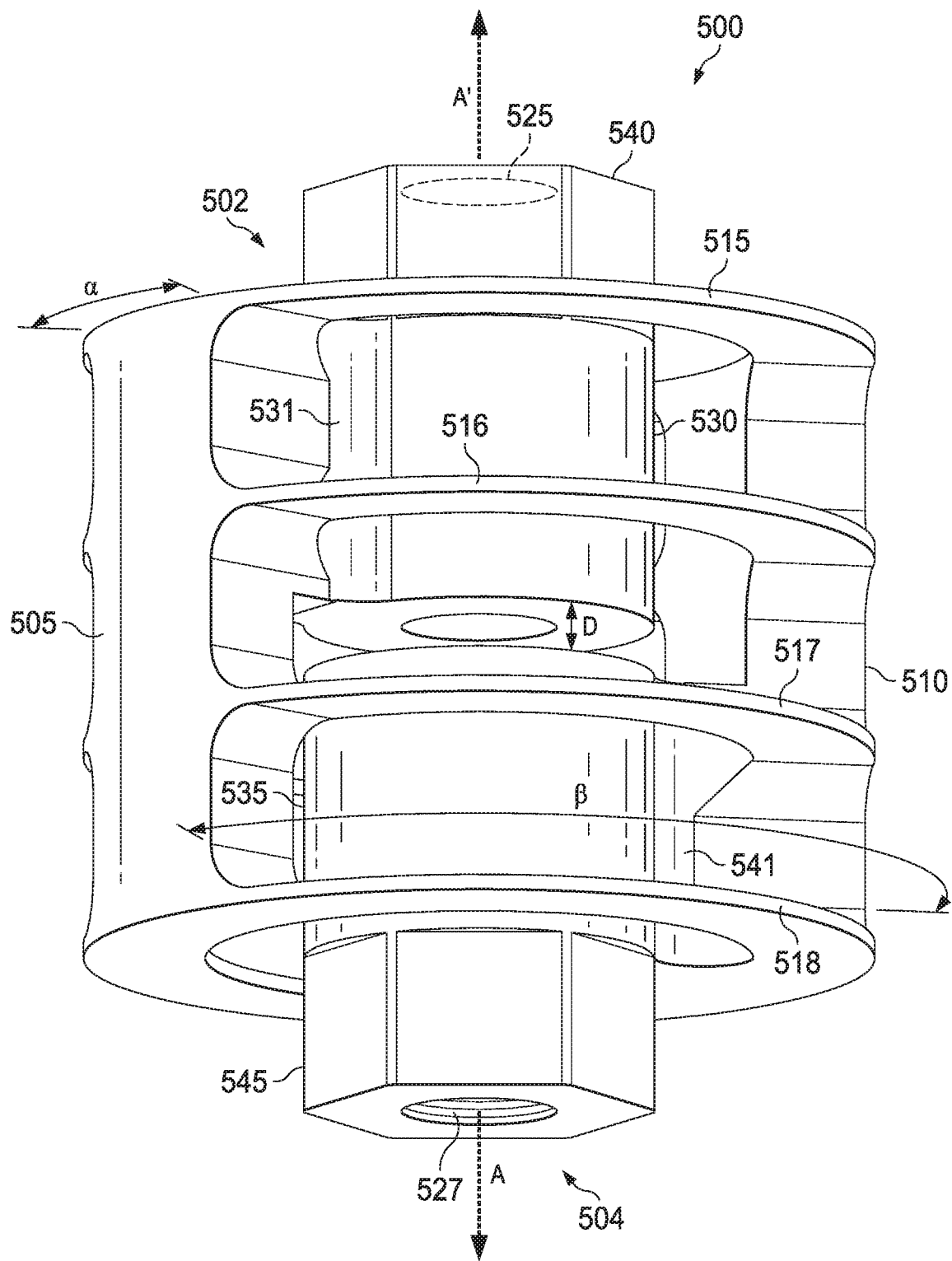
FIG. 5G illustrates a perspective view of an alternative embodiment of a dynamization device.

Another alternative embodiment of a dynamization device is depicted in FIG. 5G. In FIG. 5G, a dynamization device 500 has a generally cylindrical shape along a longitudinal axis A-A'. The dynamization device 500 is comprised of a series of deformable rings that are coaxial to the longitudinal axis A-A' of the dynamization device 500. The number of deformable rings that can be utilized in this embodiment can be as few as two, four (as shown in FIG. 5G), or many more, depending upon the desired strength, size, and degree of mechanical bias to apply during the dynamization process. As shown in FIG. 5G, four deformable rings are shown: first deformable ring 515, second deformable ring 516, third deformable ring 517, and fourth deformable ring 518. All of the rings are depicted in FIG. 5G as being connected by a first outer column 505 and a second outer column 510. This embodiment further includes a first inner column 530 that is positioned at the first end 502 of the device 500 and a second inner column 535 that is positioned at the second end 504 of the device 500. Also shown in FIG. 5G are a first protrusion 540 and a second protrusion 545 that extend longitudinally from the first end 502 and second end 504, respectively. The first protrusion 540 includes a threaded aperture 525 (not shown) to which a threaded bolt, rod, or other connector can attach to the first inner column 530 at the first end 502 of the dynamization device 500. The second protrusion 545 includes a threaded aperture 527 to which a threaded bolt, rod, or other connector can attach to the second inner column 535 at the second end 504 of the dynamization device 500. Each protrusion (540, 545) has an outer surface that includes a plurality of flat surface that can accommodate a wrench, ratchet, or other tool that can hold the dynamization device 500 in place as a threaded bolt, rod, or other connector is attached to the threaded apertures (525, 527). A ring connector 531 is depicted in FIG. 5G as connecting the first outer column to the first inner column 530. Unlike the embodiment depicted in FIG. 5A, the ring connector 531 of FIG. 5G connects the first outer column 505 to the first inner column 530 for the entire longitudinal length of the first inner column. This provides greater strength to the connection between the first inner column and the first outer column and reducing the range of angular space for the connection (α). Similarly, ring connector 541 is depicted in FIG. 5F as connecting the second outer column 541 to the second inner column 535. The ring connector 541 connects the second outer column 510 to the second inner column 535 for the entire longitudinal length of the second inner column. This provides greater strength to the connection between the second inner column and the second outer column and reducing the range of angular space for the connection (α). The range of angular space (α) for the first and second ring connectors (531, 541) are preferably similar to each other to balance the mechanical loads that are applied to the dynamization device 500. The first, second, third, and fourth deformable rings (515, 516, 517, 518) are unconnected through about 160° of angular space (β) on opposing sides of the device. The unconnected sections of the deformable rings can deform and flex when the first inner column 530 and the second inner column 535 are longitudinally displaced with respect to each other. Moreover, the greater the degree to which the outer columns (505, 510) are connected to the inner columns (530, 535) (e.g., 120°, 130°, 60°, or 45°) can affect the strength of the device, as well as the desired spring coefficient to be provided by the device when the first and second inner columns (530, 535) are longitudinally displaced. In the embodiment disclosed in FIG. 5G, the preferred embodiment of the ring connectors uses connections through about 40° of angular space (α), while leaving about 140° of angular space (β) unconnected.

Further shown in FIG. 5G is a displacement gap D that is located between the first inner column 530 and the second inner column 535. As the first end 502 of the device 500 is longitudinally displaced with respect to the second end 504, the displacement gap D may increase or decrease, as the deformable rings (515, 516, 517, 518) are bent and flexed during the displacement. The size, shape, connections, and range of angular space for the connection (α, β) can affect the spring coefficient of the dynamization device 500, thereby allowing a range of movement and mechanical bias to be provided by the dynamization device 500.

An appropriate locking device, similar to the locking device 300 depicted in FIG. 3 can be used with the embodiment of FIG. 5G to eliminate or provide dynamization movement. In addition, as an alternative to the locking device 300 depicted in FIG. 3, a nut or other similar threaded fastener that may be placed on a threaded bolt, rod, or connector near the end the dynamization device 500. A threaded fastener should be of sufficient width to cover both part of the inner column (530, 535) and a deformable ring (515, 518) at an end of the device (502, 504). Suitable embodiments include a disc with the same outer diameter as the dynamization device with an annular lip that would allow the disc to be in contact with the outer surface of the protrusion (e.g., 540, 545) and a deformable ring (515, 518) at the same time. An additional benefit of using a threaded faster as the locking device is that it can permit controlled amounts of dynamization to be imparted to the device 500. For example, if only a limited amount of dynamization is desired, such as at the beginning of a therapeutic regimen, then the threaded fastener can be backed away from the end of the dynamization device 500 by a controlled amount (e.g., one quarter turn, one half turn, one full turn, etc.), again, depending on the lead and pitch of the thread. In this manner, the surgeon or medical technician can gradually apply increasing amounts of dynamization to the device and to the patient, consistent with the therapeutic regimen. It is contemplated that a variety of different devices can be used to control the amount of dynamization provided by the device 500, consistent with this description.

Figure 6A:
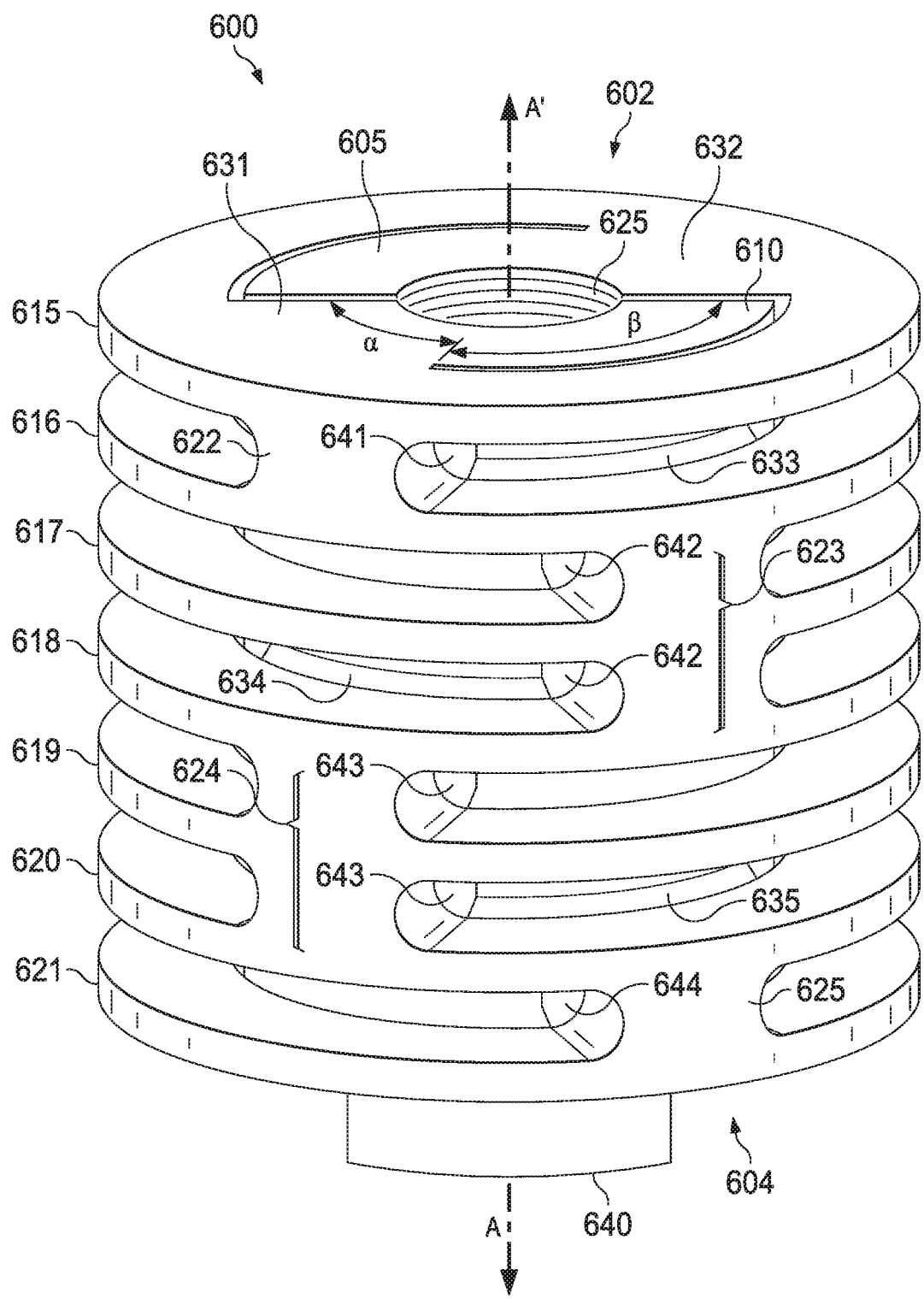
FIG. 6A illustrates a perspective view of one embodiment of a dynamization device.

Another representative embodiment of a dynamization device 600 is depicted in FIG. 6A. In FIG. 6A, a dynamization device 600 has a generally cylindrical shape along a longitudinal axis A-A'. The dynamization device 600 is comprised of a first module 605 and a second module 610 that are mated together so that the longitudinal axis of the first module 605 is coaxial to the longitudinal axis of the second module 610 and the longitudinal axis A-A' of the dynamization device 600. Positioned along the length of the device 600 is a set of deformable rings (615-621). Each of these rings are connected to a portion of the first and second modules 605, 610 by one or more ring connectors. The connection of the first deformable ring 615 to the first and second modules 605, 610 is depicted in FIG. 6A with first ring connectors 631 and 632. These first ring connectors (631, 632) may occupy radial positions that are opposite each other with respect to the longitudinal axis A-A'. The first deformable ring 615 and the second deformable ring 616 are also connected to each other by a first outer column 622. The second deformable ring 616, the third deformable ring 617, and the fourth deformable ring 618 are also connected to each other by a second outer column 623. The fourth deformable ring 618, the fifth deformable ring 619, and the sixth deformable ring 620 are also connected to each other by a third outer column 624. In addition, the sixth deformable ring 620 and the seventh deformable ring 621 are connected to each other by a fourth outer column 622. A similar set of outer columns (not shown) are located on an opposite side of the dynamization device 600. As shown in FIG. 6A, the second deformable ring 616 is connected to the inner module 610 by second ring connector 633. The fourth deformable ring 618 is also connected to the inner module 610 by fourth ring connector 634. In addition, the sixth deformable ring 620 is connected to the inner module 610 by a sixth ring connector 635. A similar set of ring connectors are located on an opposite side of the dynamization device 600. In addition to these ring connectors (631-635), the first, second, third and fourth outer columns (622, 623, 624, 625) are directly connected to the inner module 610 by column connectors 641, 642, 643, and 644, respectively.

According to some embodiments, first ring connectors 631, 632 connect to the first and second modules 605, 610 through about 60° of angular space (α), while leaving unconnected about 120° of angular space (β). The unconnected sections of the distal deformable ring 615 allow the ring to deform and flex when the first and second modules 605, 610 are longitudinally displaced with respect to each other. The second deformable ring 616 is connected to the second module 610 by the second ring connector 633. The second ring connector 633 passes through sufficient angular space (α) to overlap both the first and second outer columns (622, 623). Also shown in FIG. 6A is the fourth ring connector 634. The fourth ring connector 634 passes through sufficient angular space (α) to overlap both the second and third outer columns (623, 624). In addition, the sixth deformable ring 620 connects to the second inner module 610 with a sixth ring connector 635. The sixth ring connector 635 passes through sufficient angular space (α) to overlap both the third and fourth outer columns (624, 625).

Also shown in FIG. 6A is first protrusion 640 that extends longitudinally from the second end 604 of the device 600. The first protrusion 640 includes a threaded aperture 627 (not shown) to which a threaded bolt, rod, or other connector can attach to the second end 604 of the dynamization device 600. Also shown in FIG. 6A is threaded aperture 625 that is located at the first end 602 of the dynamization device 600. The threaded aperture 625 may be used to connect a threaded bolt, rod, or other connector to a first end 602 of the dynamization device 600. Not shown in FIG. 6A is another threaded aperture (627) that is located at the second end 604 of the device. This other threaded aperture (627) may be used to connect a threaded bolt, rod, or other connector to the second end 604 of the dynamization device 600.

Figure 6B:
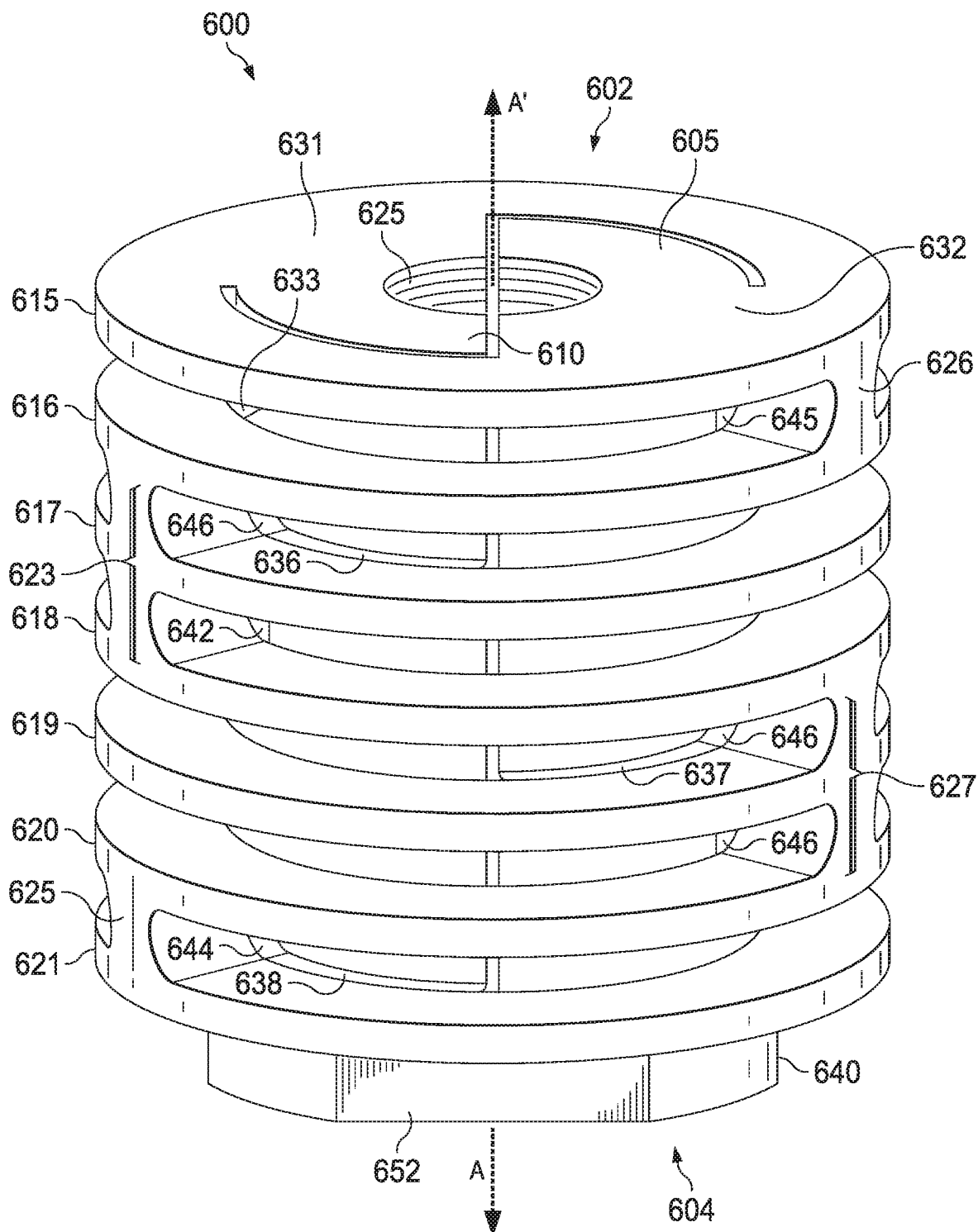
FIG. 6B illustrates another perspective view of one embodiment of a dynamization device.

An alternative view of the dynamization device 600 shown in FIG. 6A is depicted in FIG. 6B, with the device rotated 90 degrees clockwise around its longitudinal axis A-A'. Like FIG. 6A, a set of deformable rings (615-621) are positioned along the length of the dynamization device 600. Each of these rings are connected to a portion of the first and second modules 605, 610 by one or more ring connectors. The connection of the first deformable ring 615 to the first and second modules 605, 610 is depicted in FIG. 6B with first ring connectors 631 and 632. These first ring connectors (631, 632) may occupy radial positions that are opposite each other with respect to the longitudinal axis A-A'. In FIG. 6B, a fifth outer column 626 is depicted as connecting the first deformable ring 615 and the second deformable ring 616. The fifth outer column 626 is directly connected to the first module 605 by column connector 645. The second deformable ring 616, the third deformable ring 617, and the fourth deformable ring 618 are also connected to each other by a second outer column 623, which is directly connected to the second module 610 by column connector 642. The fourth deformable ring 618, the fifth deformable ring 619, and the sixth deformable ring 620 are also connected to each other by a sixth outer column 627. The sixth outer column 627 is directly connected to the first module 605 by column connector 646. In addition, the sixth deformable ring 620 and the seventh deformable ring 621 are connected to each other by a fourth outer column 625.

In FIG. 6B, the second deformable ring 616 is connected to the inner module 610 by a second ring connector 633. The third deformable ring 617 is also connected to the inner module 610 by a third ring connector 636. The fifth deformable ring 619 is also connected to the inner module 605 by a fifth ring connector 637. The seventh deformable ring 621 is also connected to the inner module 610 by a seventh ring connector 638.

The first protrusion 640 is depicted in FIG. 6B extending longitudinally from the second end 604 of the dynamization device 600. The first protrusion 640 includes a threaded aperture 627 (not shown) to which a threaded bolt, rod, or other connector can attach to the second end 604 of the dynamization device 600. Also shown in FIG. 6B is a chordal surface 652, which forms a flattened surface at the second end 604 of the dynamization device 600. According to one embodiment, a matching chordal surface is found on the other side of the first protrusion 640, thus forming a pair that is radially positioned opposite each other and can be used to hold the dynamization device 600 in place as a threaded bolt, rod, or other connector to the dynamization device 600.

Figure 6C:
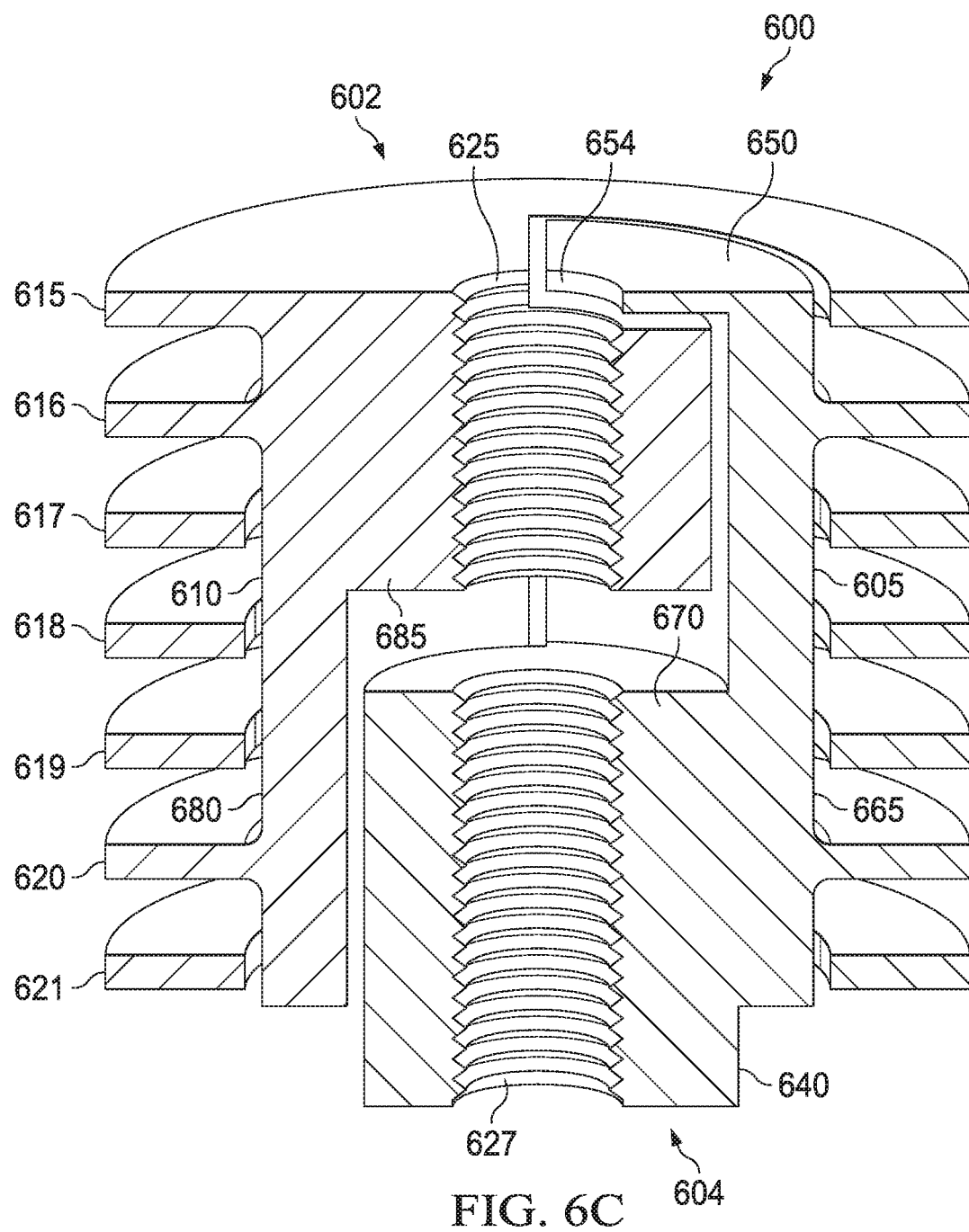
FIG. 6C illustrates a cross-sectional perspective view of one embodiment of a dynamization device.

A cross sectional view of the representative embodiment of FIG. 6B is depicted in FIG. 6C. In FIG. 6C, the dynamization device 600 is shown with the first module 605 on the right-hand side and the second module 610 on the left-hand side. The first module 605 is depicted as having an outer wall 665 and an inner column 670. The second module 610 is depicted as having an outer wall 680 and an inner column 685. The first and second modules 605, 610 can be mated together in the same way as the embodiment of FIG. 1A-1E. Similarly, by longitudinally displacing the first module 605 with respect to the second module 610, the unconnected sections of the deformable rings (615-621) will be deformed so as to apply a longitudinal mechanical bias to the dynamization device 600 to return it to its original position. Also depicted in FIG. 6C are threaded apertures 625 and 627, which can receive a threaded bolt, rod, or other connector at respective ends of the dynamization device 600. Also depicted in FIG. 6D is a stopping member 650 that protrudes from an end of the outer wall 665 of the first module 605. The stopping member 650 is depicted as an inwardly protruding lip that includes an inner surface 654. The inner surface 654 must be of sufficient size to permit a threaded bolt, rod, or other connector to attach to the threaded aperture 625 at the first end 602 of the dynamization device 600. The inwardly protruding lip prevents the second module 610 from longitudinally displacing away from the first module 605, thereby imparting undesirable distractive movement, rather than desirable compressive movement. Although not shown in FIG. 6C, a second stopping member can be placed at the other end of the device 600 to provide further protection against undesirable distractive movement. Also shown in FIG. 6C is first protrusion 640 that extends longitudinally from the second end 604 of the dynamization device 600. The first protrusion 640 includes a threaded aperture 627 to which a threaded bolt, rod, or other connector can attach to the first inner column 670 at the second end 604 of the dynamization device 600. Any of the locking devices described above with reference to FIGS. 1F, 3, 4E, 5C, and 5D can be used with the dynamization device 600 depicted in FIGS. 6A, 6B, and 6C.

Figure 7A:
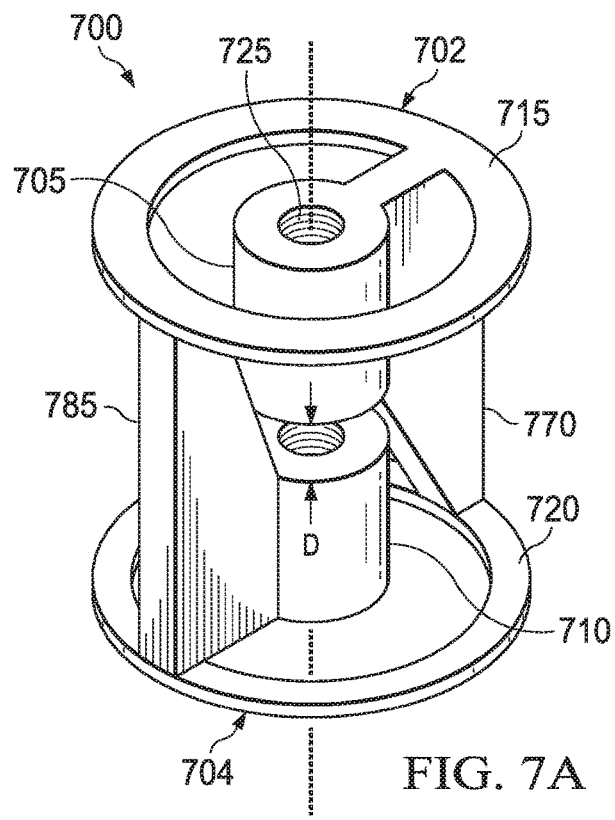
FIG. 7A illustrates a perspective view of one embodiment of a dynamization device.

Another representative embodiment of a dynamization device 700 is depicted in FIG. 7A. In FIG. 7A, a dynamization device 700 has a generally cylindrical shape along a longitudinal axis A-A'. The dynamization device 700 is comprised of a first module 705 and a second module 710 that are mated together so that the longitudinal axis of the first module 705 is coaxial to the longitudinal axis of the second module 710 and the longitudinal axis A-A' of the dynamization device 700. The first and second modules (705, 710) are connected to a pair of deformable rings 715, 720 positioned at first and second ends 702, 704 of the dynamization device 700, respectively. First ring 715 is connected to the first module 705 by a first column 770 that extends from the first end of the device 702 to the second end of the device 704, where it connects to the second ring 720. Second ring 720 is also connected to the second module 710 by a second column 785 that extends from the second end of the device 704 to the first end of the device 702, where it is connected to the first ring 715. Although only two rings 715, 720 are depicted in FIG. 7A, many more deformable rings can be added to this embodiment without departing from the spirit of the invention. FIG. 7A also illustrates that a displacement distance D is located between the first module 705 and the second module 710. This displacement distance is preferably in the range of about 1-3 mm, with a preferred maximum of about 3 mm. As a result, when the first module 705 is longitudinally compressed towards the second module 710, the compressive displacement of the device will stop when the first module 705 comes into contact with the second module 710. During this longitudinal compression, the rings (715, 720) are deformed, thus creating a mechanical bias that causes the dynamization device 700 to return to its original position when the longitudinal compressive force is removed.

Also shown in FIG. 7A is threaded aperture 725 that is located at the first end 702 of the device. The threaded aperture 725 may be used to connect a threaded bolt, rod, or other connector to a first end 702 of the dynamization device 700. Not shown in FIG. 7A is another threaded aperture that is located at the second end 704 of the device. This other threaded aperture may be used to connect a threaded bolt, rod, or other connector to the second end 704 of the dynamization device 700.

Figure 7B:
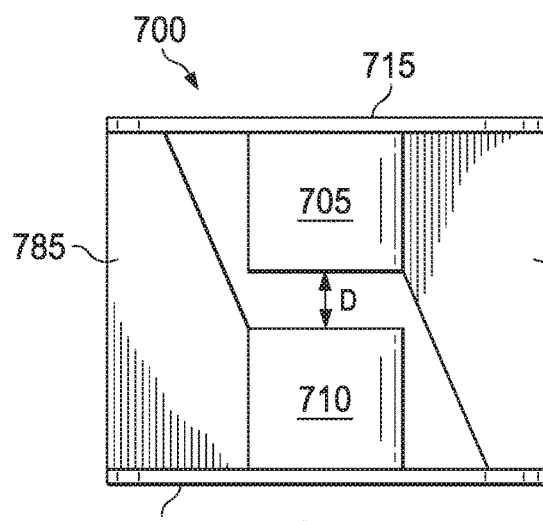
FIG. 7B illustrates a side view of one embodiment of a dynamization device.

A side view of the representative dynamization device 700 of FIG. 7A is depicted in FIG. 7B. In FIG. 7B, the dynamization device 700 is shown as viewed from the side, with the first module 705 connected to the first column 770 and the second module 710 connected to the second column 785. The displacement distance D is depicted between the first module 705 and the second module 710. A side view of the first and second deformable rings 715, 720 are also depicted in FIG. 7B.

Figure 7C:
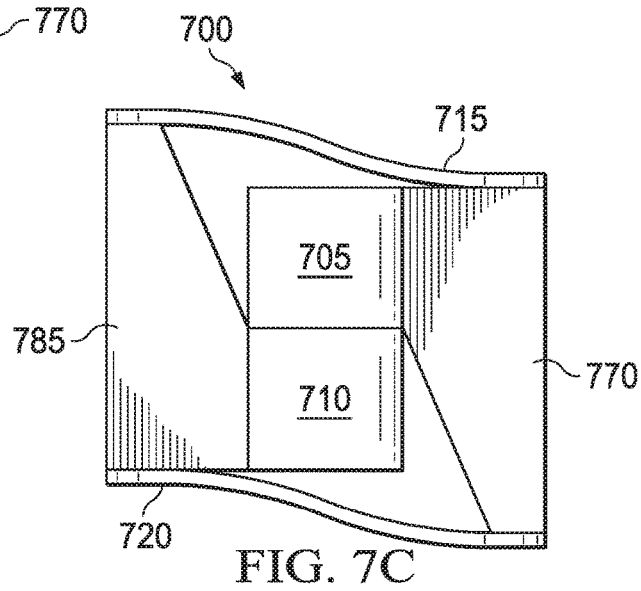
FIG. 7C illustrates another side view of one embodiment of a dynamization device.

Another representative side view of the dynamization device 700 is depicted in FIG. 7C. In FIG. 7C, the dynamization device 700 is again shown from the side, but the first module 705 has been longitudinally displaced towards the second module 710. As a result, the displacement distance D is reduced until the first module 705 contacts the second module 710. As this occurs, the first and second deformable rings 715, 720 are displaced with respect to each other. As depicted in FIG. 7C (with hatched lines), the deformable rings 715, 720 are held in contact with the first column 770 and the second column 785 as the modules 705, 710 are longitudinally displaced with respect to each other. This deforms the shape of the rings 715, 720 so that a longitudinal mechanical bias is applied between the first and second modules 705, 710 to return the deformable rings to their original position. These longitudinal mechanical biases return the dynamization device 700 to its original position when the longitudinal force is removed. Any of the locking devices described above with reference to FIGS. 1F, 3, 4E, 5C, and 5D can be used with the dynamization device 700 depicted in FIGS. 7A-7C. Another exemplary locking device can be inserted into the gap between the first module 705 and the second module 710, thereby preventing those modules from longitudinally displacing towards each other.

Figure 8A:
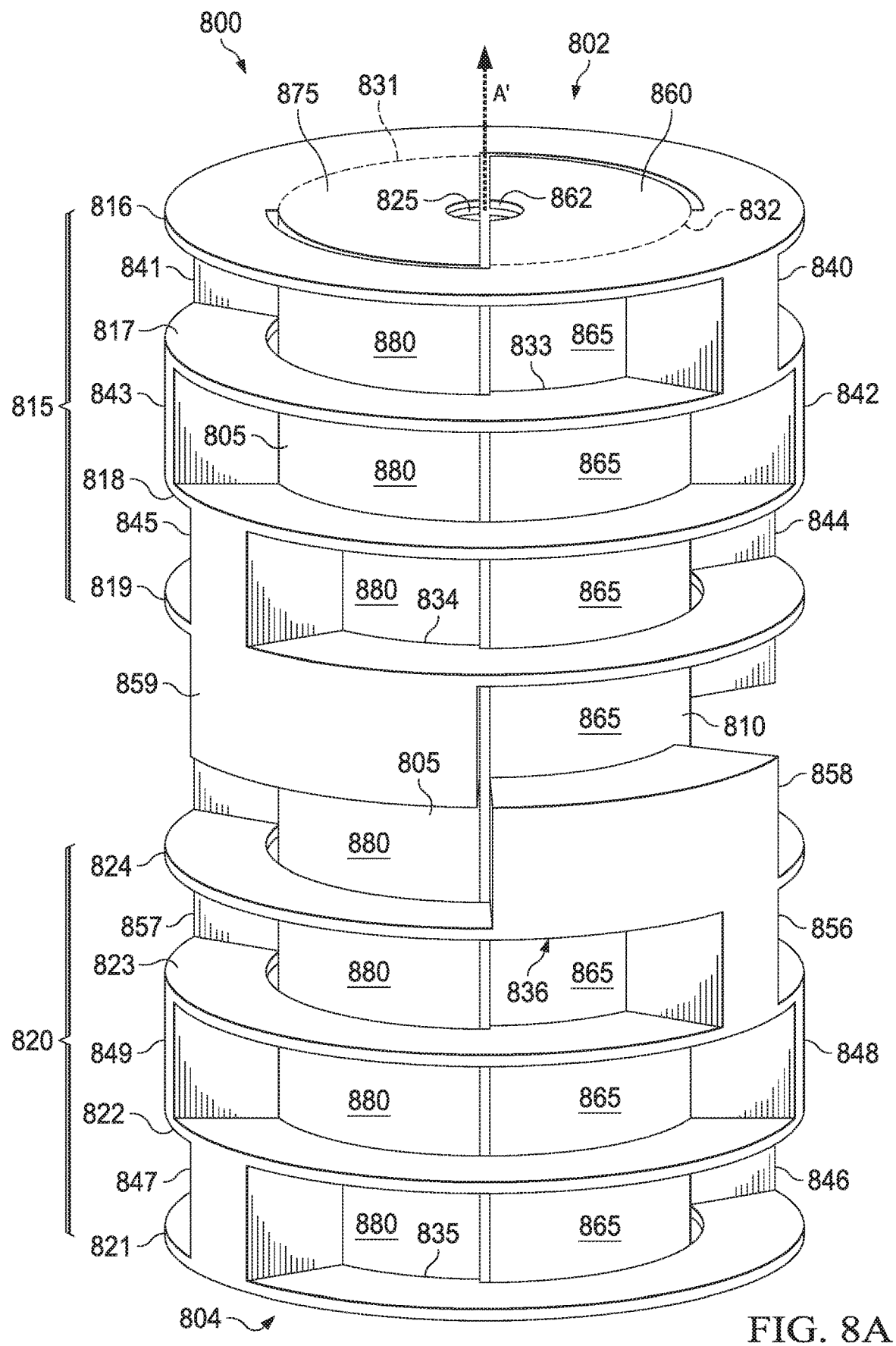
FIG. 8A illustrates a perspective view of one embodiment of a dynamization device.

Anther representative embodiment of a dynamization device is depicted in FIG. 8A. In FIG. 8A, a dynamization device 800 has a generally cylindrical shape along a longitudinal axis A-A'. The dynamization device 800 is comprised of a first module 805 and a second module 810 that are mated together so that the longitudinal axis of the first module 805 is coaxial to the longitudinal axis of the second module 810 and the longitudinal axis A-A' of the dynamization device 800. Positioned at a first end 802 of the device 800 is a set of first deformable rings 815. Positioned at a second end 804 of the device 800 is a set of second deformable rings 820. In the embodiment depicted in FIG. 8A, the set of first deformable rings 815 may comprise a first deformable ring 816, a second deformable ring, 817, a third deformable ring 818, and a fourth deformable ring 819. As few as one deformable ring may be used, but generally two to four sets of deformable rings may be used, however, more than four deformable rings may be used for each set of deformable rings without departing from the spirit of the invention. The set of second deformable rings 820 may similarly comprise a fifth deformable ring 821, a sixth deformable ring, 822, a seventh deformable ring 823, and an eighth deformable ring 824. Each ring is connected to a portion of the first and second modules 805, 810 by one or more ring connectors. The connection of the first deformable ring 816 to the first and second modules 805, 810 is depicted in FIG. 8A with first ring connectors 831 and 832. These ring connectors (831, 832) may occupy radial position that are opposite each other with respect to the longitudinal axis A-A'. Although two ring connectors 831, 832 are depicted in FIG. 8A to connect the deformable rings to the first and second modules 805, 810, a plurality of connectors can be used without departing from the spirit of the invention. Also shown in FIG. 8A is the connection of the second deformable ring 817 to the second module 810 through the second ring connector 833. A similar ring connector that connects the second deformable ring 817 to the first module 805 is positioned radially opposite the second ring connector 833, but is not shown in FIG. 8A. The fourth deformable ring 819 is connected to the first module 805 through a fourth ring connector 834. A similar ring connector that connects the fourth deformable ring 819 to the second module 810 is positioned radially opposite the fourth ring connector 834, but is not shown in FIG. 8A. The fifth deformable ring 821 is connected to the first module 805 through a fifth ring connector 835. A similar ring connector that connects the fifth deformable ring 819 to the second module 810 is positioned radially opposite the fifth ring connector 835, but is not shown in FIG. 8A. The eighth deformable ring 824 is connected to the second module 810 through an eighth ring connector 836. A similar ring connector that connects the eighth deformable ring 824 to the first module 805 is positioned radially opposite the eighth ring connector 836, but is not shown in FIG. 8A.

The first deformable ring 816 and the second deformable ring 817 are also connected to each other by a pair of first outer columns 840, 841. First outer column 840 is directly connected to the outer wall of the second module 810 to form a rigid support structure for the connection of the first and second deformable rings 816, 817 to the second module 810. On a radially opposite side of the dynamization device 800, first outer column 841 is directly connected to the outer wall of the first module 805 to form a rigid support structure for the connection of the first and second deformable rings 816, 817 to the first module 805. The first outer columns (840, 841) have a radial width of about 5-10 degrees, with respect to the longitudinal axis of the dynamization device

800. The second deformable ring 817 and the third deformable ring 818 are also connected to each other by a pair of second outer columns 842, 843. Second outer column 842 is directly connected to the outer wall of the second module 810 to form a rigid support structure for the connection of the second and third deformable rings 817, 818 to the second module 810. On a radially opposite side of the dynamization device 800, second outer column 843 is directly connected to the outer wall of the first module 805 to form a rigid support structure for the connection of the second and third deformable rings 817, 818 to the first module 805. The second outer columns (842, 843) have a radial width of about 5-10 degrees, with respect to the longitudinal axis of the device. The second outer columns 842, 843 are radially displaced by approximately 30-60 degrees (preferably 45 degrees) from the placement of the first outer columns 840, 841, with respect to the longitudinal axis A-A' of the dynamization device 800. In a preferred embodiment, there is no overlap between the radial edges of the first outer columns and the second outer columns. The third deformable ring 818 and the fourth deformable ring 819 are also connected to each other by a pair of third outer columns 844, 845. Third outer column 844 is directly connected to the outer wall of the second module 810 to form a rigid support structure for the connection of the third and fourth deformable rings 818, 819 to the second module 810. On a radially opposite side of the dynamization device 800, third outer column 845 is directly connected to the outer wall of the first module 805 to form a rigid support structure for the connection of the third and fourth deformable rings 818, 819 to the first module 805. The third outer columns (844, 845) have a radial width of about 5-10 degrees, with respect to the longitudinal axis of the device. The third outer columns 844, 845 are radially displaced by approximately 30-60 degrees (preferably 45 degrees) from the placement of the second outer columns 842, 843, with respect to the longitudinal axis A-A' of the dynamization device 800. In a preferred embodiment, there is no overlap between the radial edges of the second outer columns and the third outer columns. The placement of the first, second, and third outer columns along different radial positions of the first set of deformable rings 815 create additional strength and stability for the device 800 and help to ensure that any displacement and movement of the device only occurs along the longitudinal axis A-A' of the dynamization device 800.

The fifth deformable ring 821 and the sixth deformable ring 822 are also connected to each other by a pair of fourth outer columns 846, 847. Fourth outer column 846 is directly connected to the outer wall of the second module 810 to form a rigid support structure for the connection of the fifth and sixth deformable rings 821, 822 to the second module 810. On a radially opposite side of the dynamization device 800, fourth outer column 847 is directly connected to the outer wall of the first module 805 to form a rigid support structure for the connection of the fifth and sixth deformable rings 821, 822 to the first module 805. The fourth outer columns (846, 847) have a radial width of about 5-10 degrees, with respect to the longitudinal axis of the device. The sixth deformable ring 822 and the seventh deformable ring 823 are also connected to each other by a pair of fifth outer columns 848, 849. Fifth outer column 848 is directly connected to the outer wall of the second module 810 to form a rigid support structure for the connection of the sixth and seventh deformable rings 822, 823 to the second module 810. On a radially opposite side of the dynamization device 800, fifth outer column 849 is directly connected to the outer wall of the first module 805 to form a rigid support structure for the connection of the sixth and seventh deformable rings 822, 823 to the first module 805. The fifth outer columns (848, 849) have a radial width of about 5-10 degrees, with respect to the longitudinal axis of the dynamization device 800. The fifth outer columns (848, 849) are radially displaced by approximately 30-60 degrees (preferably 45 degrees) from the placement of the fourth outer columns 846, 847, with respect to the longitudinal axis of the device A. In a preferred embodiment, there is no overlap between the radial edges of the fourth outer columns and the fifth outer columns. The seventh deformable ring 823 and the eighth deformable ring 834 are also connected to each other by a pair of sixth outer columns 856, 857. Sixth outer column 856 is directly connected to the outer wall of the second module 810 to form a rigid support structure for the connection of the seventh and eighth deformable rings 823, 834 to the second module 810. On a radially opposite side of the device 800, sixth outer column 857 is directly connected to the outer wall of the first module 805 to form a rigid support structure for the connection of the seventh and eighth deformable rings 823, 824 to the first module 805. The sixth outer columns (856, 857) have a radial width of about 5-10 degrees, with respect to the longitudinal axis of the device. The sixth outer columns 856, 857 are radially displaced by approximately 30-60 degrees (preferably 45 degrees) from the placement of the fifth outer columns 848, 849, with respect to the longitudinal axis A-A' of the dynamization device 800. In a preferred embodiment, there is no overlap between the radial edges of the fifth outer columns and the sixth outer columns. The placement of the fourth, fifth, and sixth outer columns along different radial positions of the second set of deformable rings 820 create additional strength and stability for the device 800 and help to ensure that any displacement and movement of the device only occurs along the longitudinal axis A-A' of the dynamization device 800.

Also depicted in FIG. 8A are minor columns 858 and 859, which are attached to the eighth deformable ring 824 and the fourth deformable ring 819, respectively. Minor column 858 forms a rigid connection between the eighth deformable ring 824 and the second module 810 and passes through a radial distance of about 60 degrees. Minor column 859 forms a rigid connection between the fourth deformable ring 819 and the first module 805 and passes through a radial distance of about 60 degrees. When the dynamization device 800 is in a deformed or displaced arrangement, minor columns 858 and 859 act as stopping mechanisms to prevent further compression and damage of the dynamization device 800. More specifically, when the first module 805 is longitudinally displaced with respect to the second module 810 (as shown in FIG. 8C), the minor columns 858, 859 will prevent excessive longitudinal displacement. This occurs when the upper face of the minor column 858 abuts the lower face of the fourth deformable ring 819 and when the lower face of the minor column 859 abuts the upper face of the eighth deformable ring 824.

Further shown in FIG. 8A is threaded aperture 825 that is located at the first end 802 of the first module 805. The threaded aperture 825 may be used to connect a threaded bolt, rod, or other connector to a first end 802 of the dynamization device 800. Not shown in FIG. 8A is another threaded aperture 827 that is located at the second end 804 of the dynamization device 800. This other threaded aperture 827 may be used to connect a threaded bolt, rod, or other connector to the second end 804 of the dynamization device 800.

Figure 8B:
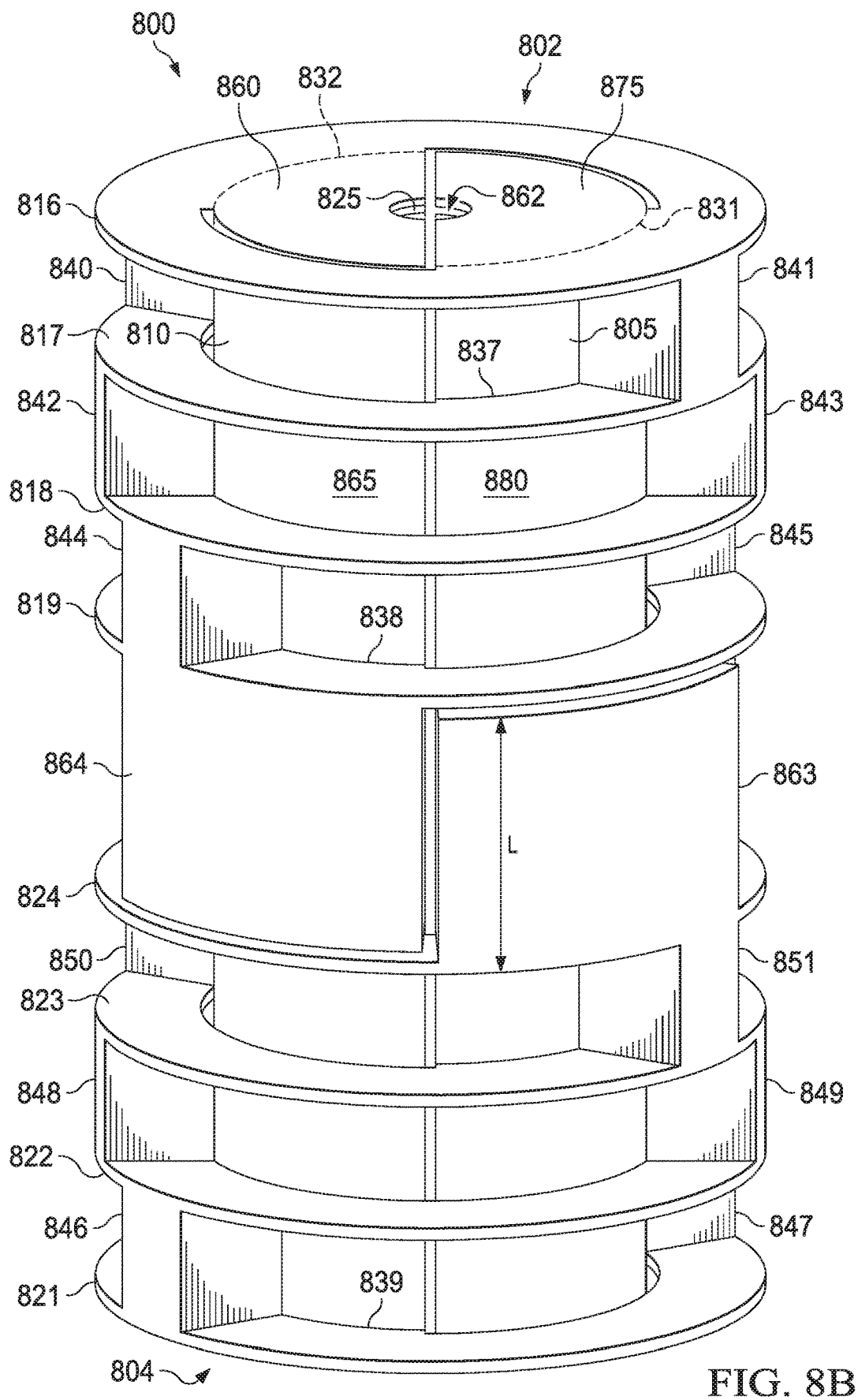
FIG. 8B illustrates another perspective view of one embodiment of a dynamization device.
Figure 8C:
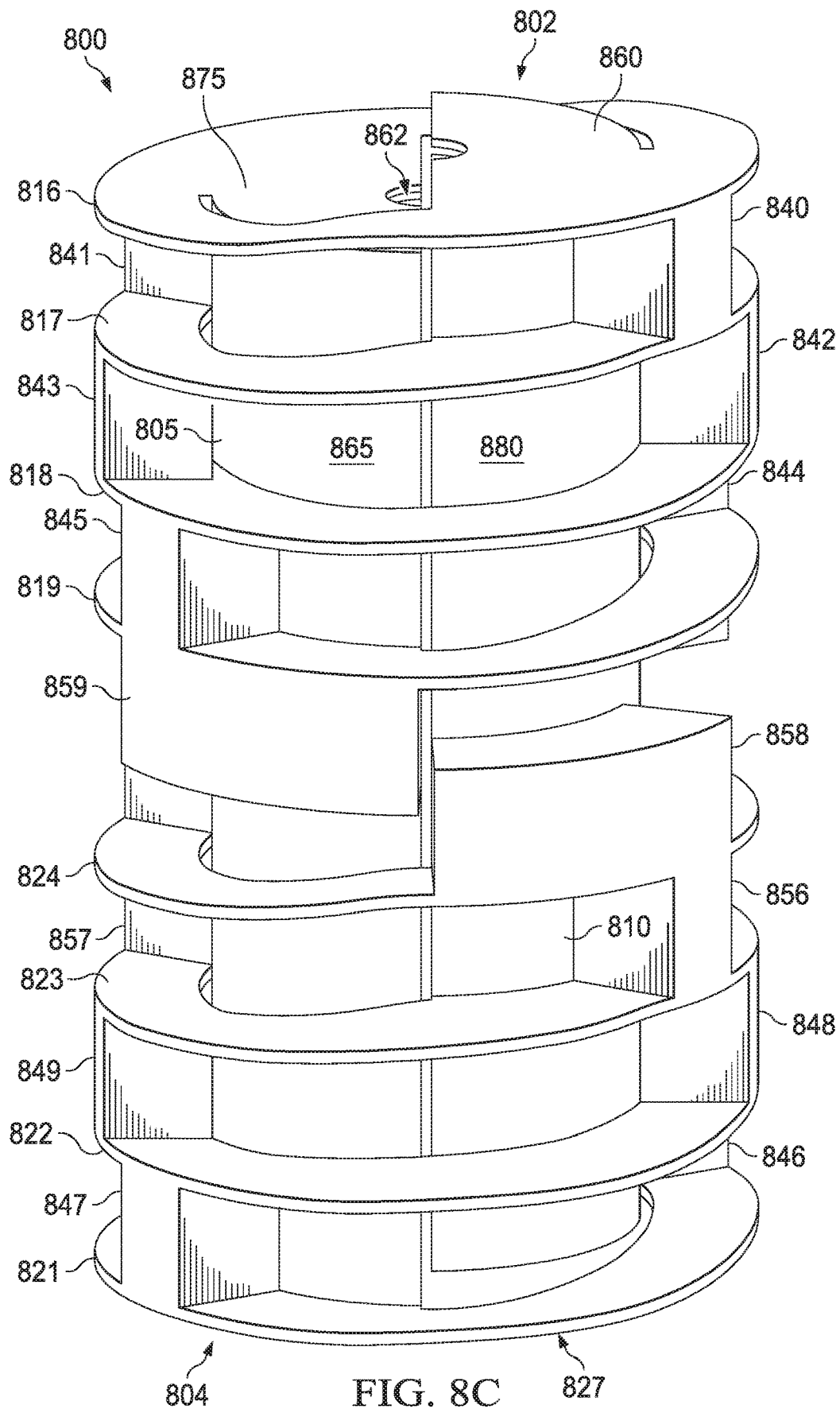
FIG. 8C illustrates a perspective view of one embodiment of a dynamization device.

An alternative view of the dynamization device 800 shown in FIG. 8A is depicted in FIG. 8B, with the device rotated 180 degrees around its longitudinal axis A-A'. Like FIG. 8A, a set of deformable rings (816-824) are positioned along the length of the dynamization device 800. Each of these rings is connected to a portion of the first and second modules 805, 810 by one or more ring connectors. The connection of the first deformable ring 816 to the first and second modules 805, 810 is depicted in FIG. 8B with ring connectors 831 and 832. These ring connectors (831, 832) may occupy radial positions that are opposite each other with respect to the longitudinal axis A-A'. In FIG. 8B, the placements of the first outer columns (840, 841), second outer columns (842, 843), third outer columns (844, 845), fourth outer columns (846, 847), fifth outer columns (848, 849), and sixth outer columns (850, 851) are seen to be rotated by 180 degrees. Ring connector 837 is also depicted as connecting the second deformable ring 817 to the first module 805. Ring connector 838 is also depicted as connecting the fourth deformable ring 819 to the second module 810. Also shown is ring connector 839, which connects the fifth deformable ring 821 to the second module 810.

Major columns 863 and 864 are depicted in FIG. 8B as attached to the eighth deformable ring 824 and the fourth deformable ring 819, respectively. Major column 863 forms a rigid connection between the eighth deformable ring 824 and the first module 805 and passes through a radial distance of about 60 degrees. Major column 863 is connected to the first module 805 for almost the entire longitudinal distance L between the eighth deformable ring 824 and the fourth deformable ring 819, thus providing additional strength and support to the entire structure of the dynamization device 800. Major column 864 forms a rigid connection between the fourth deformable ring 819 and the second module 810 and passes through a radial distance of about 60 degrees. Major column 864 is connected to the second module 810 for almost the entire longitudinal distance L between the fourth deformable ring 819 and the eighth deformable ring 824, thus providing additional strength and support to the entire structure of the dynamization device 800. Major columns 863, 864 act as stopping mechanisms to prevent longitudinal distraction of the device, which would be inconsistent with the therapeutic regimen and could cause damage to the dynamization device 800. More specifically, when the first module 805 is longitudinally distracted away from the second module 810 (in a direction opposite from that shown in FIG. 8C), the major columns 863, 864 will prevent this distractive displacement. This occurs when the upper face of the major column 863 abuts the lower face of the fourth deformable ring 819 and when the lower face of the major column 864 abuts the upper face of the eighth deformable ring 824. Since the major columns (863, 864) have a length L that is almost equal to the distance between the fourth deformable ring 819 and the eighth deformable ring 824, very little distractive displacement of the dynamization device 800 is permitted.

Figure 8D:
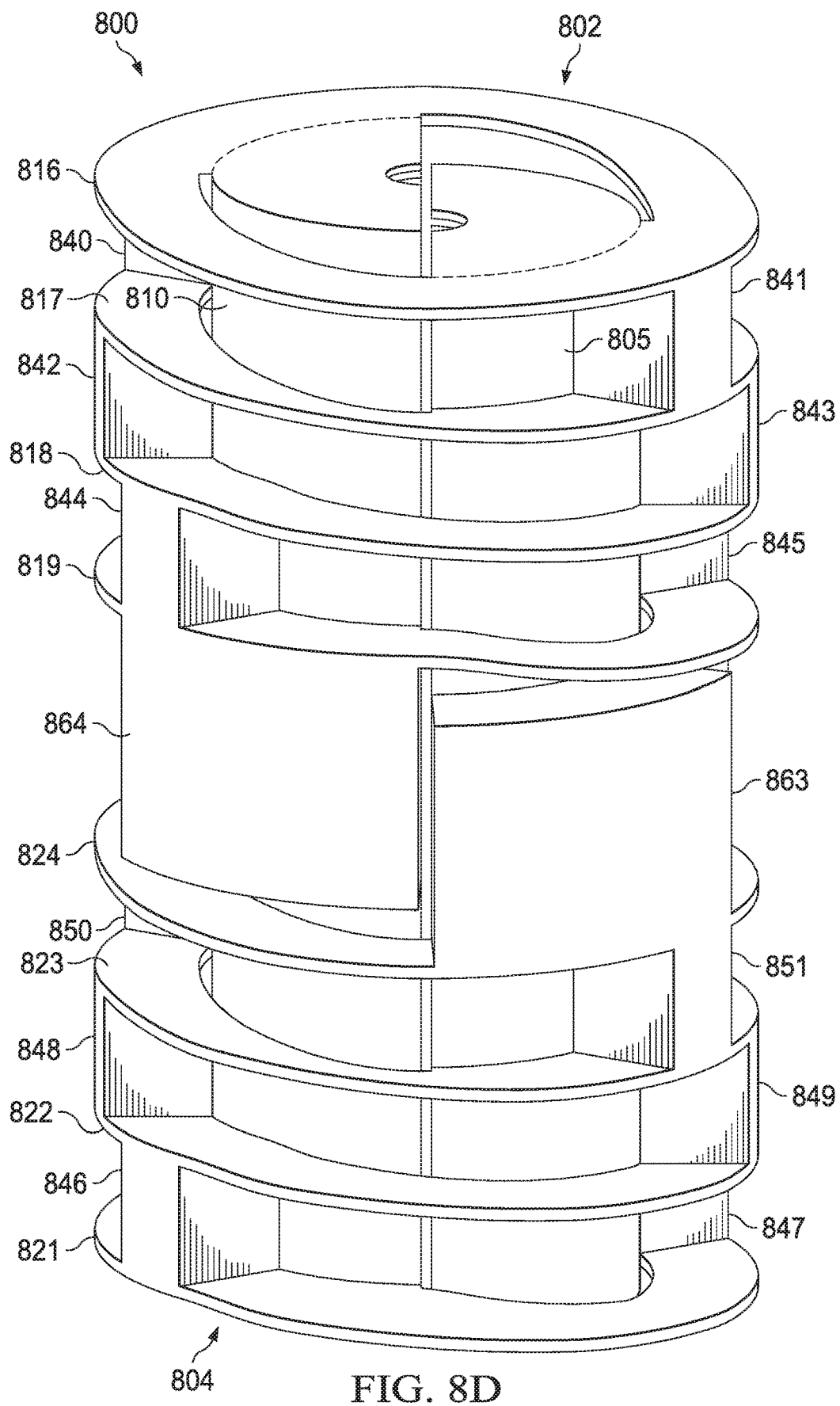
FIG. 8D illustrates another perspective view of one embodiment of a dynamization device.

In use, as shown in opposing views shown in FIGS. 8C and 8D, when the first module 805 is longitudinally displaced with respect to the second module 810, the inner columns (865, 880) and the stopping member (if in use) will stop the longitudinal displacement of the dynamization device 800. As the first module 805 is longitudinally displaced with respect to the second module 810, the deformable rings (816-824) are displaced with respect to each other. This deforms the shape of the rings 816, 817, 818, 819, 821, 822, 823, 824 so that a longitudinal mechanical bias is applied between the first and second modules 805, 810 to return the first deformable rings to their original position.

A representative diagram of the deformation of the rings when the first module 805 is displaced with respect to the second module 810 is found in FIG. 8C. FIG. 8C corresponds to the same view of the device 800 as FIG. 8A, but with the modules longitudinally displaced. As can be seen in FIG. 8C, the minor columns 858, 859 are translated past each other along their longitudinal axes. The deformation of the sections of the deformable rings that are not attached to the first and second modules 805, 810 is also apparent.

A representative diagram of the deformation of the rings when the first module 805 is displaced with respect to the second module 810 is also found in FIG. 8D. FIG. 8D corresponds to the same view of the dynamization device 800 as FIG. 8B, but with the modules longitudinally displaced. As can be seen in FIG. 8D, the major columns 864, 863 are translated away from each other along their longitudinal axes, thus creating more space between major column 865 and the eighth deformable ring 824, and more space between the major column 863 and the fourth deformable ring 819. The deformation of the sections of the deformable rings that are not attached to the modules is also apparent. The displacement of the first module 805 past the second end 804 of the dynamization device 800 is apparent in FIG. 8D. Similarly, displacement of the second module past the first end 802 of the dynamization device 800 is apparent. Any of the locking devices described above with reference to FIGS. 1F, 3, 4E, 5C, and 5D can be used with the dynamization device 800 depicted in FIGS. 8A-8D.

Figure 8E:
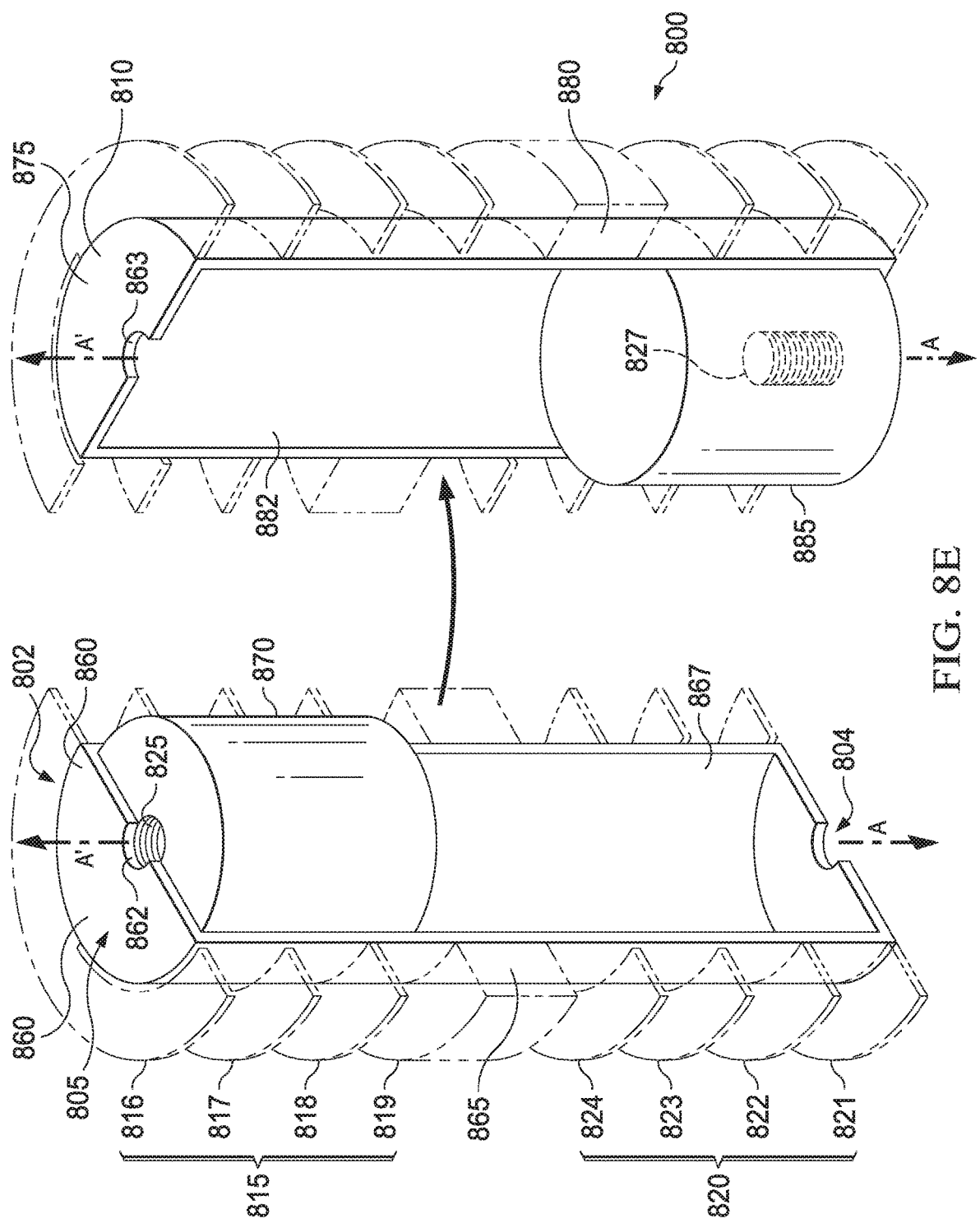
FIG. 8E illustrates an exploded view of one embodiment of a dynamization device.

The dynamization device 800 of FIGS. 8A-8D may comprise internal components similar to those shown in FIG. 8E. Namely, the first module 805 may include a semicircular cap 860 located at the first end 802. The semicircular cap 860 may comprise a central aperture 862 that is coaxial with the longitudinal axis A-A'. According to one embodiment, the central aperture 862 allows a threaded bolt, rod, or other connector to pass through the semicircular cap 860 to connect to the threaded aperture 825 in the first module 805. The first module 805 further comprises an outer wall 865 that preferably has a substantially cylindrical shape. The outer wall 865 also includes a smooth inner surface 867 at the second end 804. The first module may also comprise an inner column 870 located at a first end 802 of the first module 805. The inner column 870 preferably has a substantially cylindrical shape, but other surfaces may be used, so long as they have a smooth longitudinal surface. The outside surface of the inner column 870 is preferably of substantially the same radial distance as the inner surface 867. As shown in FIG. 8E, the device 800 also comprises a second module 810 including a semicircular cap 875 located at the first end 802. The semicircular cap 875 may comprise a central aperture 863 that is coaxial with the longitudinal axis A-A'. According to one embodiment, the central aperture 863 allows a threaded bolt, rod, or other connector to pass through the semicircular cap 875 to connect to the threaded aperture 825 in the first module 805. The second module 810 further comprises an outer wall 880 that preferably has a substantially cylindrical shape. The outer wall 880 also includes a smooth inner surface 882 at the first end of the device 802. The second module 810 may also comprise an inner column 885 located at a second end 804 of the second module 810. The inner column 885 preferably has a substantially cylindrical shape, but other surfaces may be used, so long as they have a smooth longitudinal surface. The outside surface of the inner column 885 is preferably of substantially the same radial distance as the inner surface 882. The inner column 885 may further comprise a threaded recess 827 at the second end 804 of the device. The threaded recess 827 allows a threaded bolt, rod, or other connector to be connected to a second end 804 of the dynamization device 800.

Figure 9A:
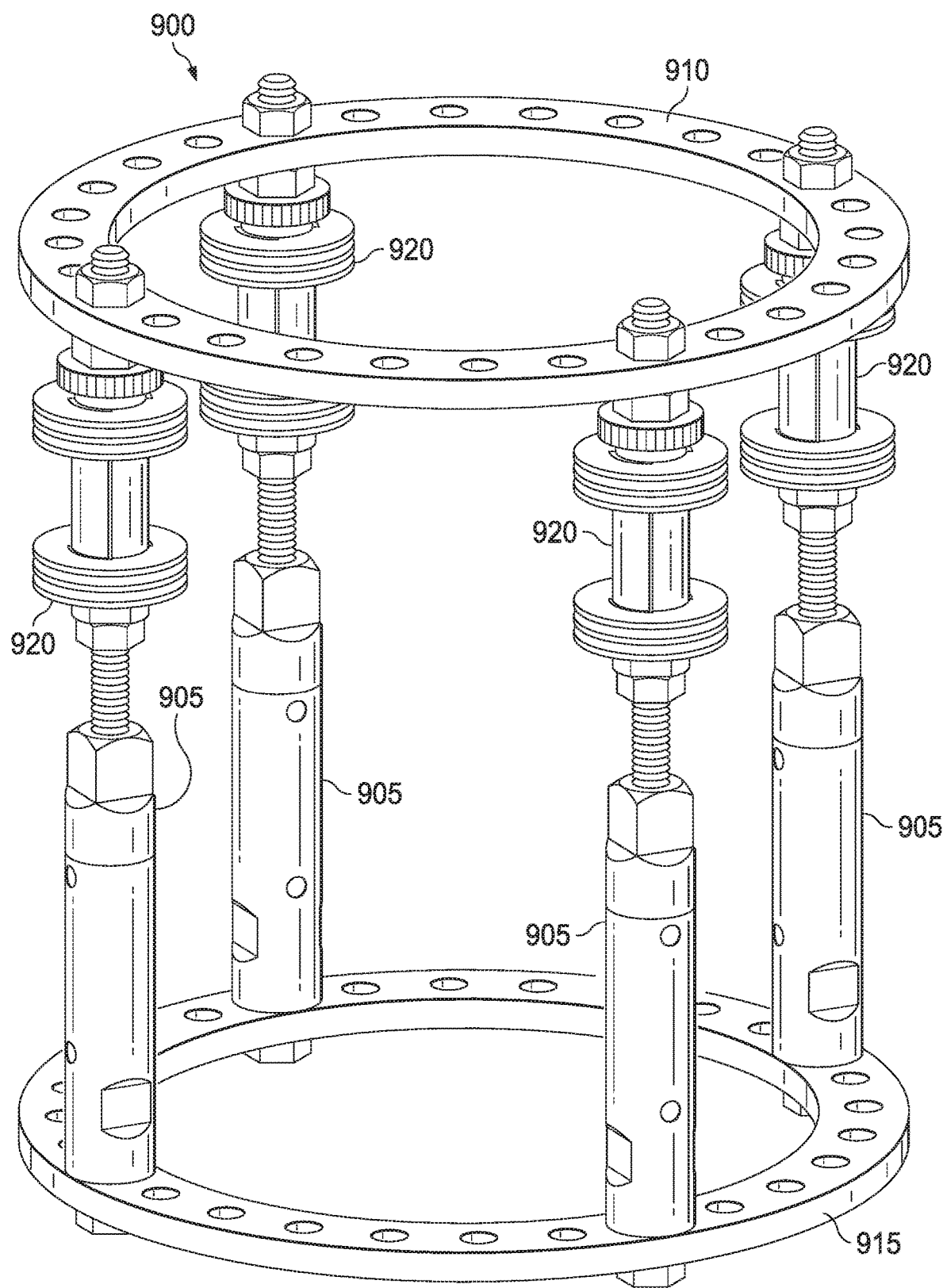
FIG. 9A illustrates a perspective view of an external fixation device comprising exemplary dynamization devices.

FIG. 9A illustrates a perspective view of an exemplary external fixation device 900 comprising external fixation struts 905 according to a specific example embodiment of the disclosure. Each of the fixation struts 905 is connected to one end of a dynamization device 920, which itself can be connected to the external fixation ring 910. The dynamization device 920 provided a limited amount of longitudinal movement to the fixation struts, thereby allowing a therapeutic amount of dynamization to be applied to the patient. As described previously, the degree of dynamization can be controlled by the dynamization devices 920, such as loosening and tightening screws and other devices on the device 920.

The use of an external fixation struts 905 may provide several advantages such as the lengthening and adjustment of the distance between the first external fixation ring 910 and the second external fixation ring 915; the rapid or gradual length adjustment between the first external fixation ring 910 and the second external fixation ring 915; and other manipulation of the orientations of the first external fixation ring 910, the second external fixation ring 915, and the various external fixation devices secured thereon. External fixation struts 905 may be secured at one end to one of the first external fixation ring 910 or the second external fixation ring 915. As depicted, four external fixation struts 905 may be used; however, the number of external fixation struts 905 may vary. For example, in some embodiments, an external fixation device 900 may comprise eight external fixation struts 905 with in a hexapod arrangement, as described in U.S. Pat. No. 8,574,232, entitled External Fixation Connection Rod for Rapid and Gradual Adjustment, the disclosure of which is incorporated by reference in its entirety. Use of the external fixation connection struts described therein as external fixation strut 905 may advantageously provide for a greater length between the first external fixation ring 910 and the second external fixation ring 915. Further, use of the external fixation connection strut described therein as external fixation strut 905 may provide for greater ease in assembling the external fixation device on a patient, or adjusting the external fixation device once secured on a patient.

The use of the disclosure in U.S. Pat. No. 8,574,232 as the external fixation strut 905 is provided by way of example only. One of ordinary skill in the art having the benefit of the present disclosure would appreciate that an external fixation strut 905 may comprise more or less features than that disclosed in U.S. Pat. No. 8,574,232. For example, in some embodiments, providing for various rotating members or articulable joints in an external fixation strut 905 may advantageously allow for greater manipulation and/or adjustment of the external fixation device 900 and the components therein. In other embodiments, utilizing an external fixation strut 905 with fewer articulable joints or rotating members may advantageously maintain parallel orientation of the first external fixation ring 910 and the second external fixation ring 915. Further, utilizing an external fixation strut 905 with fewer articulable joints or rotating members may advantageously stabilize or maintain the direction or axis of dynamization provided by the dynamization modules.

Figure 9B:
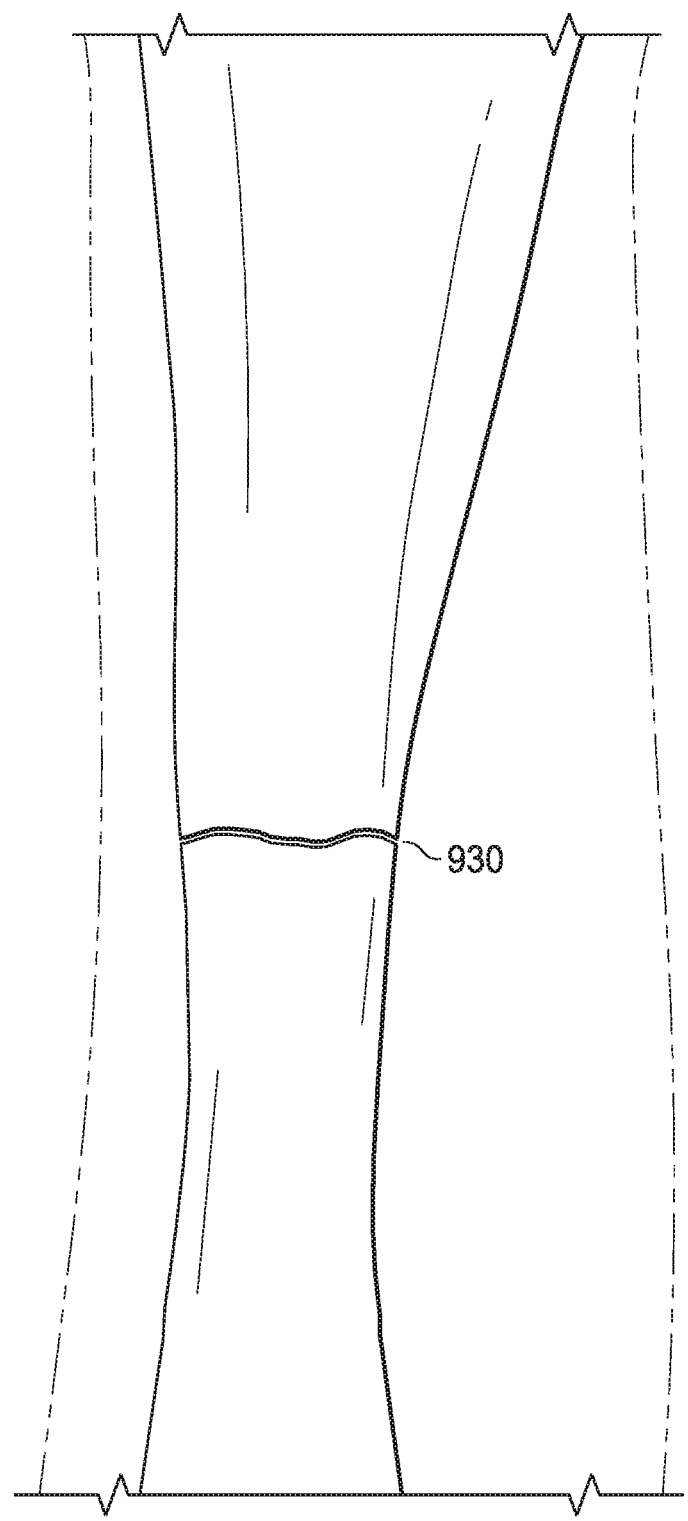
FIG. 9B illustrates a section of a person's bone with a fracture.

FIG. 9B illustrates a section of a person's bone with a fracture 930. The bone may be a femur, tibia, or fibula, or any bone of sufficient length to be stabilized by a fixator device. According to one embodiment, the bone may have one or more fractures. In an example embodiment, the fracture may be a midshaft tibial fracture that requires treatment and healing. In other embodiments, the bone may belong to other parts of the person's body.

Figure 9C:
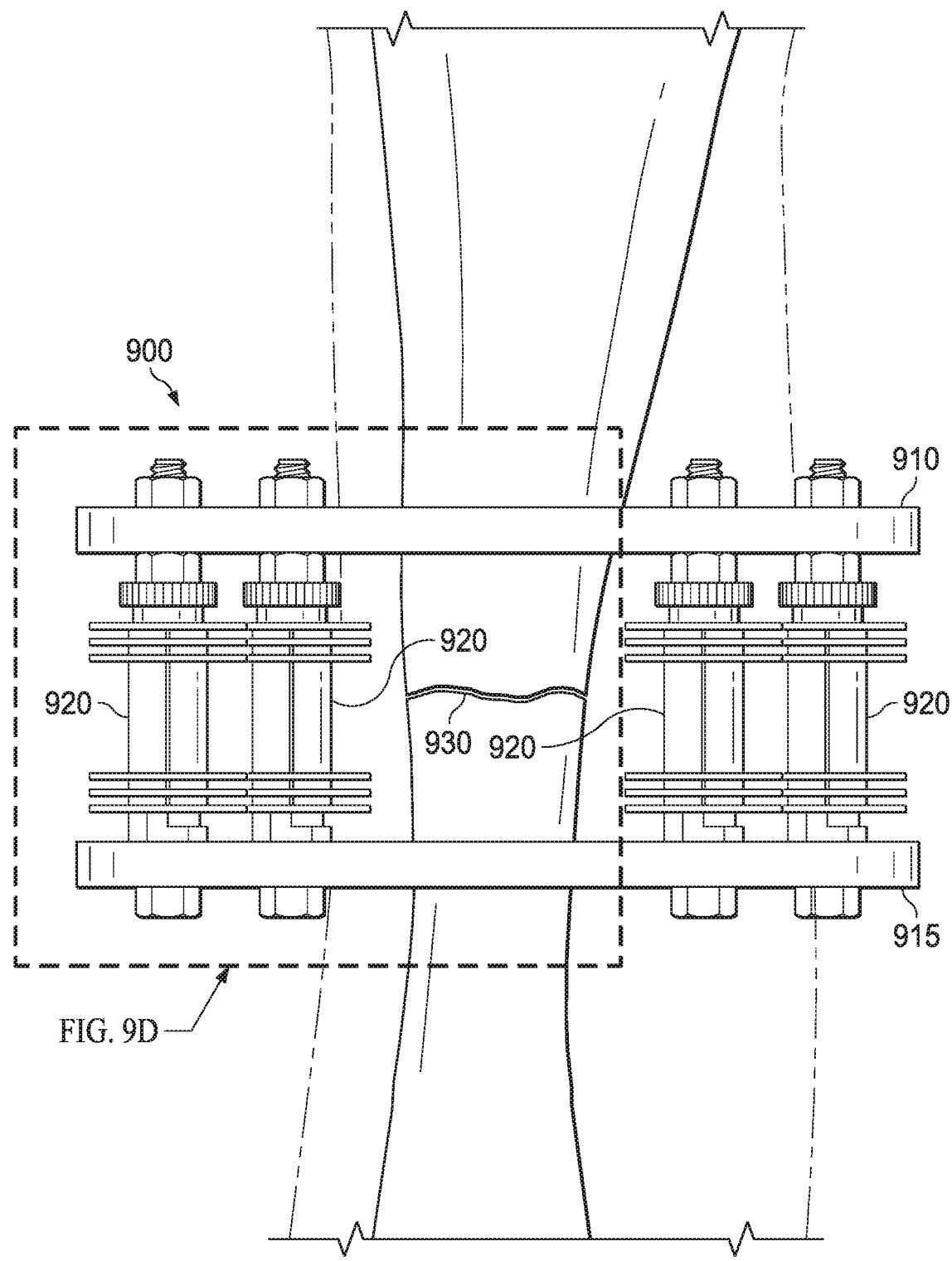
FIG. 9C illustrates exemplary dynamization devices surrounding a person's bone with a fracture.

FIG. 9C illustrates an external fixation device 900 surrounding a person's bone with a fracture 930. As shown in this figure, four dynamization devices 920 are attached to external fixation rings 910 and 920. No external fixation struts are used in this embodiment. The dynamization devices 920 allow a therapeutic amount of dynamization to be applied to the external fixation device 900 during the fracture healing process.

Figure 9D:
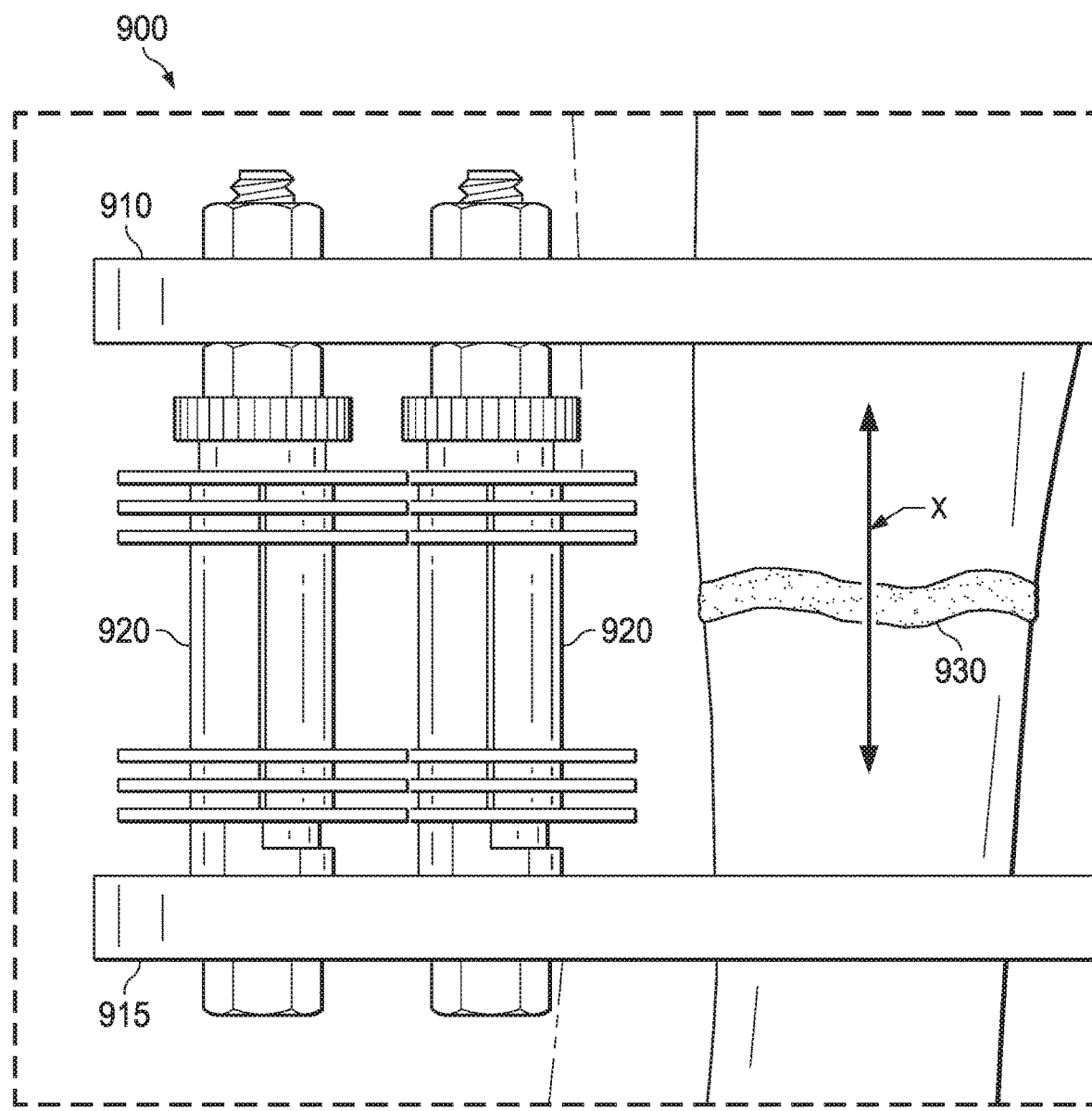
FIG. 9D illustrates a close-up view of exemplary dynamization devices surrounding a person's bone with a fracture.

FIG. 9D illustrates a close up view of an external fixation device 900 surrounding a person's bone with a fracture 930. As depicted, a plurality of dynamization devices 920 may be installed or secured to a first external fixation ring 910 and a second external fixation ring 915 that surround the bone. The dynamization devices 920 shown in FIGS. 9C and 9D may be the same as any one of the embodiments disclosed and described above, or any one of the embodiments depicted in FIGS. 1A, 1B, 1C, 1D, 1E, 1F, 4A, 4B, 4C, 4D, 4E, 5A, 5B, 5D, 5E, 5E, 5F, 5G, 6A, 6B, 6C, 7A, 7B, 7C, 8A, 8B, 8C and/or FIG. 8D. The bone shown may be a femur, tibia, or fibula, or any other long bone to which the therapeutic treatment is to be given. In other embodiments, the bone may belong to other parts of the person's body. Since the bone shown in FIGS. 9B and 9C can represent various bones of a person's body, in certain embodiments, the dimensions of the bone may be out of proportion with reference to these exemplary drawings. In an embodiment, pins (not shown) attached to the external fixation device 900 are connected to the bones near a fracture that requires healing (e.g., a person's tibia). The pins (not shown) may be drilled or pierced into the person's skin and bone for installation of the external fixation device 900. Connection of the external fixation device 900 to the bone(s) may include placing connectors, such as wires, pins, screws, and/or rods, among others through the skin and into, through, and/or around the selected bone(s).

In some embodiments, the dynamization devices 900 may advantageously be positioned parallel to one another. In some embodiments, the first external fixation ring 910 and the second external fixation ring 915 may be positioned parallel to one another, and the dynamization devices 920 may advantageously be positioned orthogonal to a plane of the first external fixation ring 910 and the second external fixation ring 915. Such arrangements may advantageously provide for controlled dynamization along a longitudinal axis of the direction of the dynamization devices 920.

Figure 9E:
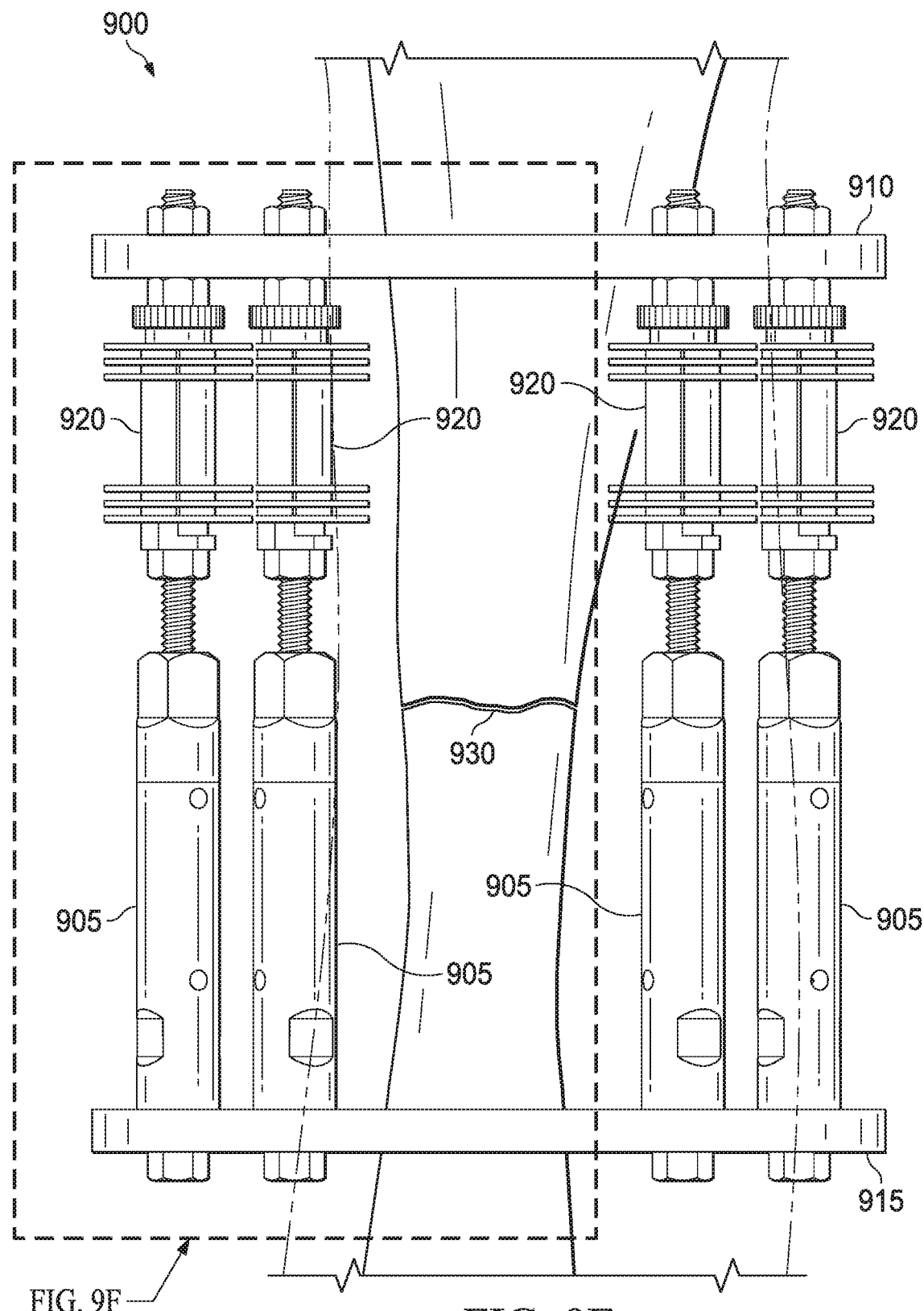
FIG. 9E illustrates exemplary dynamization devices surrounding a person's bone with a fracture.
Figure 9F:
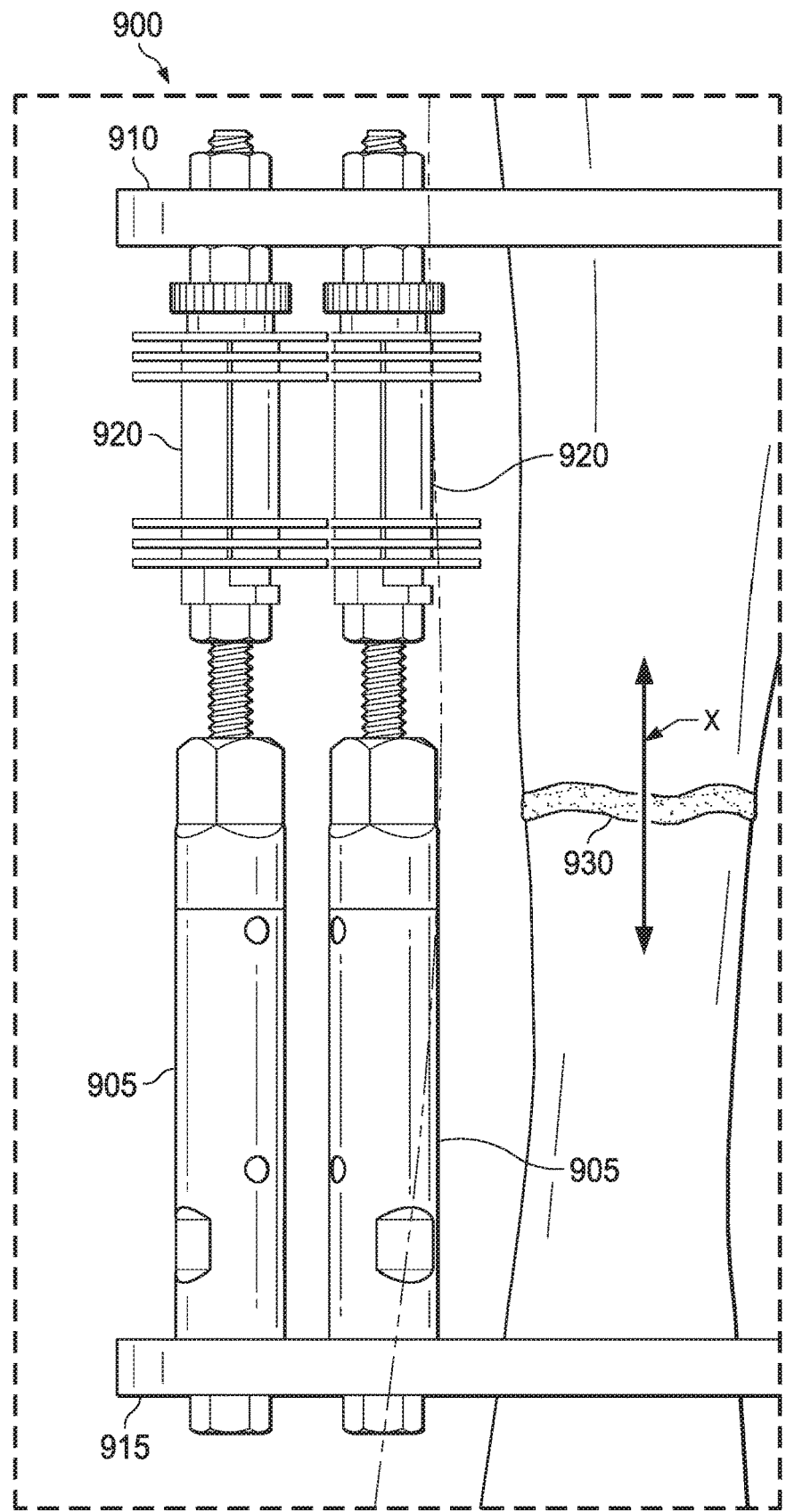
FIG. 9F illustrates a close-up view of exemplary dynamization devices surrounding a person's bone with a fracture.

FIG. 9E illustrates another example embodiment of an external fixation device 900 surrounding a person's bone with a fracture 930. FIG. 9F illustrates a close up view the external fixation device 900 surrounding a person's bone with a fracture 930. In addition to the components depicted in FIG. 9C and FIG. 9D, the example embodiments of FIG. 9E and FIG. 9F may further comprise a plurality of external fixation struts 905, wherein each of the external fixation struts 905 are secured at one end to a dynamization device 920 and at another end to one of the first external fixation ring 910 or the second external fixation ring 915. As described above, external fixation struts 905 may be that of the external fixation connection rod described in U.S. Pat. No. 8,574,232, entitled External Fixation Connection Rod for Rapid and Gradual Adjustment, the disclosure of which is incorporated by reference in its entirety. Use of the external fixation connection strut described therein as external fixation strut 905 may advantageously provide for a greater length between the first external fixation ring 910 and the second external fixation ring 915. Further, use of the external fixation connection strut described therein as external fixation strut 905 may provide for greater ease in assembling the external fixation device on a patient, or adjusting the external fixation device once secured on a patient.

As explained above, the use of the disclosure in U.S. Pat. No. 8,574,232 as the external fixation strut 905 is provided by way of example only. One of ordinary skill in the art having the benefit of the present disclosure would appreciate that an external fixation strut 905 may comprise more or less features than that disclosed in U.S. Pat. No. 8,574,232. For example, in some embodiments, providing for various rotating members or articulable joints in an external fixation strut 905 may advantageously allow for greater manipulation and/or adjustment of the external fixation device 900 and the components therein. In other embodiments, utilizing an external fixation strut 905 with fewer articulable joints or rotating members may advantageously maintain parallel orientation of the first external fixation ring 910 and the second external fixation ring 915. Further, utilizing an external fixation strut 905 with fewer articulable joints or rotating members may advantageously stabilize or maintain the direction or axis of dynamization provided by the dynamization devices 920.

Figure 10:
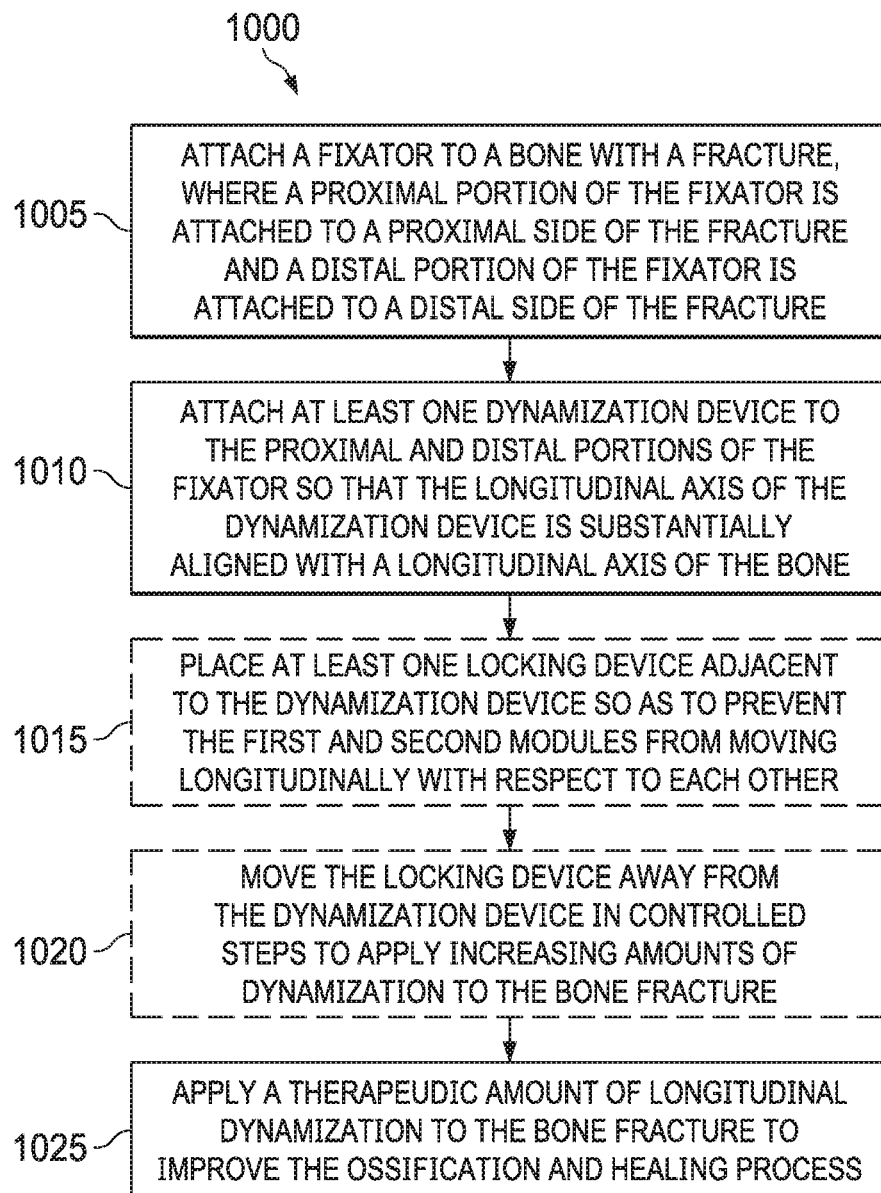
FIG. 10 illustrates an exemplary method for applying therapeutic dynamization from a dynamization device to a bone fracture.

A representative process for applying therapeutic dynamization from a dynamization device to a bone fracture (1000) is found in FIG. 10. In FIG. 10, the method starts by attaching a fixator to a bone with a fracture, where a proximal portion of the fixator is attached to a proximal side of the fracture and a distal portion of the fixator is attached to a distal side of the fracture (1005). At least one dynamization device is attached to the proximal and distal portions of the fixator so that the longitudinal axis of the dynamization device is substantially aligned with a longitudinal axis of the bone (1010). Optionally, a locking device can be placed adjacent to the dynamization device so as to prevent the first and second modules from moving longitudinally with respect to each other (1015). This prevents any dynamization or longitudinal motion of the fixator device, which can be useful early in the healing process of the fracture. Once it is determined that the fracture has healed enough to apply dynamization, the locking device can (optionally) be moved away from the dynamization device in controlled steps to apply increasing amounts of dynamization to the bone fracture (1020). Ultimately, a therapeutic amount of longitudinal dynamization should be applied to the bone fracture to improve the ossification and healing process (1025), as directed by a surgeon or otherwise qualified physician.

As seen from the above description, the present disclosure provides for various embodiments of a dynamization device. Embodiments of the present disclosure may provide for compression of a biasing member disposed within the dynamization device. Compression of the biasing member may occur without a corresponding change in the position or movement of the shaft and/or the sleeve. Consequently, a total length of the strut may not change during adjustment. Rather, only the biasing force and potential range of motion change may be adjusted. The range of motion afforded by the external fixation strut may be effected by the biasing force, but may be mechanically limited by the position of the bushing or rotatable feature. Thus, a biasing member may be compressed without a corresponding change in the total length of the strut. Rather, any change in the length of the strut may occur as a result of external compressive forces acting upon it.

The disclosed dynamization devices can be fabricated with a variety of techniques, including an additive or 3D printing process with materials such plastic, polymer, thermoplastic, metal, metal alloy, composite, resin, ultra-high-molecular-weight polyethylene (UHMW), a polytetrafluoroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. The dynamization devices can also fabricated with medical grade or biocompatible materials such as the following:

Polyvinylchloride or PVC;
Polyethersulfone or PES;
Polytetrafluoroethylene or PTFE;
Polyethylene (PE-UHMW or PE-LD & HD);
Polyurethane or PU;
Polyetherimide, PEI;
Polycarbonate or PC;
Polysulfone or PS;
Polyetheretherketone or PEEK; or
Polypropylene or PP.

The dynamization devices can also be fabricated by machining, forging or casting, based on the specific design and intended use of the device and the material comprising the device. Suitable materials include the medical grade and biocompatible plastics described above, or biocompatible metals, such as titanium, stainless steel, 316L stainless steel, cobalt-chromium, and alloys thereof. According to some embodiments, the devices can be made as a composite or hybrid device with a combination of plastic and metallic components. The selected material must have sufficient plasticity and shape memory to return to its original configuration after having been deformed many times.

As will be understood by those skilled in the art who have the benefit of the instant disclosure, other equivalent or alternative compositions, devices, methods, and systems for external fixation struts can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints.

All or a portion of a device and/or system for therapeutic dynamization may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim. For each of the claims, each dependent claim can depend both from the independent claim and from each of the prior dependent claims for each and every claim so long as the prior claim provides a proper antecedent basis for a claim term or element.

The title, abstract, background, and headings are provided in compliance with regulations and/or for the convenience of the reader. They include no admissions as to the scope and content of prior art and no limitations applicable to all disclosed embodiments.

The invention claimed is:

1. A dynamization device having a longitudinal axis, the device comprising:
   a first module and a second module, wherein the first and second modules are each rigidly affixed to and mated together by one or more deformable rings, each of the first and second modules comprising an inner column positioned within the one or more deformable rings;
   wherein the mated first and second modules form a first displacement gap between the inner column of the first module and the inner column of the second module, the first displacement gap extending along the longitudinal axis between adjacent deformable rings of the one or more deformable rings.

2. The dynamization device according to claim 1, wherein first and second modules are made from at least one of plastic, polymer, thermoplastic, metal, metal alloy, composite, resin, ultra-high-molecular-weight polyethylene (UHMW), a polytetrafluroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, or polycarbonate.

3. The dynamization device according to claim 2, wherein the polymer comprises a thermoplastic polymer, a polyolefin, a polyester, a poly silicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a poly sulfone, a polycarbonate, a polyacetal, poly(hydroxynapthoic acid), a conductive polymer, a poly(3-hexylthiophene), a polyphenylenevinylene, a poly(phenylene vinylene), a polyaniline, or a combination thereof.

4. A dynamization device having a longitudinal axis, the device comprising:
   a first module comprising:
      an outer wall,
      a first cap located at a first end of the first module, the first cap comprising a central aperture, and
      an inner column located at a first end of the first module, the inner column comprising a threaded recess at the first end that is aligned with the central aperture of the first cap,
      wherein the outer wall, the central aperture, the threaded recess, and the inner column of the first module are coaxial with the longitudinal axis of the device,
   a second module comprising:
      an outer wall,
      a second cap located at a second end of the second module, the second cap comprising a central aperture, and
      an inner column located at a second end of the second module, the inner column comprising a threaded recess at the second end,
      wherein the outer wall, the central aperture, the threaded recess, and the inner column of the second module are coaxial with the longitudinal axis,
   wherein the first and second modules can be mated together such that inner column of the first module is positioned within the outer wall of the second module and the inner column of the second module is positioned within the outer wall of the first module;
   wherein the mated first and second modules form a displacement gap between the inner column of the first module and the inner column of the second module;
   a plurality of proximal deformable rings positioned at the first end of the mated first and second modules, wherein each of the proximal deformable rings is connected to a portion the first module and to a portion of the second module by ring connectors that are radially positioned opposite each other thereby permitting the second module to be longitudinally displaced with respect to the first module by deforming the each of the proximal deformable rings;
   a plurality of distal deformable rings positioned at the second end of the mated first and second modules, wherein each of the distal deformable rings is connected to a portion the first module and to a portion of the second module by ring connectors that are radially positioned opposite each other thereby permitting the second module to be longitudinally displaced with respect to the first module by deforming the each of the distal deformable rings;
   a proximal minor column connected to a portion of the outer wall of the first module and a portion of one of the proximal deformable rings;
   a proximal major column connected to a portion of the outer wall of the second module and a portion of one of the proximal deformable rings, wherein the proximal major column is positioned on a radially opposite side of the device from the proximal minor column;
   a distal minor column connected to a portion of the outer wall of the second module, and a portion of one of the distal deformable rings; and
   a distal major column connected to a portion of the outer wall of the first module and a portion of one of the distal deformable rings, wherein the distal major column is positioned on a radially opposite side of the device from the distal minor column.

5. The dynamization device according to claim 4, wherein the plurality of proximal deformable rings comprises:
   a first deformable ring positioned at a first end of the first and second modules and connected to a portion the first module and connected to a portion of the second module by first ring connectors that are radially positioned opposite each other thereby permitting the second module to be longitudinally displaced with respect to the first module by deforming the first deformable ring;

a second deformable ring longitudinally positioned away from the first deformable ring and connected to a portion of the outer wall of the first module and connected to a portion of the outer wall of the second module by second ring connectors that are radially positioned opposite each other, thereby permitting the second module to be longitudinally displaced with respect to the first module by deforming the second deformable ring;

a third deformable ring longitudinally positioned away from the second deformable ring and connected to a portion of the outer wall of the first module and connected to a portion of the outer wall of the second module by third ring connectors that are radially positioned opposite each other, thereby permitting the second module to be longitudinally displaced with respect to the first module by deforming the third deformable ring;

a fourth deformable ring longitudinally positioned away from the third deformable ring and connected to a portion of the outer wall of the first module and connected to a portion of the outer wall of the second module by fourth ring connectors that are radially positioned opposite each other, thereby permitting the second module to be longitudinally displaced with respect to the first module by deforming the fourth deformable ring;

wherein the first ring connectors, second ring connectors, third ring connectors, and fourth ring connectors are positioned at first, second, third, and fourth radial positions with respect to the longitudinal axis;

at least two first outer columns connecting the first deformable ring to the second deformable ring, wherein one of the first outer columns is connected to the outer wall of the first module and another of the first outer columns is connected to the outer wall of the second module;

wherein the first outer columns are positioned on radially opposite sides of the device;

at least two second outer columns connecting the second deformable ring to the third deformable ring, wherein one of the second outer columns is connected to the outer wall of the first module and another of the second outer columns is connected to the outer wall of the second module, and wherein the second outer columns are positioned on radially opposite sides of the device;

at least two third outer columns connecting the third deformable ring to the fourth deformable ring, wherein one of the third outer columns is connected to the outer wall of the first module and another of the third outer columns is connected to the outer wall of the second module;

wherein the third outer columns are positioned on radially opposite sides of the device;

and wherein the plurality of distal deformable rings comprises:

a fifth deformable ring positioned at a second end of the first and second modules and connected to a portion the second module and connected to a portion of the first module by fifth ring connectors that are radially positioned opposite each other, thereby permitting the second module to be longitudinally displaced with respect to the first module by deforming the fifth deformable ring;

a sixth deformable ring longitudinally positioned away from the fifth deformable ring and connected to a portion of the outer wall of the first module and connected to a portion of the outer wall of the second module by fifth ring connectors that are radially positioned opposite each other, thereby permitting the second module to be longitudinally displaced with respect to the first module by deforming the sixth deformable ring;

a seventh deformable ring longitudinally positioned away from the sixth deformable ring and connected to a portion of the outer wall of the first module and connected to a portion of the outer wall of the second module by seventh ring connectors that are radially positioned opposite each other, thereby permitting the second module to be longitudinally displaced with respect to the first module by deforming the seventh deformable ring;

an eighth deformable ring longitudinally positioned away from the seventh deformable ring and connected to a portion of the outer wall of the first module and connected to a portion of the outer wall of the second module by eighth ring connectors that are radially positioned opposite each other, thereby permitting the second module to be longitudinally displaced with respect to the first module by deforming the eighth deformable ring;

wherein the fifth, sixth, seventh, and eighth ring connectors are positioned at fifth, sixth, seventh, and eighth radial positions, respectively, with respect to the longitudinal axis;

at least two fourth outer columns connecting the fifth deformable ring to the sixth deformable ring, wherein one of the fourth outer columns is connected to the outer wall of the first module and another of the fourth outer columns is connected to the outer wall of the second module, and wherein the fourth outer columns are positioned on radially opposite sides of the device;

at least two fifth outer columns connecting the sixth deformable ring to the seventh deformable ring, wherein one of the fifth outer columns is connected to the outer wall of the first module and another of the fifth outer columns is connected to the outer wall of the second module, and wherein the fifth outer columns are positioned on radially opposite sides of the device; and at least two sixth outer columns connecting the seventh deformable ring to the eighth deformable ring, wherein one of the sixth outer columns is connected to the outer wall of the first module and another of the sixth outer columns is connected to the outer wall of the second module, and wherein the sixth outer columns are positioned on radially opposite sides of the device.

6. A dynamization device according to claim 5, wherein a distance between the proximal minor column and the eighth deformable ring is substantially equal to the displacement gap;

wherein a distance between the distal minor column and the fourth deformable ring is substantially equal to the displacement gap;

wherein the proximal major column is adjacent to the eighth deformable ring; and wherein the distal major column is adjacent to the fourth deformable ring.

7. A dynamization device according to claim 4, wherein the outer walls of the first and second modules are substantially cylindrical.

8. A dynamization device according to claim 7, wherein the inner columns of the first and second modules are substantially cylindrical.

9. A dynamization device according to claim 8, wherein each of the first and second caps of the first and second modules has a semicircular shape.

10. A dynamization device according to claim 4, further comprising a first threaded rod adapted to be received within the threaded recess of the first module and a second threaded rod adapted to be received within the threaded recess of the second module.

11. A dynamization device according to claim 10, wherein at least one threaded fastener can be threaded on to one of the first or second threaded rods so as to prevent the first and second modules from moving longitudinally with respect to each other.

12. A dynamization device according to claim 4, wherein the plurality of proximal deformable rings and the plurality of distal deformable rings are comprised of a material selected from the group consisting of ABS plastic, PLA, polyamide, glass filled polyamide, epoxy resin, silver, titanium, steel, wax, photopolymer, and polycarbonate.

13. A dynamization device according to claim 4, wherein the device is comprised of a material selected from the group consisting of ABS plastic, PLA, polyamide, glass filled polyamide, epoxy resin, silver, titanium, steel, wax, photopolymer, and polycarbonate.

14. A dynamization device according to claim 4, wherein the device is fabricated by an additive printing process.

\* \* \* \* \*